United States Patent
Gao et al.

(10) Patent No.: US 12,398,378 B2
(45) Date of Patent: Aug. 26, 2025

(54) AAV-MEDIATED GENE THERAPY FOR MAPLE SYRUP URINE DISEASE (MSUD)

(71) Applicants: University of Massachusetts, Westborough, MA (US); The Clinic for Special Children, Inc., Strasburg, PA (US)

(72) Inventors: Guangping Gao, Worcester, MA (US); Dan Wang, Worcester, MA (US); Jiaming Wang, Worcester, MA (US); Kevin A. Strauss, Strasburg, PA (US)

(73) Assignees: University of Massachusetts, Westborough, MA (US); The Clinic for Special Children, Inc., Strasburg, PA (US)

( * ) Notice: Subject to any disclaimer, the term of this patent is extended or adjusted under 35 U.S.C. 154(b) by 962 days.

(21) Appl. No.: 17/602,353

(22) PCT Filed: Apr. 10, 2020

(86) PCT No.: PCT/US2020/027622
§ 371 (c)(1),
(2) Date: Oct. 8, 2021

(87) PCT Pub. No.: WO2020/210595
PCT Pub. Date: Oct. 15, 2020

(65) Prior Publication Data
US 2022/0162570 A1 May 26, 2022

Related U.S. Application Data

(60) Provisional application No. 62/930,687, filed on Nov. 5, 2019, provisional application No. 62/833,159, filed on Apr. 12, 2019.

(51) Int. Cl.
| | | |
|---|---|---|
| *C12N 9/02* | (2006.01) | |
| *A61K 48/00* | (2006.01) | |
| *A61P 3/00* | (2006.01) | |
| *C12N 15/86* | (2006.01) | |

(52) U.S. Cl.
CPC ........ *C12N 9/0008* (2013.01); *A61K 48/0058* (2013.01); *A61P 3/00* (2018.01); *C12N 15/86* (2013.01); *C12Y 102/04004* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | |
|---|---|---|
| 2013/0323226 A1 | 12/2013 | Wilson et al. |
| 2018/0221402 A1 | 8/2018 | Prieve et al. |
| 2024/0207370 A1 | 6/2024 | Gao et al. |

FOREIGN PATENT DOCUMENTS

| | | | |
|---|---|---|---|
| CN | 104099349 A | 10/2014 | |
| CN | 107073051 A | 8/2017 | |
| JP | 2019-504888 A | 2/2019 | |
| WO | WO 02/12316 A1 | 2/2002 | |
| WO | WO-2017136202 A1 * | 8/2017 | ............ A61K 45/06 |
| WO | WO-2017191274 A2 * | 11/2017 | ......... A61K 31/7088 |
| WO | WO 2018/016884 A1 | 1/2018 | |
| WO | WO 2018/185110 A1 | 10/2018 | |
| WO | WO 2019/071048 A1 | 4/2019 | |
| WO | WO 2020/210595 A1 | 10/2020 | |

OTHER PUBLICATIONS

Ali, Ernie Zuraida, and Lock-Hock Ngu. "Fourteen new mutations of BCKDHA, BCKDHB and DBT genes associated with maple syrup urine disease (MSUD) in Malaysian population." Molecular genetics and metabolism reports 17 (2018): 22-30. (Year: 2018).*

Chuang, Jacinta L., et al. "Molecular basis of maple syrup urine disease: novel mutations at the E1 alpha locus that impair E1 (alpha 2 beta 2) assembly or decrease steady-state E1 alpha mRNA levels of branched-chain alpha-keto acid dehydrogenase complex." American journal of human genetics 55.2 (Year: 1994).*

Chuang, Jacinta L., et al. "Molecular and biochemical basis of intermediate maple syrup urine disease. Occurrence of homozygous G245R and F364C mutations at the E1 alpha locus of Hispanic-Mexican patients." The Journal of clinical investigation 95.3 (1995): 954-963. (Year: 1995).*

Fischer, M. Dominik, et al. "Codon-optimized RPGR improves stability and efficacy of AAV8 gene therapy in two mouse models of X-linked retinitis pigmentosa." Molecular Therapy 25.8 (2017): 1854-1865. (Year: 2017).*

Koyata, Hirohisa, R. P. Cox, and D. T. Chuang. "Stable correction of maple syrup urine disease in cells from a Mennonite patient by retroviral-mediated gene transfer." Biochemical Journal 295.3 (1993): 635-639. (Year: 1993).*

(Continued)

*Primary Examiner* — Tracy Vivlemore
*Assistant Examiner* — Fatimah Khalaf Matalkah
(74) *Attorney, Agent, or Firm* — Wolf, Greenfield & Sacks, P.C.

(57) ABSTRACT

In some aspects the disclosure provides compositions and methods for promoting expression of functional BCKDHA protein, which is the E1-alpha subunit of the branched-chain alpha-keto acid (BCAA) dehydrogenase complex, in a subject. In some aspects the disclosure provides compositions and methods for promoting expression of functional BCKDHB protein, which is the E1-beta subunit of the branched-chain alpha-keto acid (BCAA) dehydrogenase complex, in a subject. In some aspects the disclosure provides compositions and methods for promoting expression of functional BCKDHA and BCKDHB proteins, in a subject. In some embodiments, the disclosure provides methods of treating a subject having Maple Syrup Urine Disease (MSUD).

8 Claims, 7 Drawing Sheets

Specification includes a Sequence Listing.

(56) References Cited

OTHER PUBLICATIONS

Skvorak, Kristen J. Investigation of gene and cellular therapies to cure maple syrup urine disease (MSUD) in a genetically engineered mouse model. Diss. University of Pittsburgh, 2008. (Year: 2008).*
Zhang, B., et al. "Evidence for both a regulatory mutation and a structural mutation in a family with maple syrup urine disease." The Journal of clinical investigation 83.4 (1989): 1425-1429. (Year: 1989).*
Zincarelli, Carmela, et al. "Analysis of AAV serotypes 1-9 mediated gene expression and tropism in mice after systemic injection." Molecular therapy 16.6 (2008): 1073-1080. (Year: 2008).*
Invitation to Pay Additional Fees for Application No. PCT/US2020/027622, mailed Jul. 16, 2020.
International Search Report and Written Opinion for Application No. PCT/US2020/027622, mailed Sep. 3, 2020.
International Preliminary Report on Patentability for Application No. PCT/US2020/027622, mailed Oct. 21, 2021.
[No Author Listed], Branched-Chain Keto Acid Dehydrogenase E1, Alpha Polypeptide; BCKDHA. OMIM Accession No. 608348. Dec. 17, 2003. Retrieved on Aug. 24, 2020 from www.omim.org/entry/608348. 5 pages.
PCT/US2020/027622, Jul. 16, 2020, Invitation to Pay Additional Fees.
PCT/US2020/027622, Sep. 3, 2020, International Search Report and Written Opinion.
PCT/US2020/027622, Oct. 21, 2021, International Preliminary Report on Patentability.
Extended European Search Report for Application No. 20787676.4, mailed Mar. 13, 2013.
Invitation to Pay Additional Fees for Application No. PCT/US2022/026382, mailed Jul. 29, 2022.
International Search Report and Written Opinion for Application No. PCT/US2022/026382, mailed Sep. 23, 2022.
International Preliminary Report on Patentability for Application No. PCT/US2022/026382, mailed Nov. 9, 2023.
Ali et al., Fourteen new mutations of BCKDHA, BCKDHB and DBT genes associated with maple syrup urine disease (MSUD) in Malaysian population. Mol Genet Metab Rep. Sep. 13, 2018:17:22-30. doi: 10.1016/j.ymgmr.2018.08.006. eCollection Dec. 2018.
Han et al., Two novel mutations in the BCKDHB gene that cause maple syrup urine disease. Pediatr Neonatol. Oct. 2018;59(5):515-519. doi: 10.1016/j.pedneo.2018.01.006. Epub Jan. 6, 2018.
Li et al., Eleven novel mutations of the BCKDHA, BCKDHB and DBT genes associated with maple syrup urine disease in the Chinese population: Report on eight cases. Eur J Med Genet. Nov. 2015;58(11):617-23. doi: 10.1016/j.ejmg.2015.10.002. Epub Oct. 8, 2015.
Li et al., Clinical, biochemical and genetic study of 13 children with maple syrup urine disease. Chinese Journal of Applied Clinical Pediatrics. Jan. 11, 2019; 31(8):569-572.
Skvorak et al., Placental stem cell correction of murine intermediate maple syrup urine disease. Hepatology. Mar. 2013;57(3):1017-23. doi: 10.1002/hep.26150. Epub Feb. 15, 2013.
Zhang et al., Report of a BCKDHA gene mutation-associated thiamine effective maple syrup urine disease case. Chinese Journal of Evidence Based Pediatrics. Feb. 5, 2016; 11(1): 75-77.
EP 20787676.4, Dec. 7, 2022, Partial European Search Report.
Partial European Search Report for Application No. 20787676.4, mailed Dec. 7, 2022.
Chuang et al., Molecular and biochemical basis of intermediate maple syrup urine disease. Occurrence of homozygous G245R and F364C mutations at the E1 alpha locus of Hispanic-Mexican patients. J Clin Invest. Mar. 1995;95(3):954-63. doi: 10.1172/JCI117804.
Fernández-Guerra et al., Functional characterization of the novel intronic nucleotide change c.288+9C>T within the BCKDHA gene: understanding a variant presentation of maple syrup urine disease. J Inherit Metab Dis. Dec. 2010;33 Suppl 3:S191-8. doi: 10.1007/s10545-010-9077-7. Epub Apr. 30, 2010.
Wang et al., 505. Developing AAV-Mediated Clinically Translatable Gene Therapy for Maple Syrup Urine Disease (MSUD) Caused by BCKDHA Mutations in a Bovine Model. Mol Ther. The Journal of The American Society of Gene Therapy; 22nd Annual Meeting of The American Society of Gene And Cell Therapy (ASGCT). Apr. 2019; 27(4S1): 238-239.
Extended European Search Report for Application No. 22796569.6, mailed Mar. 24, 2025.
Knerr et al., Advances and challenges in the treatment of branched-chain amino/keto acid metabolic defects. J Inherit Metab Dis. Jan. 2012;35(1):29-40. doi: 10.1007/s10545-010-9269-1. Epub Feb. 3, 2011.
Strauss et al., Branched-chain α-ketoacid dehydrogenase deficiency (maple syrup urine disease): Treatment, biomarkers, and outcomes. Mol Genet Metab. Mar. 2020;129(3):193-206. doi: 10.1016/j.ymgme.2020.01.006. Epub Jan. 16, 2020.

* cited by examiner

FIG. 1A

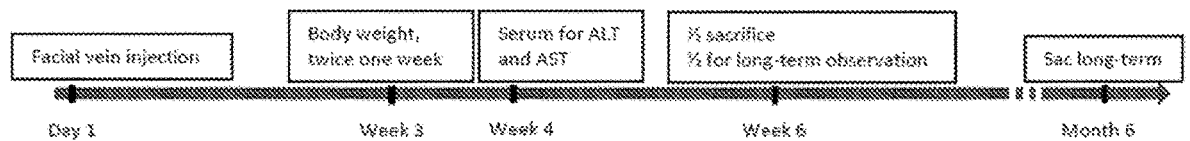
FIG. 4A
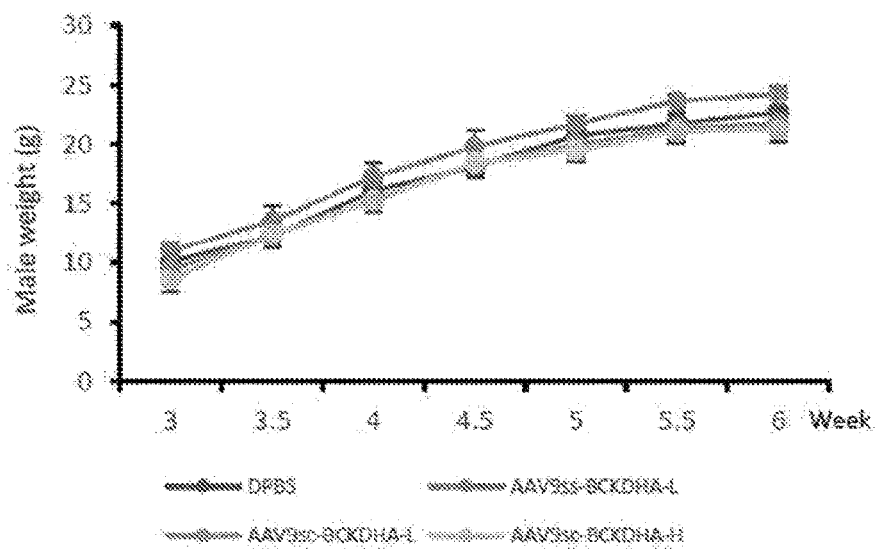
FIG. 4B
FIG. 4C

AAV-MEDIATED GENE THERAPY FOR MAPLE SYRUP URINE DISEASE (MSUD)

CROSS-REFERENCE TO RELATED APPLICATIONS

This application is a national stage filing under 35 U.S.C. § 371 of international PCT application PCT/US2020/027622, filed Apr. 10, 2020, which claims priority under 35 U.S.C. § 119(e) to U.S. provisional application, U.S. Ser. No. 62/930,687, filed Nov. 5, 2019 and U.S. provisional patent application, U.S. Ser. No. 62/833,159, filed Apr. 12, 2019, the entire contents of each of which are incorporated herein by reference.

BACKGROUND OF INVENTION

Maple syrup urine disease (MSUD) is a rare genetic disorder affecting degradation of the branched-chain amino acids (BCAA; leucine, isoleucine, and valine) and their ketoacid derivatives. It is caused by biallelic mutations in one of three genes that encode subunits of the branched-chain ketoacid dehydrogenase complex (BCKDHA, BCKDHB, and DBT). Severe (i.e., classical) MSUD is fatal without treatment. Dietary BCAA restriction is the mainstay of treatment but is difficult to implement, has imperfect efficacy, and affords no protection against episodic and life-threatening encephalopathic crises. Liver transplantation is an effective alternative to dietary therapy, but entails risks of surgery and long-term immunosuppression.

SUMMARY OF INVENTION

According to some aspects, the disclosure provides compositions and method for promoting expression of functional BCKDHA protein, which is the E1-alpha subunit of the branched-chain alpha-keto acid (BCAA) dehydrogenase complex, in a subject. In some embodiments, the methods involve administering to the subject an effective amount of a recombinant Adeno-associated virus (rAAV) comprising a capsid containing a nucleic acid engineered to express BCKDHA in the liver and/or skeletal muscle of a subject. In some embodiments, the subject comprises at least one endogenous BCKDHA allele having a loss-of-function mutation associated with MSUD. In some embodiments, the disclosure provides methods of treating a subject having MSUD that involve administering to the subject an effective amount of an rAAV comprising a capsid containing a nucleic acid engineered to express BCKDHA. In some embodiments, the nucleic acid expresses BCKDHA in the liver and/or skeletal muscle of the subject.

In some embodiments, the endogenous BCKDHA allele comprises a T-A transversion, resulting in a tyr394-to-asn (TYR394ASN). In some embodiments, the endogenous BCKDHA allele comprises a splice site mutation, a missense mutation, a truncation mutation or a nonsense mutation. In some embodiments, the endogenous BCKDHA alleles having the same loss-of-function mutations (homozygous state). In some embodiments, the endogenous BCKDHA alleles having different loss-of-function mutations (compound heterozygous state). In some embodiments, the endogenous BCKDHA allele comprises a 8-bp deletion (887_894del). In some embodiments, the endogenous BCKDHA allele comprises a 895G-A transition in exon 7, resulting in a gly245-to-arg (G245R) substitution. In some embodiments, the endogenous BCKDHA allele comprises a 1253T-G transversion, resulting in a phe364-to-cys (F364C) substitution. In some embodiments, the endogenous BCKDHA allele comprises a C-to-T transition resulting in an arg220-to-trp (R220W) substitution. In some embodiments, the endogenous BCKDHA allele comprises a G-to-A transition resulting in a gly204-to-ser (G204S) substitution. In some embodiments, the endogenous BCKDHA allele comprises a C-to-G transversion resulting in a thr265-to-arg (T265R) substitution. In some embodiments, the endogenous BCKDHA allele comprises a C-to-G transversion in the BCKDHA gene, resulting in a cys219-to-trp (C219W) substitution. In some embodiments, the endogenous BCKDHA allele comprises a 1-bp deletion (117delC), resulting in a frameshift, encoding a truncated protein with only 61 residues.

According to some aspects, the disclosure provides compositions and method for promoting expression of functional BCKDHB protein, which is the E1-beta subunit of the BCAA dehydrogenase complex, in a subject. In some embodiments, the methods involve administering to the subject an effective amount of an rAAV comprising a capsid containing a nucleic acid engineered to express BCKDHB in the liver and/or skeletal muscle of a subject. In some embodiments, the subject comprises at least one endogenous BCKDHB allele having a loss-of-function mutation associated with MSUD. In some embodiments, the disclosure provides methods of treating a subject having MSUD that involve administering to the subject an effective amount of an rAAV comprising a capsid containing a nucleic acid engineered to express BCKDHB. In some embodiments, the nucleic acid expresses BCKDHB in the liver and/or skeletal muscle of the subject.

In some embodiments, the endogenous BCKDHB allele comprises a splice site mutation, a missense mutation, a truncation mutation or a nonsense mutation. In some embodiments, the at least one endogenous BCKDHB allele comprises, an 11 base pair deletion in exon 1. In some embodiments, the at least one endogenous BCKDHB allele comprises, a guanine (G) to cytosine (C) change in exon 5, resulting in an arginine-to-proline substitution at residue 183 (R183P). In some embodiments, the at least one endogenous BCKDHB allele comprises, a C to thymine (T) transition, resulting in a histidine-to-tyrosine substitution at residue 156 (H156Y). In some embodiments, the at least one endogenous BCKDHB allele comprises, a T to G transversion, resulting in a valine-to-glycine substitution at residue 69 (V69G). In some embodiments, the at least one endogenous BCKDHB allele comprises, a 4 base pair deletion in intron 9 resulting in the deletion of exon 10, and an 8 base pair insertion in exon 10 resulting in a frameshift. In some embodiments, the at least one endogenous BCKDHB allele comprises, an 8 base pair insertion in exon 10.

According to some aspects, the disclosure provides compositions and method for promoting expression of functional BCKDHA and BCKDHB proteins, which are, respectively, the E1-alpha and E1-beta subunits of the BCAA dehydrogenase complex, in a subject. In some embodiments, the methods involve administering to the subject an effective amount of an rAAV comprising a capsid containing a nucleic acid engineered to express BCKDHA and BCKDHB in the liver and/or skeletal muscle of a subject. In some embodiments, the subject comprises at least one endogenous BCKDHA and/or BCKDHB allele having a loss-of-function mutation associated with MSUD. In some embodiments, the disclosure provides methods of treating a subject having MSUD that involve administering to the subject an effective amount of an rAAV comprising a capsid containing a nucleic acid engineered to express BCKDHA and BCKDHB. In some embodiments, the nucleic acid expresses BCKDHA and BCKDHB in the liver and/or skeletal muscle of the subject.

In some embodiments, the administration used in the methods described herein is systemic injection.

In some embodiments, the nucleic acids of the disclosure are engineered to express a codon-optimized human BCKDHA gene (opti-BCKDHA). In some embodiments, the nucleic acid comprises a sequence as set forth in any one of SEQ ID NO: 1-3. In some embodiments, the nucleic acids of the disclosure are engineered to express a codon-optimized human BCKDHB gene (opti-BCKDHB). In some embodiments, the nucleic acid comprises a sequence as set forth in any one of SEQ ID NO: 4-6. In some embodiments, the nucleic acids of the disclosure are engineered to express a codon-optimized human BCKDHA gene (opti-BCKDHA) and a codon-optimized human BCKDHB gene (opti-BCKDHB). In some embodiments, the nucleic acid comprises a sequence as set forth in any one of SEQ ID NO: 7-8.

In some embodiments, the nucleic acids of the disclosure comprise one or more adeno-associated virus (AAV) inverted terminal repeats (ITRs), wherein each ITR is selected from the group consisting of AAV1 ITR, AAV2 ITR, AAV3 ITR, AAV4 ITR, AAV5 ITR, and AAV6 ITR.

In some embodiments, the nucleic acid is a self-complementary AAV vector.

In an aspect, the disclosure relates to a method of treating a subject having Maple Syrup Urine Disease (MSUD), the method comprising administering to the subject an effective amount of an rAAV comprising a capsid containing a nucleic acid engineered to express BCKDHA in the liver and/or skeletal muscle of the subject.

In an aspect, the disclosure relates to an rAAV comprising an AAV9 capsid containing a nucleic acid engineered to express BCKDHA in the liver and/or skeletal muscle of the subject.

In some embodiments, the disclosure relates to a pharmaceutical composition comprising any of the rAAVs as disclosed herein.

In some embodiments, the disclosure relates to an isolated nucleic acid comprising a sequence as set forth by SEQ ID NO: 1 to 8.

In some embodiments, the disclosure relates to a host cell comprising any of the isolated nucleic acids disclosed herein. In some embodiments, the host cell is a eukaryotic cell.

In some embodiments, the disclosure relates to an isolated nucleic acid encoding an AAV capsid protein. In some embodiments, the capsid protein is AAV9 capsid protein.

These and other aspects and embodiments will be described in greater detail herein. The description of some exemplary embodiments of the disclosure are provided for illustration purposes only and not meant to be limiting. Additional compositions and methods are also embraced by this disclosure.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, Drawings, Examples, and Claims.

BRIEF DESCRIPTION OF THE DRAWINGS

Figure 1A:
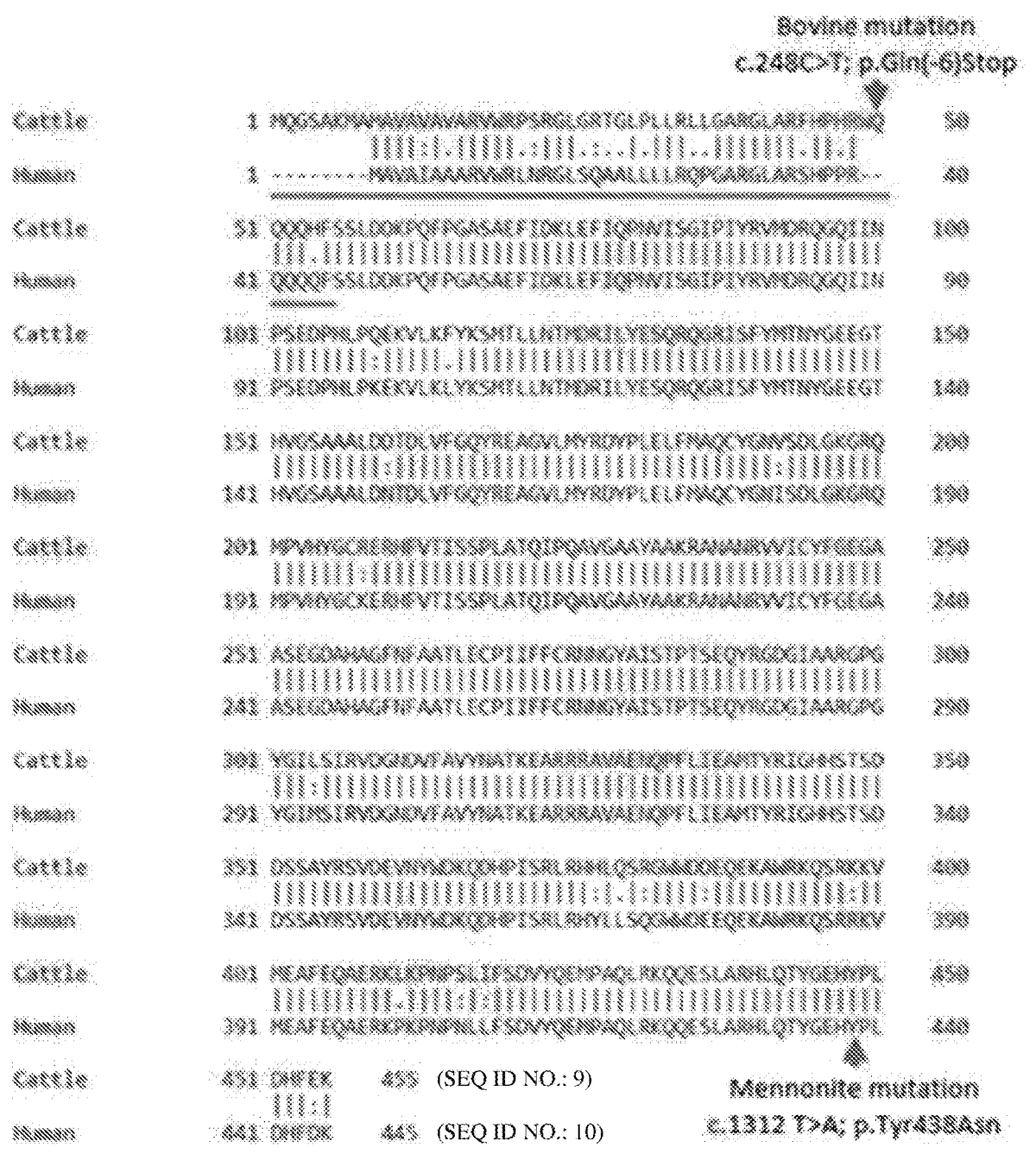

FIGS. 1A-1C show AAV-constructs expressing BCKDHA and their expression in HEK 293T cells. FIG. 1A: Amino acids sequence alignment of human and bovine BCKDHA proteins. Arrowheads indicate mutations in the bovine model and Mennonite patients, respectively. Underline highlights signal peptide of BCKDHA protein. FIG. 1B: Cartoons showing two constructs expressing the same codon-optimized human BCKDHA complementary DNA (cDNA) in single-stranded and self-complementary forms, respectively. FIG. 1C: Western blot showing endogenous and AAV-borne BCKDHA protein in HEK293T cells.

FIG. 2A: Schematics showing two constructs expressing the same codon-optimized human BCKDHB cDNA in single strand and self-complementary forms respectively. FIG. 2B: schematics showing two constructs expressing BCKDHA-BCKDHB cDNAs at the same time in single strand form. The upper panel using T2A sequence to link the two gene cassettes. The lower panel using bi-directional promoters sharing one common enhancer to drive the expression of two genes.

FIG. 3A: Western blot showing endogenous and AAV-constructs expressed BCKDHA and BCKDHB protein in wild-type (WT) and BCKDHA knock-out (KO) HEK 293T cells. BCKDHA vectors co-expressed with BCKDHB or alone are shown. BCKDHB could stabilize BCKDHA when co-expressed. FIG. 3B: BCKDC enzyme activity of WT and BCKDHA KO HEK 293T cells transfected with different AAV-constructs expressing BCKDHA or/and BCKDHB protein. BCKDC enzyme activity could be restored more efficiently when BCKDHA and BCKDHB were co-expressed in BCKDHA KO HEK 293T cells.

FIGS. 4A-4F show in vivo safety test of AAV-constructs expressing BCKDHA. FIG. 4A: Scheme of in vivo safety and efficiency test of AAV vectors delivery in WT mice. FIG. 4B: Injection dose of AAV vectors expressing BCKDHA. FIG. 4C: Male mice body weight curve with different doses injection. FIG. 4D: Female mice body weight curve with different doses injection. FIG. 4E: ALT test of mice with different doses injection. FIG. 4F: AST test of mice with different doses injection.

DETAILED DESCRIPTION OF INVENTION

Figure 1B:
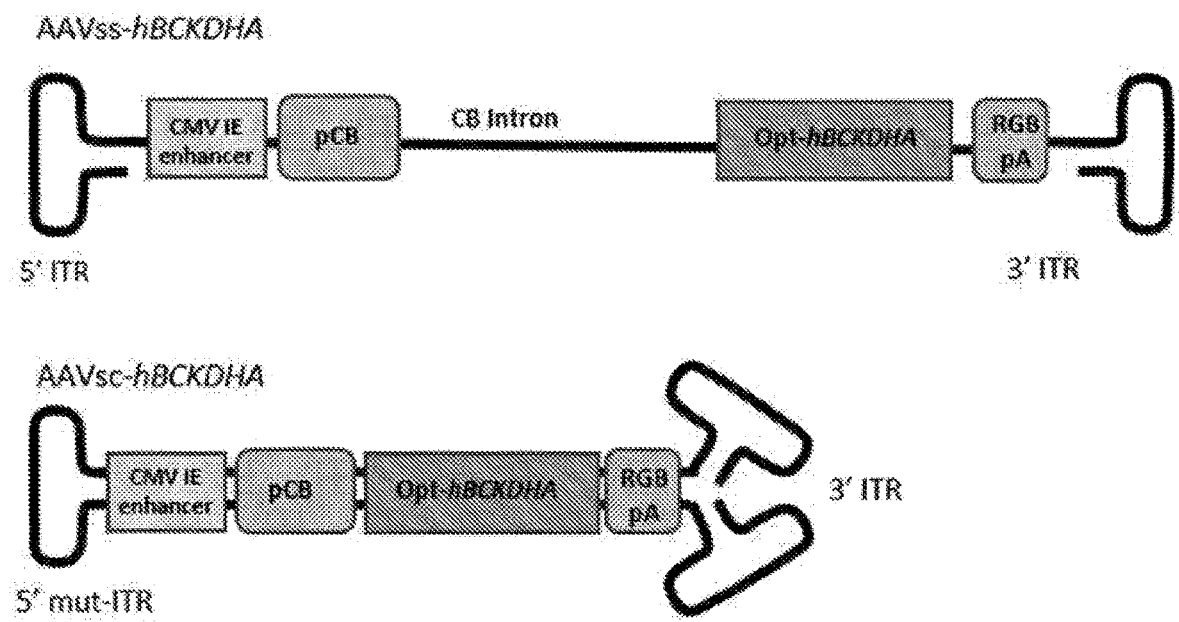

In some aspects, the disclosure relates to AAV-mediated gene replacement therapy for Maple Syrup Urine Disease (MSUD) caused by BCKDHA biallellic mutations. In some embodiments, AAV vectors are provided expressing a codon-optimized human BCKDHA gene (opti-BCKDHA), for which validated protein expression has been shown in various cell lines (e.g., Example 1). In some embodiments, an opti-BCKDHA cassette packaged into an rAAV comprising an AAV9 capsid. In some embodiments, the rAAV was delivered via systemic injection, and efficiently targets the liver and skeletal muscle, tissues which exhibit high levels of BCKDHA expression. In some embodiments, compared to these existing treatments, BCKDHA gene replacement therapy is as disclosed herein is a safer and more efficient option to treat MSUD.

In some embodiments, the endogenous BCKDHA allele comprises a T-A transversion, resulting in a tyr394-to-asn (TYR394ASN). In some embodiments, the endogenous BCKDHA allele comprises a splice site mutation, a missense mutation, a truncation mutation or a nonsense mutation. In some embodiments, the endogenous BCKDHA alleles having the same loss-of-function mutations (homozygous state). In some embodiments, the endogenous BCKDHA alleles having different loss-of-function mutations (compound heterozygous state). In some embodiments, the endogenous BCKDHA allele comprises a 8-bp deletion (887_894del). In some embodiments, the endogenous BCKDHA allele comprises a 895G-A transition in exon 7, resulting in a gly245-to-arg (G245R) substitution. In some embodiments, the endogenous BCKDHA allele comprises a 1253T-G transversion, resulting in a phe364-to-cys (F364C) substitution. In some embodiments, the endogenous BCKDHA allele comprises a C-to-T transition resulting in an arg220-to-trp (R220W) substitution. In some embodiments, the endogenous BCKDHA allele comprises a G-to-A transition resulting in a gly204-to-ser (G204S) substitution. In some embodiments, the endogenous BCKDHA allele comprises a C-to-G transversion resulting in a thr265-to-arg (T265R) substitution. In some embodiments, the endogenous BCKDHA allele comprises a C-to-G transversion in the BCKDHA gene, resulting in a cys219-to-trp (C219W) substitution. In some embodiments, the endogenous BCKDHA allele comprises a 1-bp deletion (117delC), resulting in a frameshift, encoding a truncated protein with only 61 residues.

In some aspects, the disclosure relates to AAV-mediated gene replacement therapy for MSUD caused by BCKDHB biallellic mutations. In some embodiments, AAV vectors are provided expressing a codon-optimized human BCKDHB gene (opti-BCKDHB), for which validated protein expression has been shown in various cell lines (e.g., Example 2). In some embodiments, an opti-BCKDHB cassette packaged into an rAAV comprising an AAV9 capsid. In some embodiments, the rAAV was delivered via systemic injection, and efficiently targets the liver and skeletal muscle, tissues which exhibit high levels of BCKDHB expression. In some embodiments, compared to these existing treatments, BCKDHB gene replacement therapy is as disclosed herein is a safer and more efficient option to treat MSUD.

In some embodiments, the endogenous BCKDHB allele comprises a splice site mutation, a missense mutation, a truncation mutation or a nonsense mutation. In some embodiments, the at least one endogenous BCKDHB allele comprises, an 11 base pair deletion in exon 1. In some embodiments, the at least one endogenous BCKDHB allele comprises, a guanine (G) to cytosine (C) change in exon 5, resulting in an arginine-to-proline substitution at residue 183 (R183P). In some embodiments, the at least one endogenous BCKDHB allele comprises, a C to thymine (T) transition, resulting in a histidine-to-tyrosine substitution at residue 156 (H156Y). In some embodiments, the at least one endogenous BCKDHB allele comprises, a T to G transversion, resulting in a valine-to-glycine substitution at residue 69 (V69G). In some embodiments, the at least one endogenous BCKDHB allele comprises, a 4 base pair deletion in intron 9 resulting in the deletion of exon 10, and an 8 base pair insertion in exon 10 resulting in a frameshift. In some embodiments, the at least one endogenous BCKDHB allele comprises, an 8 base pair insertion in exon 10.

In some aspects, the disclosure relates to AAV-mediated gene replacement therapy for MSUD caused by BCKDHA and/or BCKDHB biallellic mutations. In some embodiments, AAV vectors are provided expressing a codon-optimized human BCKDHA gene (opti-BCKDHA) and/or a codon-optimized human BCKDHB gene (opti-BCKDHB), for which validated protein expressions has been shown in various cell lines (e.g., Example 2). In some embodiments, an opti-BCKDHA and opti-BCKDHB cassette packaged into an rAAV comprising an AAV9 capsid. In some embodiments, the rAAV was delivered via systemic injection, and efficiently targets the liver and skeletal muscle, tissues which exhibit high levels of BCKDHA and/or BCKDHB expression. In some embodiments, compared to these existing treatments, the BCKDHA and BCKDHB gene replacement therapy, as disclosed herein, is a safer and more efficient option to treat MSUD.

Isolated Nucleic Acids

In some aspects, the disclosure provides a nucleic acid comprising at least one transgene operably linked to a promoter, wherein the transgene encodes BCKDHA (branched chain keto acid dehydrogenase E1, alpha polypeptide; GENE ID: 593).

The BCKDHA gene encodes the E1-alpha subunit of the branched-chain alpha-keto acid (BCAA) dehydrogenase complex (BCKD; EC 1.2.4.4), an inner-mitochondrial enzyme complex that catalyzes the oxidative decarboxylation of the branched-chain alpha-ketoacids derived from isoleucine, leucine, and valine. This reaction is the second major step in the catabolism of the branched-chain amino acids. The BCKD complex consists of three catalytic components: a heterotetrameric (alpha2-beta2) branched-chain alpha-keto acid decarboxylase (E1), a homo-24-meric dihydrolipoyl transacylase (E2; 248610), and a homodimeric dihydrolipoamide dehydrogenase (E3; 238331). E1 is a thiamine pyrophosphate (TPP)-dependent enzyme. The reaction is irreversible and constitutes the first committed step in BCAA oxidation. The BCKDHB gene (248611) encodes the beta subunit of E1. The complex also contains 2 regulatory enzymes, a kinase and a phosphorylase.

The BCKDHA gene may encode an mRNA having the nucleotide sequence of NM_000709.4 or NM_001164783.1. The BCKDHA gene may encode a protein having the amino acid sequence NP_000700.1 or NP_001158255.1. In some embodiments, the opti-BCKDHA transgene comprises the sequence according to SEQ ID NO: 1. In some embodiments, the opti-BCKDHA transgene comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 1. The terms "percent identity," "sequence identity," "% identity," "% sequence identity," and % identical," as they may be interchangeably used herein, refer to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category. Percent identity can be determined using the algorithms of Karlin and Altschul, Proc. Natl. Acad. Sci. USA 87:2264-68, 1990, modified as in Karlin and Altschul, Proc. Natl. Acad. Sci. USA 90:5873-77, 1993. Such algorithms is incorporated into the NBLAST and XBLAST programs (version 2.0) of Altschul et al., J. Mol. Biol. 215:403-10, 1990. BLAST protein searches can be performed with the XBLAST program, score=50, word length=3, to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (i.e., 0.1%), hundredths of a percent (i.e., 0.01%), etc.).

In some aspects, the disclosure provides a nucleic acid comprising at least one transgene operably linked to a promoter, wherein the transgene encodes BCKDHB (branched chain keto acid dehydrogenase E1, beta polypeptide; GENE ID: 594).

The BCKDHB gene encodes the E1-beta subunit of the branched-chain alpha-keto acid BCAA. The BCKDHB gene encodes the beta subunit of E1.

The BCKDHB gene may encode an mRNA having the nucleotide sequence of NM_000056.4, NM_001318975.1, or NM_183050.4. The BCKDHB gene may encode a protein having the amino acid sequence NP_000047.1, NP_898871.1, or NP_001305904.1. In some embodiments, the opti-BCKDHB transgene comprises the sequence according to SEQ ID NO: 4. In some embodiments, the opti-BCKDHB transgene comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 4.

A transgene which encodes a protein is generally operably linked to a promoter. As used herein, "operably linked" sequences include both expression control sequences that are contiguous with the gene of interest (e.g., transgene) and expression control sequences that act in trans or at a distance to control the gene of interest (e.g., transgene). In some embodiments, the promoter is a constitutive promoter, for example a chicken beta-actin (CBA) promoter, a retroviral Rous sarcoma virus (RSV) long terminal repeat (LTR) promoter (optionally with the RSV enhancer), a cytomegalovirus (CMV) promoter (optionally with the CMV enhancer) [see, e.g., Boshart et al., Cell, 41:521-530 (1985)], a Simian vacuolating virus 40 (SV40) promoter, a dihydrofolate reductase promoter, a beta-actin promoter, a phosphoglycerol kinase (PGK) promoter, and a EF1alpha promoter [Invitrogen]. In some embodiments, a promoter is an enhanced chicken beta-actin promoter. In some embodiments, a promoter is a U6 promoter.

In some embodiments, a promoter is an inducible promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268: 1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene (e.g., BCKDHA, BCKDHB) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the promoter drives transgene expression in neuronal tissues. In some embodiments, the disclosure provides a nucleic acid operably comprising a tissue-specific promoter operably linked to a transgene. As used herein, "tissue-specific promoter" refers to a promoter that preferentially regulates (e.g., drives or up-regulates) gene expression in a particular cell type relative to other cell types. A cell-type-specific promoter can be specific for any cell type, such as liver cells (e.g., hepatocytes), heart cells, muscle cells, etc.

Further examples of tissue-specific promoters include but are not limited to a liver-specific thyroxin binding globulin (TBG) promoter, an insulin promoter, a creatine kinase (MCK) promoter, an alpha-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998), and the immunoglobulin heavy chain promoter, among others which will be apparent to the skilled artisan.

In some aspects, the disclosure relates to isolated nucleic acids comprising a transgene (e.g., BCKDHA, BCKDHB) operably linked to a promoter via a chimeric intron. In some embodiments, a chimeric intron comprises a nucleic acid sequence from a chicken beta-actin gene, for example a non-coding intronic sequence from intron 1 of the chicken beta-actin gene. In some embodiments, the intronic sequence of the chicken beta-actin gene ranges from about 50 to about 150 nucleotides in length (e.g., any length between 50 and 150 nucleotides, inclusive). In some embodiments, the intronic sequence of the chicken beta-actin gene ranges from about 100 to 120 (e.g., 100, 101, 102, 103, 104, 105, 106, 107, 108, 109, 110, 111, 112, 113, 114, 115, 116, 117, 118, 119, or 120) nucleotides in length. In some embodiments, a chimeric intron is adjacent to one or more untranslated sequences (e.g., an untranslated sequence located between the promoter sequence and the chimeric intron sequence and/or an untranslated sequence located between the chimeric intron and the first codon of the transgene sequence). In some embodiments, each of the one or more untranslated sequences are non-coding sequences from a rabbit beta-globulin gene (e.g., untranslated sequence from rabbit beta-globulin exon 1, exon 2, etc.).

Recombinant AAVs

The isolated nucleic acids of the disclosure may be recombinant Adeno-associated viral (rAAVs) vectors. In some embodiments, an isolated nucleic acid as described by the disclosure comprises a region (e.g., a first region) comprising a first adeno-associated virus (AAV) inverted terminal repeat (ITR), or a variant thereof and a second region comprising a first transgene encoding BCKDHA or BCKDHAB. In some embodiments, the second region comprises a first transgene encoding BCKDHA. In some embodiments, the second region comprises a first transgene encoding BCKDHB. In some embodiments, the isolated nucleic acid further comprises a third region comprising a second transgene, which may or may not be different than the first transgene. In some embodiments, the second region comprises a first transgene encoding BCKDHA and a third region comprises a second transgene encoding a second gene of interest (e.g., transgene). In some embodiments, the second region comprises a first transgene encoding BCKDHB and a third region comprises a second transgene encoding a second gene of interest (e.g., transgene). In some embodiments, the second region and third region each comprise the transgene encoding BCKDHA. In some embodiments, the second region and third region each comprise the transgene encoding BCKDHB. In some embodiments, the second region comprises a first transgene encoding BCKDHA and a third region comprises a second transgene encoding BCKDHB. In some embodiments, the second region comprises a first transgene encoding BCKDHB and a third region comprises a second transgene encoding BCKDHA. The isolated nucleic acid (e.g., the rAAV vector) may be packaged into a capsid protein and administered to a subject and/or delivered to a selected target cell. The transgene may also comprise a region encoding, for example, a protein and/or an expression control sequence (e.g., a poly-A tail), as described elsewhere in the disclosure.

The instant disclosure provides a vector comprising a single, cis-acting WT ITR. In some embodiments, the ITR is a 5' ITR. In some embodiments, the ITR is a 3' ITR Generally, ITR sequences are about 145 bp in length. Preferably, substantially the entire sequences encoding the ITR(s) is used in the molecule, although some degree of minor modification of these sequences is permissible. In some embodiments, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. Adeno-associated viral ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, and/or AAVrh10 ITR sequence.

In some embodiments, an rAAV vector (e.g., pJW1-pAAV.pCB-CBA-opt-hBCKDHA-1) comprises a nucleic acid sequence according to SEQ ID NO: 2, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 2.

In some embodiments, an rAAV vector is a self-complementary vector (e.g., pJW2-pAAVsc.CB6-opt-hBCKDHA-1) that comprises a nucleic acid sequence according to SEQ ID NO: 3, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 3.

In some embodiments, an rAAV vector (e.g., pJW152-pAAV.pCB-CBA-opt-hBCKDHB) comprises a nucleic acid sequence according to SEQ ID NO: 5, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 5.

In some embodiments, an rAAV vector is a self-complementary vector (e.g., pJW153-pAAVsc.CB6-opt-hBCKDHB) that comprises a nucleic acid sequence according to SEQ ID NO: 6, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 62.

In some embodiments, an rAAV vector (e.g., pJW154-pAAV-pCB-opt-BCKDHB-T2A-opt-BCKDHA-1) comprises a nucleic acid sequence according to SEQ ID NO: 7, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 7.

In some embodiments, an rAAV vector is a self-complementary vector (e.g., pJW162-SURE\Cell-pAAV-SV40-opti-BCKDHA-BiCB6-opti-BCKDHB-RBG) that comprises a nucleic acid sequence according to SEQ ID NO: 8, or a portion thereof. In some embodiments, the rAAV vector comprises a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 8.

The isolated nucleic acids and/or rAAVs of the present disclosure may be modified and/or selected to enhance the targeting of the isolated nucleic acids and/or rAAVs to a target tissue (e.g., liver or skeletal muscle). Non-limiting methods of modifications and/or selections include AAV capsid serotypes (e.g., AAV9), tissue-specific promoters, and/or targeting peptides. In some embodiments, the isolated nucleic acids and rAAVs of the present disclosure comprise AAV capsid serotypes with enhanced targeting to liver or skeletal muscle tissues (e.g., AAV9). In some embodiments, the isolated nucleic acids and rAAVs of the present disclosure comprise tissue-specific promoters. In some embodiments, the isolated nucleic acids and rAAVs of the present disclosure comprise AAV capsid serotypes with enhanced targeting to liver or skeletal muscle tissues and tissue-specific promoters.

In some aspects, the disclosure provides isolated AAVs. As used herein with respect to AAVs, the term "isolated" refers to an AAV that has been artificially obtained or produced. Isolated AAVs may be produced using recombinant methods. Such AAVs are referred to herein as "recombinant AAVs" or "rAAVs." Recombinant AAVs preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, the rAAV comprises an AAV1, AAV2, AAV3, AAV4, AAV5, AAV6, AAV7, AAV8, AAVrh8, AAV9, AAV10 or AAVrh10 capsid protein, or a protein having substantial homology thereto. In some embodiments, the rAAV comprises an AAV9 capsid protein.

In some embodiments, the rAAVs of the disclosure are pseudo-typed rAAVs. Pseudo-typing is the process of producing viruses or viral vectors in combination with foreign viral envelope proteins. The result is a pseudo-typed virus particle. With this method, the foreign viral envelope proteins can be used to alter host tropism or an increased/decreased stability of the virus particles. In some aspects, a pseudo-typed rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudo-typed rAAV refers to an AAV comprising an inverted terminal repeats (ITRs) of one AAV serotype and an capsid protein of a different AAV serotype. For example, a pseudo-typed AAV vector containing the ITRs of serotype X encapsidated with the proteins of Y will be designated as AAVX/Y (e.g., AAV2/1 has the ITRs of AAV2 and the capsid of AAV1). In some embodiments, pseudo-typed rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining rAAVs having a desired capsid protein are well known in the art. (See, for example, US Patent Application Publication Number US 2003/0138772, the contents of which are incorporated herein by reference in their entirety). Typically the methods involve culturing a host cell which contains a nucleic acid sequence encoding an AAV capsid protein or fragment thereof; a functional rep gene; an rAAV vector composed of, AAV inverted terminal repeats (ITRs) and a transgene; and sufficient helper functions to permit packaging of the rAAV vector into the AAV capsid proteins. Typically, capsid proteins are structural proteins encoded by the cap gene of an AAV. In some embodiments, AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, capsid proteins protect a viral genome, deliver a genome and/or interact with a host cell. In some aspects, capsid proteins deliver the viral genome to a host in a tissue specific manner.

In some embodiments, the AAV capsid protein is of an AAV serotype selected from the group consisting of AAV3, AAV4, AAV5, AAV6, AAV8, AAVrh8 AAV9, AAV10 and AAVrh10. In some embodiments, the AAV capsid protein is of an AAVrh8 or AAVrh10 serotype. In some embodiments, the AAV capsid protein is of an AAVrh8 serotype.

In some embodiments, components to be cultured in the host cell to package an rAAV vector in an AAV capsid may be provided to the host cell in trans. Alternatively, any one or more of the required components (e.g., rAAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence selected from the group consisting of: SEQ ID NO: 1-8 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 1-8 operably linked to a promoter. In some embodiments, the disclosure relates to a host cell containing a nucleic acid that comprises a coding sequence selected from the group consisting of: SEQ ID NO: 1 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 1 operably linked to a promoter. In some embodiments, the disclosure relates to a host cell containing a nucleic acid that comprises a coding sequence selected from the group consisting of: SEQ ID NO: 2 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 2 operably linked to a promoter. In some embodiments, the disclosure relates to a host cell containing a nucleic acid that comprises a coding sequence selected from the group consisting of: SEQ ID NO: 3 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 3 operably linked to a promoter. In some embodiments, the disclosure relates to a host cell containing a nucleic acid that comprises a coding sequence selected from the group consisting of: SEQ ID NO: 4 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 4 operably linked to a promoter. In some embodiments, the disclosure relates to a host cell containing a nucleic acid that comprises a coding sequence selected from the group consisting of: SEQ ID NO: 5 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 5 operably linked to a promoter. In some embodiments, the disclosure relates to a host cell containing a nucleic acid that comprises a coding sequence selected from the group consisting of: SEQ ID NO: 6 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 6 operably linked to a promoter. In some embodiments, the disclosure relates to a host cell containing a nucleic acid that comprises a coding sequence selected from the group consisting of: SEQ ID NO: 7 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 7 operably linked to a promoter. In some embodiments, the disclosure relates to a host cell containing a nucleic acid that comprises a coding sequence selected from the group consisting of: SEQ ID NO: 8 that is operably linked to a promoter. In some embodiments, the disclosure relates to a host cell containing a nucleic acid comprising a sequence having at least 80% identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity or more) to SEQ ID NO: 8 operably linked to a promoter.

In some embodiments, the disclosure relates to a composition comprising the host cell described above. In some embodiments, the composition comprising the host cell above further comprises a cryopreservative.

The rAAV vector, rep sequences, cap sequences, and helper functions useful for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions (i.e., infectious viral particle) are well known and the selection of a suitable method is not a limitation on the present disclosure. See, e.g., K. Fisher et al., J. Virol., 70:520-532 (1993) and U.S. Pat. No. 5,478,745.

In some embodiments, rAAVs may be produced using the triple transfection method (described in detail in U.S. Pat. No. 6,001,650). Typically, the rAAVs are produced by transfecting a host cell with an rAAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable WT AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced through the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of rAAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the term "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

The isolated nucleic acids of the present disclosure may be rAAV vectors. Recombinant AAV vectors of the disclosure are typically composed of, at a minimum, a transgene and its regulatory sequences, and 5' and 3' AAV ITRs. It is this rAAV vector which is packaged into a capsid protein and delivered to a selected target cell. In some embodiments, the transgene is a nucleic acid sequence, heterologous to the vector sequences, which encodes a polypeptide, protein, functional RNA molecule or other gene product, of interest. The nucleic acid coding sequence is operatively linked to regulatory components in a manner which permits transgene transcription, translation, and/or expression in a cell of a target tissue.

Aspects of the disclosure relate to the discovery that modifying the regulatory sequences of rAAVs provides levels of transgene expression that are therapeutically effective yet do not cause the vector-mediated toxicity associated with previously used rAAVs. Accordingly, in some embodiments, the disclosure relates to an rAAV comprising modified genetic regulatory elements. In some embodiments, the modified genetic regulatory element is a hybrid promoter.

As used herein, the term "hybrid promoter" refers to a regulatory construct capable of driving transcription an RNA transcript (e.g., a transcript comprising encoded by a transgene) in which the construct comprises two or more regulatory elements artificially arranged. Typically, a hybrid promoter comprises at least one element that is a minimal promoter and at least one element having an enhancer sequence or an intronic, exonic, or untranslated region (UTR) sequence comprising one or more transcriptional regulatory elements. In embodiments in which a hybrid promoter comprises an exonic, intronic, or UTR sequence, such sequence(s) may encode upstream portions of the RNA transcript while also containing regulatory elements that modulate (e.g., enhance) transcription of the transcript. In some embodiments, two or more elements of a hybrid promoter are from heterologous sources relative to one another. In some embodiments, two or more elements of a hybrid promoter are from heterologous sources relative to the transgene. In some embodiments, two or more elements of a hybrid promoter are from different genetic loci. In some embodiments, two or more elements of a hybrid promoter are from the same genetic locus but are arranged in a manner not found at the genetic locus. In some embodiments, the hybrid promoter comprise a first nucleic acid sequence from one promoter fused to one or more nucleic acid sequences comprises promoter or enhancer elements of a difference source. In some embodiments, a hybrid promoter comprises a first sequence from the chicken beta-actin promoter and a second sequence of the CMV enhancer. In some embodiments, a hybrid promoter comprises a first sequence from a chicken beta-actin promoter and a second sequence from an intron of a chicken-beta actin gene. In some embodiments, a hybrid promoter comprises a first sequence from the chicken beta-actin promoter fused to a CMV enhancer sequence and a sequence from an intron of the chicken-beta actin gene.

In some aspects, the rAAV comprises an enhancer element. As used herein, the term "enhancer element" refers to a nucleic acid sequence that when bound by an activator protein, activates or increases transcription of a gene or genes. Enhancer sequences can be upstream (i.e., 5') or downstream (i.e., 3') relative to the genes they regulate. Examples of enhancer sequences include cytomegalovirus (CMV) enhancer sequence and the SV40 enhancer sequence. In some embodiments, rAAVs comprise a CMV enhancer element or a portion thereof. As used herein, the term "a portion thereof" refers to a fragment of a nucleotide or amino acid sequence that retains the desired functional characteristic of the entire nucleotide or amino acid sequence from which it is derived. For example, a "CMV enhancer sequence or a portion thereof" refers to a nucleotide sequence derived from WT CMV enhancer that is capable of increasing transcription of a transgene.

In some aspects, the rAAV comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE).

In some aspects, the disclosure provides rAAV vectors comprising a hybrid or chimeric intron. As used herein, the term "chimeric intron" refers an intron having sequences from two or more different sources. In some embodiments, a chimeric intron comprises a nucleic acid encoding a splice donor site from a first source (e.g., organism or species) and a splice acceptor site from a second source (e.g., organism or species). In some embodiments, a chimeric intron comprise one or more transcriptional regulatory elements and/or enhancer sequences. In some embodiments, a chimeric intron is positioned between an exon of a hybrid promoter and transgene. In some embodiments, the disclosure provides an rAAV comprising a promoter operably linked to a transgene, wherein the transgene encodes a BCKDHA protein, and wherein the rAAV further comprises a chimeric intron. In some embodiments, the disclosure provides an rAAV comprising a promoter operably linked to a transgene, wherein the transgene encodes a BCKDHB protein, and wherein the rAAV further comprises a chimeric intron. In some embodiments, the disclosure provides an rAAV comprising a promoter operably linked to a first transgene, wherein the transgene encodes a BCKDHA protein and a second transgene wherein the transgene encodes a BCKDHB protein, and wherein the rAAV further comprises a chimeric intron.

In certain embodiments, the disclosure relates to rAAV vectors comprising artificial transcription elements. As used here, the term "artificial transcription element" refers, in some embodiments, to a synthetic sequence enabling the controlled transcription of DNA by an RNA polymerase to produce an RNA transcript. Transcriptionally active elements of the present disclosure are generally smaller than 500 bp, preferably smaller than 200 bp, more preferably smaller than 100, most preferably smaller than 50 bp. In some embodiments, an artificial transcription element comprises two or more nucleic acid sequences from transcriptionally active elements. Transcriptionally active elements are generally recognized in the art and include, for example, promoter, enhancer sequence, TATA box, G/C box, CCAAT box, specificity protein 1 (Sp1) binding site, Inr region, CRE (cAMP regulatory element), activating transcription factor 1 (ATF1) binding site, ATF1-CRE binding site, APBbeta box, APBalpha box, CArG box, CCAC box and those disclosed by U.S. Pat. No. 6,346,415. Combinations of the foregoing transcriptionally active elements are also contemplated.

In some embodiments, the artificial transcription element comprises promoter sequence. In some embodiments, the artificial transcription element comprises enhancer sequence. In some embodiments, the artificial transcription element comprises ATF1-CRE binding site. In some embodiments, the artificial transcription element comprises SP1 binding site. In some embodiments, the artificial transcription element comprises C box. In some embodiments, the artificial transcription element comprises TATA box. In some embodiments, the artificial transcription element comprises ATF1-CRE binding site, SP1 binding site and TATA box.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. An rAAV construct useful in the present disclosure may also contain an intron, desirably located between the promoter/enhancer sequence and the transgene. One possible intron sequence is derived from SV-40, and is referred to as the SV-40 T intron sequence.

Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the beta-actin promoter, the phosphoglycerol kinase (PGK) promoter, and the EF1alpha promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, the rAAVs of the disclosure are pseudo-typed rAAVs. For example, a pseudo-typed AAV vector containing the ITRs of serotype X encapsidated with the proteins of Y will be designated as AAVX/Y (e.g., AAV2/1 has the ITRs of AAV2 and the capsid of AAV1). In some embodiments, pseudo-typed rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the rAAV vector, the vector also includes conventional control elements necessary which are operably linked to the transgene in a manner which permits its transcription, translation and/or expression in a cell transfected with the plasmid vector or infected with the virus produced by the disclosure.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein. In another example, the transgene encodes a protein that is intended to be used for research purposes, e.g., to create a somatic transgenic animal model harboring the transgene, e.g., to study the function of the transgene product. In another example, the transgene encodes a protein that is intended to be used to create an animal model of disease.

In some embodiments, the disclosure provides an rAAV comprising a transgene encoding BCKDHA. In some embodiments, the disclosure provides an rAAV comprising a transgene encoding BCKDHB. In some embodiments, the disclosure provides and rAAV comprising more than one transgene. In some embodiments, the rAAV comprises transgenes encoding BCKDHA and BCKDHB. Also contemplated herein are methods of treating MSUD by delivering a transgene to a subject using the rAAVs described herein. In some embodiments, the disclosure provides an rAAV comprising a transgene encoding BCKDHB. Also contemplated herein are methods of treating MSUD by delivering a transgene to a subject using the rAAVs described herein. Also contemplated herein are methods of treating MSUD by delivering a transgene to a subject using the rAAVs described herein. In some embodiments, the disclosure relates to a method for treating a MSUD, the method comprising administering an rAAV to a subject. In some embodiments, the rAAV comprises a hybrid promoter. In some embodiments, the rAAV comprises a chimeric intron. In some embodiments, the rAAV comprises an artificial transcription element. In some embodiments, the artificial transcription element comprises ATF1-CRE binding site, SP1 binding site and TATA box. In some embodiments, the promoter, chimeric intron or artificial transcription element is operably linked to a transgene. In some embodiments, the transgene encodes BCKDHA. In some embodiments, the transgene encodes BCKDHB. In some embodiments, transgenes encode BCKDHA and BCKDHB.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject (i.e., host animal (e.g., human, mouse, rat, cat, dog, sheep, rabbit, horse, cow, goat, pig, guinea pig, hamster, chicken, turkey, or a non-human primate (e.g., Macaque))). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue.

Aspects of the disclosure relate to compositions comprising an rAAV comprising at least one modified genetic regulatory sequence or element. In some embodiments, the composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some aspects, the disclosure relates to a composition (e.g., a pharmaceutical composition) comprising an rAAV comprising a nucleic acid encoding a BCKDHA. In some aspects, the disclosure relates to a composition (e.g., a pharmaceutical composition) comprising an rAAV comprising a nucleic acid encoding a BCKDHB. In some aspects, the disclosure relates to a composition (e.g., a pharmaceutical composition) comprising an rAAV comprising a nucleic acid encoding BCKDHA and BCKDHB.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Recombinant AAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., injection into the liver, skeletal muscle), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine an rAAV virion dose range to treat a patient having a particular disease or disorder based on the aforementioned factors, as well as other factors that are well known in the art.

The terms "effective amount," "therapeutically effective amount," and "pharmaceutically effective amount," as may be used interchangeably herein, refer to an amount of a biologically active agent (e.g., the isolated nucleic acids, rAAV, compositions of the present disclosure) sufficient to elicit a desired response. The effective amount will depend primarily on factors such as the species, age, weight, health of the subject, and the tissue to be targeted, and may thus vary among animal and tissue. For example, an effective amount of the rAAV is generally in the range from about 1 ml to about 100 ml of solution containing from about $10^6$ to $10^{16}$ genome copies (e.g., from $1 \times 10^6$ to $1 \times 10^{16}$, inclusive). In some cases, a dosage between about $10^{11}$ to $10^{12}$ rAAV genome copies is appropriate. In some embodiments, a dosage of between about $10^{11}$ to $10^{13}$ rAAV genome copies is appropriate. In some embodiments, a dosage of between about $10^{11}$ to $10^{14}$ rAAV genome copies is appropriate. In some embodiments, a dosage of between about $10^{11}$ to $10^{15}$ rAAV genome copies is appropriate. In some embodiments, a dosage of $4.68 \times 10^7$ is appropriate. In some embodiments, a dosage of $4.68 \times 10^8$ genome copies is appropriate. In some embodiments, a dosage of $4.68 \times 10^9$ genome copies is appropriate. In some embodiments, a dosage of $1.17 \times 10^{10}$ genome copies is appropriate. In some embodiments, a dosage of $2.34 \times 10^{10}$ genome copies is appropriate. In some embodiments, a dosage of $3.20 \times 10^{11}$ genome copies is appropriate. In some embodiments, a dosage of $1.2 \times 10^{13}$ genome copies is appropriate. In some embodiments, a dosage of about $1 \times 10^{14}$ vector genome (vg) copies is appropriate.

In some aspects, the disclosure relates to the recognition that one potential side-effect for administering an AAV to a subject is an immune response in the subject to the AAV, including inflammation. In some embodiments, a subject is immunosuppressed prior to administration of one or more rAAVs as described herein.

As used herein, "immunosuppressed" or "immunosuppression" refers to a decrease in the activation or efficacy of an immune response in a subject. Immunosuppression can be induced in a subject using one or more (e.g., multiple, such as 2, 3, 4, 5, or more) agents, including, but not limited to, rituximab, methylprednisolone, prednisolone, sirolimus, immunoglobulin injection, prednisone, methotrexate, and any combination thereof.

In some embodiments, methods described by disclosure further comprise the step inducing immunosuppression (e.g., administering one or more immunosuppressive agents) in a subject prior to the subject being administered an rAAV (e.g., an rAAV or pharmaceutical composition as described by the disclosure). In some embodiments, a subject is immunosuppressed (e.g., immunosuppression is induced in the subject) between about 30 days and about 0 days (e.g., any time between 30 days until administration of the rAAV, inclusive) prior to administration of the rAAV to the subject. In some embodiments, the subject is pre-treated with immune suppression (e.g., rituximab, sirolimus, and/or prednisone) for at least 7 days.

In some embodiments, immunosuppression of a subject maintained during and/or after administration of an rAAV or pharmaceutical composition. In some embodiments, a subject is immunosuppressed (e.g., administered one or more immunosuppressants) for between 1 day and 1 year after administration of the rAAV or pharmaceutical composition.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. See, e.g., Wright F R, et al., Molecular Therapy (2005) 12, 171-178, the contents of which are incorporated herein by reference.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515; and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Angstroms, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

In some embodiments, the disclosure relates to administration of one or more additional therapeutic agents to a subject who has been administered an rAAV or pharmaceutical composition as described herein.

Kits and Related Compositions

The agents (e.g., nucleic acids, rAAV, vectors, etc.) described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit for producing an rAAV, the kit comprising a container housing an isolated nucleic acid having a sequence of any one of SEQ ID NO: 1-8. In some embodiments, the kit further comprises instructions for producing the rAAV. In some embodiments, the kit further comprises at least one container housing an rAAV vector, wherein the rAAV vector comprises a transgene.

In some embodiments, the disclosure relates to a kit comprising a container housing an rAAV as described supra. In some embodiments, the kit further comprises a container housing a pharmaceutically acceptable carrier. For example, a kit may comprise one container housing an rAAV and a second container housing a buffer suitable for injection of the rAAV into a subject. In some embodiments, the container is a syringe.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or intravenous (iv) needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a WT adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to WT adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package rAAV vectors, using methods well known in the art, to determine functional characteristics associated with the novel capsid protein encoded by the gene. For example, novel isolated capsid genes can be used to construct and package rAAV vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

Methods of Treating Maple Syrup Urine Disease (MSUD)

Aspects of the present disclosure provide methods for treating a MSUD. MSUD caused by: a mutation in the E1-alpha subunit gene is referred to as MSUD "type IA;" caused by a mutation in the E1-beta subunit gene as "type IB;" and that caused by defect in the E2 subunit gene as "type II." In some embodiments, clinical features of MSUD are mental and physical retardation, feeding problems, and a maple syrup odor to the urine. In some embodiments, keto acids of branched-chain amino acids are present in urine, resulting from a block in oxidative decarboxylation.

Accordingly, in some embodiments, the disclosure provides isolated nucleic acids, rAAVs, compositions, and methods useful in treating MSUD. The terms "treatment," "treat," and "treating," as may be used interchangeably herein, refer to a clinical intervention aimed to reverse, alleviate, delay the onset of, or inhibit the progress of a, indication, disease, disorder, or one or more symptoms thereof, as described herein (e.g., MSUD). In some embodiments, treatment may be administered after one or more symptoms have developed and/or after a disease has been diagnosed. In other embodiments, treatment may be administered in the absence of symptoms (e.g., to prevent or delay onset of a symptom or inhibit onset or progression of a disease). For example, treatment may be administered to a susceptible individual (e.g., subject) prior to the onset of symptoms (e.g., in light of a history of symptoms and/or in light of genetic or other susceptibility factors). Treatment may also be continued after symptoms have resolved, for example, to prevent or delay their recurrence.

In some aspects, the disclosure relates to a method for promoting expression of functional BCKDHA protein, which is the E1-alpha subunit of the branched-chain alpha-keto acid (BCAA) dehydrogenase complex, in a subject, the method comprising administering to the subject an effective amount of an rAAV comprising a capsid containing a nucleic acid engineered to express BCKDHA in the liver and/or skeletal muscle of the subject, wherein the subject comprises at least one endogenous BCKDHA allele having a loss-of-function mutation associated with Maple Syrup Urine Disease (MSUD). In some embodiments, the isolated nucleic acids, rAAVs, compositions, and methods are for the treatment of MSUD. In some embodiments, MSUD in a subject may be the result of at least one endogenous BCKDHA allele having a loss-of-function mutation associated with Maple Syrup Urine Disease (MSUD).

In some embodiments, the at least one endogenous BCKDHA allele comprises a T-A transversion, resulting in a tyr394-to-asn (TYR394ASN). In some embodiments, the at least one endogenous BCKDHA allele comprises a splice site mutation, a missense mutation, a truncation mutation, or a nonsense mutation. In some embodiments, the endogenous BCKDHA allele comprises a 8 base pair deletion (887_894del). In some embodiments, the endogenous BCKDHA allele comprises a 895G-A transition in exon 7, resulting in a gly245-to-arg (G245R) substitution. In some embodiments, the endogenous BCKDHA allele comprises a 1253T-G transversion, resulting in a phe364-to-cys (F364C) substitution. In some embodiments, the endogenous BCKDHA allele comprises a C-to-T transition resulting in an arg220-to-trp (R220W) substitution. In some embodiments, the endogenous BCKDHA allele comprises a G-to-A transition resulting in a gly204-to-ser (G204S) substitution. In some embodiments, the endogenous BCKDHA allele comprises a C-to-G transversion resulting in a thr265-to-arg (T265R) substitution. In some embodiments, the endogenous BCKDHA allele comprises a C-to-G transversion in the BCKDHA gene, resulting in a cys219-to-trp (C219W) substitution. In some embodiments, the endogenous BCKDHA allele comprises a 1 base pair deletion (117delC), resulting in a frameshift, encoding a truncated protein with only 61 residues.

In some embodiments, the subject has two endogenous BCKDHA alleles having the same loss-of-function mutations (homozygous state). In some embodiments, the subject has two endogenous BCKDHA alleles having different loss-of-function mutations (compound heterozygous state).

A method for promoting expression of functional BCKDHB protein, which is the E1-beta subunit of the branched-chain alpha-keto acid (BCAA) dehydrogenase complex, in a subject, the method comprising administering to the subject an effective amount of an rAAV comprising a capsid containing a nucleic acid engineered to express BCKDHB in the liver and/or skeletal muscle of the subject, wherein the subject comprises at least one endogenous BCKDHB allele having a loss-of-function mutation associated with Maple Syrup Urine Disease (MSUD). In some embodiments, MSUD in a subject may be the result of at least one endogenous BCKDHB allele having at least one endogenous BCKDHB allele having a loss-of-function mutation associated with Maple Syrup Urine Disease (MSUD).

In some embodiments, the at least one endogenous BCKDHB allele comprises, an 11 base pair deletion in exon 1. In some embodiments, the at least one endogenous BCKDHB allele comprises, a guanine (G) to cytosine (C) change in exon 5, resulting in an arginine-to-proline substitution at residue 183 (R183P). In some embodiments, the at least one endogenous BCKDHB allele comprises, a C to thymine (T) transition, resulting in a histidine-to-tyrosine substitution at residue 156 (H156Y). In some embodiments, the at least one endogenous BCKDHB allele comprises, a T to G transversion, resulting in a valine-to-glycine substitution at residue 69 (V69G). In some embodiments, the at least one endogenous BCKDHB allele comprises, a 4 base pair deletion in intron 9 resulting in the deletion of exon 10, and an 8 base pair insertion in exon 10 resulting in a frameshift. In some embodiments, the at least one endogenous BCKDHB allele comprises, an 8 base pair insertion in exon 10. In some embodiments, the at least one endogenous BCKDHB allele comprises a splice site mutation, a missense mutation, a truncation mutation, or a nonsense mutation. In some embodiments, the subject has two endogenous BCKDHB alleles having the same loss-of-function mutations (homozygous state). In some embodiments, the subject has two endogenous BCKDHB alleles having different loss-of-function mutations (compound heterozygous state).

Methods for treating MSUD in a subject may comprise administering an isolated nucleic acid, rAAV, or composition of the present disclosure that comprises a transgene encoding BCKDHA. In some embodiments, the method (e.g., administration of the isolated nucleic acid, rAAV, or compositions of the present disclosure) increases the expression of functional BCKDKA in a subject. In some embodiments, the method (e.g., administration of the isolated nucleic acid, rAAV, or compositions of the present disclosure) increases the functional expression of BCKDKA at least 10%, at least 20%, at least 30%, at least 40%, at least 50%, at least 60%, at least 70%, at least 80%, at least 90% or more, in a subject (e.g., relative to the subject prior to administration of the rAAV). In some embodiments, the method (e.g., administration of the isolated nucleic acid, rAAV, or compositions of the present disclosure) increases the degradation of the branched-chain amino acids (BCAA; leucine, isoleucine, and valine) and their ketoacid derivatives. In some embodiments, the method (e.g., administration of the isolated nucleic acid, rAAV, or compositions of the present disclosure) increases the degradation of the branched-chain amino acids (BCAA; leucine, isoleucine, and valine) and their ketoacid derivatives at least 10%, at least 20%, at least 30%, at least 40%, at least 50%, at least 60%, at least 70%, at least 80%, at least 90% or more, in a subject (e.g., relative to the subject prior to administration of the rAAV).

Methods for treating MSUD in a subject may comprise administering an isolated nucleic acid, rAAV, or composition of the present disclosure that comprises a transgene encoding BCKDHB. In some embodiments, the method (e.g., administration of the isolated nucleic acid, rAAV, or compositions of the present disclosure) increases the expression of functional BCKDKB in a subject. In some embodiments, the method (e.g., administration of the isolated nucleic acid, rAAV, or compositions of the present disclosure) increases the functional expression of BCKDKB at least 10%, at least 20%, at least 30%, at least 40%, at least 50%, at least 60%, at least 70%, at least 80%, at least 90% or more, in a subject (e.g., relative to the subject prior to administration of the rAAV). In some embodiments, the method (e.g., administration of the isolated nucleic acid, rAAV, or compositions of the present disclosure) increases the degradation of the branched-chain amino acids (BCAA; leucine, isoleucine, and valine) and their ketoacid derivatives (e.g., relative to the subject prior to administration of the rAAV). In some embodiments, the method (e.g., administration of the isolated nucleic acid, rAAV, or compositions of the present disclosure) increases the degradation of the branched-chain amino acids (BCAA; leucine, isoleucine, and valine) and their ketoacid derivatives at least 10%, at least 20%, at least 30%, at least 40%, at least 50%, at least 60%, at least 70%, at least 80%, at least 90% or more, in a subject (e.g., relative to the subject prior to administration of the rAAV).

In some embodiments, the method (e.g., administration of the isolated nucleic acid, rAAV, or compositions of the present disclosure) reduce the ratio of leucine to alanine. In some embodiments, the method (e.g., administration of the isolated nucleic acid, rAAV, or compositions of the present disclosure) reduce the ratio of leucine to alanine by at least 10%, at least 20%, at least 30%, at least 40%, at least 50%, at least 60%, at least 70%, at least 80%, at least 90% or more, in a subject (e.g., relative to the subject prior to administration of the rAAV). In some embodiments, the method (e.g., administration of the isolated nucleic acid, rAAV, or compositions of the present disclosure) reduce the ratio of leucine to alanine to 0.4 or less. In some embodiments, the method (e.g., administration of the isolated nucleic acid, rAAV, or compositions of the present disclosure) reduce urine branched-chain α-ketoacids (BCKA): 2-oxoisocaproate, 2-oxo-3-methylvalerate, 2-oxoisovalerate, 2-hydroxyisovalerate, 2-hydroxyisocaproate, and/or 2-hydroxy-3-methylvalerate.

A subject may be a human, a mouse, a rat, a pig, a dog, a cat, cattle, or a non-human primate. In some embodiments, the subject is a human. Administering means contacting a cell or subject with an isolated nucleic acid, rAAV, or composition of the present disclosure. Non-limiting examples of administering including intravenous injection, intraarterial injection, intracranial injection, intrathecal injection, intracerebral injection, infusion, or inhalation.

Exemplary Sequences

This Table exhibits some exemplary sequences as disclosed by the instant Specification, but is not limiting. This Specification includes a Sequence Listing submitted concurrently herewith as a text file in ASCII format. The Sequence Listing and all of the information contained therein are expressly incorporated herein and constitute part of the instant Specification as filed.

TABLE 1

Exemplary Sequences

| SEQ ID NO. | Sequence* | Description |
| --- | --- | --- |
| 1 | ATGGCCGTCGCAATCGCCGCCGCAAGAGTGTGGAGACTGAATCGGGGACTG<br>AGCCAGGCCGCACTGCTGCTGCTGAGACAGCCAGGAGCCAGAGGCCTGGCC<br>AGGAGCCACCCACCTAGGCAGCAGCAGCAGTTCAGCTCCCTGGACGATAAG<br>CCACAGTTTCCCGGCGCCTCTGCCGAGTTCATCGACAAGCTGGAGTTTATC<br>CAGCCAAACGTGATCAGCGGCATCCCCATCTACCGCGTGATGGACCGGCAG<br>GGCCAGATCATCAATCCATCCGAGGACCCCACCTGCCAAAGGAGAAGGTG<br>CTGAAGCTGTACAAGTCTATGACCCTGCTGAACACAATGGATAGAATCCTG<br>TATGAGTCCCAGCGCCAGGGCCGGATCTCTTTCTACATGACCAACTATGGC<br>GAGGAGGGCACACACGTGGGCAGCGCCGCCGCCCTGGACAATACCGATCTG<br>GTGTTCGGCCAGTATAGAGAGGCCGGCGTGCTGATGTACAGGGACTATCCT<br>CTGGAGCTGTTTATGGCCCAGTGCTACGGCAATATCAGCGATCTGGGCAAG<br>GGCCGCCAGATGCCAGTGCACTATGGCTGTAAGGAGCGGCACTTCGTGACC<br>ATCTCTAGCCCCCTGGCCACACAGATCCCTCAGGCAGTGGGAGCAGCCTAC<br>GCCGCCAAGAGAGCCAACGCCAATAGGGTGGTCATCTGCTATTTTGGAGAG<br>GGAGCAGCCTCCGAGGGCGACGCACACGCCGGCTTCAACTTTGCCGCCACC<br>CTGGAGTGCCCTATCATCTTCTTTTGTAGAAACAATGGCTACGCCATCTCT<br>ACCCCAACAAGCGAGCAGTATAGGGGCGATGGAATCGCAGCCAGAGGCCCA<br>GGCTACGGCATCATGTCCATCAGGGTGGACGGCAACGACGTGTTCGCCGTG<br>TATAATGCCACAAAGGAGGCACGGAGAAGGGCAGTGGCAGAGAACCAGCCC<br>TTTCTGATCGAGGCCATGACCTACAGAATCGGCCACCACAGCACATCCGAC<br>GATTCCTCTGCCTACAGGTCTGTGGACGAAGTGAATTATTGGGACAAGCAG<br>GATCACCCTATCAGCAGACTGAGGCACTATCTGCTGTCCCAGGGCTGGTGG<br>GATGAGGAGCAGGAGAAGGCCTGGAGGAAGCAGAGCCGCCGGAAAGTGATG<br>GAGGCCTTCGAGCAGGCAGAGAGGAAGCCAAAGCCCAACCCTAATCTGCTG<br>TTTTCCGACGTGTACCAGGAGATGCCTGCCCAGCTGAGGAAGCAGCAGGAG<br>AGCCTGGCAAGACACCTGCAGACATACGGCGAGCATTACCCCCTGGACCAT<br>TTTGATAAGTGA | opti-BCKDHA |

TABLE 1 -continued

Exemplary Sequences

| SEQ ID NO. | Sequence* | Description |
|---|---|---|
| 2 | CGCGTGGTACCTCTAGAGTCGACCCGGGCGGCCTCGAGGACGGGGTGAACT<br>ACGCCTGAGGATCCGATCTTTTTCCCTCTGCCAAAAATTATGGGGACATCA<br>TGAAGCCCCTTGAGCATCTGACTTCTGGCTAATAAAGGAAATTTATTTTCA<br>TTGCAATAGTGTGTTGGAATTTTTTGTGTCTCTCACTCGGAAGCAATTCGT<br>TGATCTGAATTTCGACCACCCATAATACCCATTACCCTGGTAGATAAGTAG<br>CATGGCGGGTTAATCATTAACTACAAGGAACCCCTAGTGATGGAGTTGGCC<br>ACTCCCTCTCTGCGCGCTCGCTCGCTCACTGAGGCCGGGCGACCAAAGGTC<br>GCCCGACGCCCGGGCTTTGCCCGGGCGGCCTCAGTGAGCGAGCGAGCGCGC<br>AGCCTTAATTAACCTAATTCACTGGCCGTCGTTTTACAACGTCGTGACTGG<br>GAAAACCCTGGCGTTACCCAACTTAATCGCCTTGCAGCACATCCCCCTTTC<br>GCCAGCTGGCGTAATAGCGAAGAGGCCCGCACCGATCGCCCTTCCCAACAG<br>TTGCGCAGCCTGAATGGCGAATGGGACGCGCCCTGTAGCGGCGCATTAAGC<br>GCGGCGGGTGTGGTGGTTACGCGCAGCGTGACCGCTACACTTGCCAGCGCC<br>CTAGCGCCCGCTCCTTTCGCTTTCTTCCCTTCCTTTCTCGCCACGTTCGCC<br>GGCTTTCCCCGTCAAGCTCTAAATCGGGGGCTCCCTTTAGGGTTCCGATTT<br>AGTGCTTTACGGCACCTCGACCCCAAAAAACTTGATTAGGGTGATGGTTCA<br>CGTAGTGGGCCATCGCCCTGATAGACGGTTTTTCGCCCTTTGACGTTGGAG<br>TCCACGTTCTTTAATAGTGGACTCTTGTTCCAAACTGGAACAACACTCAAC<br>CCTATCTCGGTCTATTCTTTTGATTTATAAGGGATTTTGCCGATTTCGGCC<br>TATTGGTTAAAAAATGAGCTGATTTAACAAAAATTTAACGCGAATTTTAAC<br>AAAATATTAACGCTTACAATTTAGGTGGCACTTTTCGGGGAAATGTGCGCG<br>GAACCCCTATTTGTTTATTTTTCTAAATACATTCAAATATGTATCCGCTCA<br>TGAGACAATAACCCTGATAAATGCTTCAATAATATTGAAAAAGGAAGAGTA<br>TGAGTATTCAACATTTCCGTGTCGCCCTTATTCCCTTTTTTGCGGCATTTT<br>GCCTTCCTGTTTTTGCTCACCCAGAAACGCTGGTGAAAGTAAAAGATGCTG<br>AAGATCAGTTGGGTGCACGAGTGGGTTACATCGAACTGGATCTCAACAGCG<br>GTAAGATCCTTGAGAGTTTTCGCCCCGAAGAACGTTTTCCAATGATGAGCA<br>CTTTTAAAGTTCTGCTATGTGGCGCGGTATTATCCCGTATTGACGCCGGGC<br>AAGAGCAACTCGGTCGCCGCATACACTATTCTCAGAATGACTTGGTTGAGT<br>ACTCACCAGTCACAGAAAAGCATCTTACGGATGGCATGACAGTAAGAGAAT<br>TATGCAGTGCTGCCATAACCATGAGTGATAACACTGCGGCCAACTTACTTC<br>TGACAACGATCGGAGGACCGAAGGAGCTAACCGCTTTTTTGCACAACATGG<br>GGGATCATGTAACTCGCCTTGATCGTTGGGAACCGGAGCTGAATGAAGCCA<br>TACCAAACGACGAGCGTGACACCACGATGCCTGTAGCAATGGCAACAACGT<br>TGCGCAAACTATTAACTGGCGAACTACTTACTCTAGCTTCCCGGCAACAAT<br>TAATAGACTGGATGGAGGCGGATAAAGTTGCAGGACCACTTCTGCGCTCGG<br>CCCTTCCGGCTGGCTGGTTTATTGCTGATAAATCTGGAGCCGGTGAGCGTG<br>GGTCTCGCGGTATCATTGCAGCACTGGGGCCAGATGGTAAGCCCTCCCGTA<br>TCGTAGTTATCTACACGACGGGGAGTCAGGCAACTATGGATGAACGAAATA<br>GACAGATCGCTGAGATAGGTGCCTCACTGATTAAGCATTGGTAACTGTCAG<br>ACCAAGTTTACTCATATATACTTTAGATTGATTTAAAACTTCATTTTTAAT<br>TTAAAAGGATCTAGGTGAAGATCCTTTTTGATAATCTCATGACCAAAATCC<br>CTTAACGTGAGTTTTCGTTCCACTGAGCGTCAGACCCCGTAGAAAAGATCA<br>AAGGATCTTCTTGAGATCCTTTTTTTCTGCGCGTAATCTGCTGCTTGCAAA<br>CAAAAAAACCACCGCTACCAGCGGTGGTTTGTTTGCCGGATCAAGAGCTAC<br>CAACTCTTTTTCCGAAGGTAACTGGCTTCAGCAGAGCGCAGATACCAAATA<br>CTGTTCTTCTAGTGTAGCCGTAGTTAGGCCACCACTTCAAGAACTCTGTAG<br>CACCGCCTACATACCTCGCTCTGCTAATCCTGTTACCAGTGGCTGCTGCCA<br>GTGGCGATAAGTCGTGTCTTACCGGGTTGGACTCAAGACGATAGTTACCGG<br>ATAAGGCGCAGCGGTCGGGCTGAACGGGGGGTTCGTGCACACAGCCCAGCT<br>TGGAGCGAACGACCTACACCGAACTGAGATACCTACAGCGTGAGCTATGAG<br>AAAGCGCCACGCTTCCCGAAGGGAGAAAGGCGGACAGGTATCCGGTAAGCG<br>GCAGGGTCGGAACAGGAGAGCGCACGAGGGAGCTTCCAGGGGGAAACGCCT<br>GGTATCTTTATAGTCCTGTCGGGTTTCGCCACCTCTGACTTGAGCGTCGAT<br>TTTTGTGATGCTCGTCAGGGGGGCGGAGCCTATGGAAAAACGCCAGCAACG<br>CGGCCTTTTTACGGTTCCTGGCCTTTTGCTGGCCTTTTGCTCACATGTTCT<br>TTCCTGCGTTATCCCCTGATTCTGTGGATAACCGTATTACCGCCTTTGAGT<br>GAGCTGATACCGCTCGCCGCAGCCGAACGACCGAGCGCAGCGAGTCAGTGA<br>GCGAGGAAGCGGAAGAGCGCCCAATACGCAAACCGCCTCTCCCCGCGCGTT<br>GGCCGATTCATTAATGCAGCTGGCACGACAGGTTTCCCGACTGGAAAGCGG<br>GCAGTGAGCGCAACGCAATTAATGTGAGTTAGCTCACTCATTAGGCACCCC<br>AGGCTTTACACTTTATGCTTCCGGCTCGTATGTTGTGTGGAATTGTGAGCG<br>GATAACAATTTCACACAGGAAACAGCTATGACCATGATTACGCCAGATTTA<br>ATTAAGGCCTTAATTAGGCTGCGCGCTCGCTCGCTCACTGAGGCGCCCGG<br>GCAAAGCCCGGGCGTCGGGCGACCTTTGGTCGCCCGGCCTCAGTGAGCGAG<br>CGAGCGCGCAGAGAGGGAGTGGCCAACTCCATCACTAGGGGTTCCTTGTAG<br>TTAATGATTAACCCGCCATGCTACTTATCTACCAGGGTAATGGGGATCCTC<br>TAGAACTATAGCTAGTCGACATTGATTATTGACTAGTTATTAATAGTAATC<br>AATTACGGGGTCATTAGTTCATAGCCCATATATGGAGTTCCGCGTTACATA<br>ACTTACGGTAAATGGCCCGCCTGGCTGACCGCCCAACGACCCCCGCCCATT<br>GACGTCAATAATGACGTATGTTCCCATAGTAACGCCAATAGGGACTTTCCA<br>TTGACGTCAATGGGTGGAGTATTTACGGTAAACTGCCCACTTGGCAGTACA<br>TCAAGTGTATCATATGCCAAGTACGCCCCCTATTGACGTCAATGACGGTAA | rAAV vector: pJW1-pAAV.pCB-CBA-opt-hBCKDHA-1 |

TABLE 1 -continued

Exemplary Sequences

| SEQ ID NO. | Sequence* | Description |
|---|---|---|
| | ATGGCCCGCCTGGCATTATGCCCAGTACATGACCTTATGGGACTTTCCTAC<br>TTGGCAGTACATCTACGTATTAGTCATCGCTATTACCATGGTCGAGGTGAG<br>CCCCACGTTCTGCTTCACTCTCCCCATCTCCCCCCCCTCCCCACCCCCAAT<br>TTTGTATTTATTTATTTTTAATTATTTTGTGCAGCGATGGGGGCGGGGGG<br>GGGGGGGGGCGCGCGCCAGGCGGGGCGGGGCGGGGCGAGGGGCGGGGCGG<br>GGCGAGGCGGAGAGGTGCGGCGGCAGCCAATCAGAGCGGCGCGCTCCGAAA<br>GTTTCCTTTTATGGCGAGGCGGCGGCGGCGGCGGCCCTATAAAAAGCGAAG<br>CGCGCGGCGGGCGGGGAGTCGCTGCGACGCTGCCTTCGCCCCGTGCCCCGC<br>TCCGCCGCCGCCTCGCGCCGCCCGCCCCGGCTCTGACTGACCGCGTTACTC<br>CCACAGGTGAGCGGGCGGGACGGCCCTTCTCCTCCGGGCTGTAATTAGCGC<br>TTGGTTTAATGACGGCTTGTTTCTTTTCTGTGGCTGCGTGAAAGCCTTGAG<br>GGGCTCCGGGAGGGCCCTTTGTGCGGGGGAGCGGCTCGGGGGGTGCGTGC<br>GTGTGTGTGTGCGTGGGGAGCGCCGCGTGCGGCTCCGCGCTGCCCGGCGGC<br>TGTGAGCGCTGCGGGCGCGGCGCGGGGCTTTGTGCGCTCCGCAGTGTGCGC<br>GAGGGGAGCGCGGCCGGGGGCGGTGCCCCGCGGTGCGGGGGGCGTGCGAG<br>GGGAACAAAGGCTGCGTGCGGGTGTGTGCGTGGGGGGGTGAGCAGGGGGT<br>GTGGGCGCGTCGGTCGGGCTGCAACCCCCCTGCACCCCCTCCCCGAGTT<br>GCTGAGCACGCCCGGCTTCGGGTGCGGGCTCCGTACGGGGCGTGGCGCG<br>GGGCTCGCCGTGCCGGGCGGGGGTGGCGGCAGGTGGGGGTGCCGGGCGGG<br>GCGGGGCCGCCTCGGGCCGGGGAGGGCTCGGGGGAGGGGCGCGGCGGCCCC<br>CGGAGCGCCGGCGGCTGTCGAGGCGCGGCGAGCCGCAGCCATTGCCTTTTA<br>TGGTAATCGTGCGAGAGGGCGCAGGGACTTCCTTTGTCCCAAATCTGTGCG<br>GAGCCGAAATCTGGGAGGCGCCGCCGCACCCCCTCTAGCGGGCGCGGGGCG<br>AAGCGGTGCGGCGCCGGCAGGAAGGAAATGGGCGGGAGGGCCTTCGTGCG<br>TCGCCGCGCCGCCGTCCCCTTCTCCCTCTCCAGCCTCGGGGCTGTCCGCGG<br>GGGGACGGCTGCCTTCGGGGGGACGGGGCAGGGCGGGGTTCGGCTTCTGG<br>CGTGTGTGACCGGCGGCTCTAGAGCCTCTGCTAACCATGTTCATGCCTTCTTC<br>TTTTTCCTACAGCTCCTGGGCAACGTGCTGGTTATTGTGCTGTCTCATCAT<br>TTTGGCAAAGAATTCGCCACCATGGCCGTCGCAATCGCCGCCGAAGAGTG<br>TGGAGACTGAATCGGGGACTGAGCCAGGCCGCACTGCTGCTGCTGAGACAG<br>CCAGGAGCCAGAGGCCTGGCCAGGAGCCACCCACCTAGGCAGCAGCAGCAG<br>TTCAGCTCCCTGGACGATAAGCCACAGTTTCCCGGCGCCTCTGCCGAGTTC<br>ATCGACAAGCTGGAGTTTATCCAGCCAAACGTGATCAGCGGCATCCCCATC<br>TACCGCGTGATGGACCGGCAGGGCCAGATCATCAATCCATCCGAGGACCCC<br>CACCTGCCAAAGGAGAAGGTGCTGAAGCTGTACAAGTCTATGACCCTGCTG<br>AACACAATGGATAGAATCCTGTATGAGTCCCAGCGCCAGGGCCGGATCTCT<br>TTCTACATGACCAACTATGGCGAGGAGGGCACACACGTGGGCAGCGCCGCC<br>GCCCTGGACAATACCGATCTGGTGTTCGGCCAGTATAGAGAGGCCGGCGTG<br>CTGATGTACAGGGACTATCCTCTGGAGCTGTTTATGGCCCAGTGCTACGGC<br>AATATCAGCGATCTGGGCAAGGGCCGCCAGATGCCAGTGCACTATGGCTGT<br>AAGGAGCGGCACTTCGTGACCATCTCTAGCCCCCTGGCCACACAGATCCCT<br>CAGGCAGTGGGAGCAGCCTACGCCGCCAAGAGAGCCAACGCCAATAGGGTG<br>GTCATCTGCTATTTTGGAGAGGGAGCAGCCTCCGAGGGCGACGCACACGCC<br>GGCTTCAACTTTGCCGCCACCCTGGAGTGCCCTATCATCTTCTTTTGTAGA<br>AACAATGGCTACGCCATCTCTACCCCAACAAGCGAGCAGTATAGGGGCGAT<br>GGAATCGCAGCCAGAGGCCCAGGCTACGGCATCATGTCCATCAGGGTGGAC<br>GGCAACGACGTGTTCGCCGTGTATAATGCCACAAAGGAGGCACGGAGAAGG<br>GCAGTGGCAGAGAACCAGCCCTTTCTGATCGAGGCCATGACCTACAGAATC<br>GGCCACCACAGCACATCCGACGATTCCTCTGCCTACAGGTCTGTGGACGAA<br>GTGAATTATTGGGACAAGCAGGATCACCCTATCAGCAGACTGAGGCACTAT<br>CTGCTGTCCCAGGGCTGGTGGGATGAGGAGCAGGAGAAGGCCTGGAGGAAG<br>CAGAGCCGCCGGAAAGTGATGGAGGCCTTCGAGCAGGCAGAGAGGAAGCCA<br>AAGCCCAACCCTAATCTGCTGTTTTCCGACGTGTACCAGGAGATGCCTGCC<br>CAGCTGAGGAAGCAGCAGGAGAGCCTGGCAAGACACCTGCAGACATACGGC<br>GAGCATTACCCCCTGGACCATTTTGATAAGTGAA | |
| 3 | CTGCGCGCTCGCTCGCTCACTGAGGCCGCCCGGGCAAAGCCCGGGCGTCGG<br>GCGACCTTTGGTCGCCCGGCCTCAGTGAGCGAGCGAGCGCGCAGAGAGGGA<br>GTGTAGCCATGCTCTAGGAAGATCAATTCAATTCACGCGTCGACATTGATT<br>ATTGACTAGTTATTAATAGTAATCAATTACGGGGTCATTAGTTCATAGCCC<br>ATATATGGAGTTCCGCGTTACATAACTTACGGTAAATGGCCCGCCTGGCTG<br>ACCGCCCAACGACCCCCGCCCATTGACGTCAATAATGACGTATGTTCCCAT<br>AGTAACGCCAATAGGGACTTTCCATTGACGTCAATGGGTGGATATTTACGG<br>TAAACTGCCCACTTGGCAGTACATCAAGTGTATCATATGCCAAGTACGCCC<br>CCTATTGACGTCAATGACGGTAAATGGCCCGCCTGGCATTATGCCCAGTAC<br>ATGACCTTATGGGACTTTCCTACTTGGCAGTACATCTACGTATTAGTCATC<br>GCTATTACCATGTCGAGGCCACGTTCTGCTTCACTCTCCCCATCTCCCCCC<br>CCTCCCCACCCCCAATTTTGTATTTATTTATTTTTAATTATTTTGTGCAG<br>CGATGGGGGCGGGGGGGGGGGCGCGCGCCAGGCGGGGCGGGGCGGGGGCGA<br>GGGGCGGGGCGGGGCGAGGCGGAGAGGTGCGGCGGCAGCCAATCAGAGCGG<br>CGCGCTCCGAAAGTTTCCTTTTATGGCGAGGCGGCGGCGGCGGCGGCCCTA<br>TAAAAAGCGAAGCGCGCGGCGGGCGGGAGCAAGCTCTAGCCTCGAGGCCAC<br>CATGGCCGTCGCAATCGCCGCCGAAGAGTGTGGAGACTGAATCGGGGACT<br>GAGCCAGGCCGCACTGCTGCTGCTGAGACAGCCAGGAGCCAGAGGCCTGGC | rAAV<br>vector:<br>pJW2-<br>pAAVsc.<br>CB6-opt-<br>hBCKDHA-1 |

TABLE 1 -continued

Exemplary Sequences

| SEQ ID NO. | Sequence* | Description |
|---|---|---|
| | CAGGAGCCACCCACCTAGGCAGCAGCAGCAGTTCAGCTCCCTGGACGATAA<br>GCCACAGTTTCCCGGCGCCTCTGCCGAGTTCATCGACAAGCTGGAGTTTAT<br>CCAGCCAAACGTGATCAGCGGCATCCCCATCTACCGCGTGATGGACCGGCA<br>GGGCCAGATCATCAATCCATCCGAGGACCCCCACCTGCCAAAGGAGAAGGT<br>GCTGAAGCTGTACAAGTCTATGACCCTGCTGAACACAATGGATAGAATCCT<br>GTATGAGTCCCAGCGCCAGGGCCGGATCTCTTTCTACATGACCAACTATGG<br>CGAGGAGGGCACACACGTGGGCAGCGCCGCCGCCCTGGACAATACCGATCT<br>GGTGTTCGGCCAGTATAGAGAGGCCGGCGTGCTGATGTACAGGGACTATCC<br>TCTGGAGCTGTTTATGGCCCAGTGCTACGGCAATATCAGCGATCTGGGCAA<br>GGGCCGCCAGATGCCAGTGCACTATGGCTGTAAGGAGCGGCACTTCGTGAC<br>CATCTCTAGCCCCCTGGCCACACAGATCCCTCAGGCAGTGGGAGCAGCCTA<br>CGCCGCCAAGAGAGCCAACGCCAATAGGGTGGTCATCTGCTATTTTGGAGA<br>GGGAGCAGCCTCCGAGGGCGACGCACACGCCGGCTTCAACTTTGCCGCCAC<br>CCTGGAGTGCCCTATCATCTTCTTTTGTAGAAACAATGGCTACGCCATCTC<br>TACCCCAACAAGCGAGCAGTATAGGGGCGATGGAATCGCAGCCAGAGGCCC<br>AGGCTACGGCATCATGTCCATCAGGGTGGACGGCAACGACGTGTTCGCCGT<br>GTATAATGCCACAAAGGAGGCACGGAGAAGGGCAGTGGCAGAGAACCAGCC<br>CTTTCTGATCGAGGCCATGACCTACAGAATCGGCCACCACAGCACATCCGA<br>CGATTCCTCTGCCTACAGGTCTGTGGACGAAGTGAATTATTGGGACAAGCA<br>GGATCACCCTATCAGCAGACTGAGGCACTATCTGCTGTCCCAGGGCTGGTG<br>GGATGAGGAGCAGGAGAAGGCCTGGAGGAAGCAGAGCCGCCGGAAAGTGAT<br>GGAGGCCTTCGAGCAGGCAGAGAGGAAGCCAAAGCCCAACCCTAATCTGCT<br>GTTTTCCGACGTGTACCAGGAGATGCCTGCCCAGCTGAGGAAGCAGCAGGA<br>GAGCCTGGCAAGACACCTGCAGACATACGGCGAGCATTACCCCCTGGACCA<br>TTTTGATAAGTGAGGATCCGATCTTTTTCCCTCTGCCAAAAATTATGGGGA<br>CATCATGAAGCCCCTTGAGCATCTGACTTCTGGCTAATAAAGGAAATTTAT<br>TTTCATTGCAATAGTGTGTTGGAATTTTTTGTGTCTCTCACTCGGCCTAGG<br>TAGATAAGTAGCATGGCGGGTTAATCATTAACTACAAGGAACCCCTAGTGA<br>TGGAGTTGGCCACTCCCTCTCTGCGCGCTCGCTCGCTCACTGAGGCCGGGC<br>GACCAAAGGTCGCCCGACGCCCGGGCTTTGCCCGGGCGGCCTCAGTGAGCG<br>AGCGAGCGCGCAGCCTTAATTAACCTAATTCACTGGCCGTCGTTTTACAAC<br>GTCGTGACTGGGAAAACCCTGGCGTTACCCAACTTAATCGCCTTGCAGCAC<br>ATCCCCCTTTCGCCAGCTGGCGTAATAGCGAAGAGGCCCGCACCGATCGCC<br>CTTCCCAACAGTTGCGCAGCCTGAATGGCGAATGGGACGCGCCCTGTAGCG<br>GCGCATTAAGCGCGGCGGGTGTGGTGGTTACGCGCAGCGTGACCGCTACAC<br>TTGCCAGCGCCCTAGCGCCCGCTCCTTTCGCTTTCTTCCCTTCCTTTCTCG<br>CCACGTTCGCCGGCTTTCCCCGTCAAGCTCTAAATCGGGGGCTCCCTTTAG<br>GGTTCCGATTTAGTGCTTTACGGCACCTCGACCCCAAAAAACTTGATTAGG<br>GTGATGGTTCACGTAGTGGGCCATCGCCCTGATAGACGGTTTTTCGCCCTT<br>TGACGTTGGAGTCCACGTTCTTTAATAGTGGACTCTTGTTCCAAACTGGAA<br>CAACACTCAACCCTATCTCGGTCTATTCTTTTGATTTATAAGGGATTTTGC<br>CGATTTCGGCCTATTGGTTAAAAAATGAGCTGATTTAACAAAAATTTAACG<br>CGAATTTTAACAAAATATTAACGCTTACAATTTAGGTGGCACTTTTCGGGG<br>AAATGTGCGCGGAACCCCTATTTGTTTATTTTTCTAAATACATTCAAATAT<br>GTATCCGCTCATGAGACAATAACCCTGATAAATGCTTCAATAATATTGAAA<br>AAGGAAGAGTATGAGTATTCAACATTTCCGTGTCGCCCTTATTCCCTTTTT<br>TGCGGCATTTTGCCTTCCTGTTTTTGCTCACCCAGAAACGCTGGTGAAAGT<br>AAAAGATGCTGAAGATCAGTTGGGTGCACGAGTGGGTTACATCGAACTGGA<br>TCTCAACAGCGGTAAGATCCTTGAGAGTTTTCGCCCCGAAGAACGTTTTCC<br>AATGATGAGCACTTTTAAAGTTCTGCTATGTGGCGCGGTATTATCCCGTAT<br>TGACGCCGGGCAAGAGCAACTCGGTCGCCGCATACACTATTCTCAGAATGA<br>CTTGGTTGAGTACTCACCAGTCACAGAAAAGCATCTTACGGATGGCATGAC<br>AGTAAGAGAATTATGCAGTGCTGCCATAACCATGAGTGATAACACTGCGGC<br>CAACTTACTTCTGACAACGATCGGAGGACCGAAGGAGCTAACCGCTTTTTT<br>GCACAACATGGGGGATCATGTAACTCGCCTTGATCGTTGGGAACCGGAGCT<br>GAATGAAGCCATACCAAACGACGAGCGTGACACCACGATGCCTGTAGCAAT<br>GGCAACAACGTTGCGCAAACTATTAACTGGCGAACTACTTACTCTAGCTTC<br>CCGGCAACAATTAATAGACTGGATGGAGGCGGATAAAGTTGCAGGACCACT<br>TCTGCGCTCGGCCCTTCCGGCTGGCTGGTTTATTGCTGATAAATCTGGAGC<br>CGGTGAGCGTGGGTCTCGCGGTATCATTGCAGCACTGGGGCCAGATGGTAA<br>GCCCTCCCGTATCGTAGTTATCTACACGACGGGGAGTCAGGCAACTATGGA<br>TGAACGAAATAGACAGATCGCTGAGATAGGTGCCTCACTGATTAAGCATTG<br>GTAACTGTCAGACCAAGTTTACTCATATATACTTTAGATTGATTTAAAACT<br>TCATTTTTAATTTAAAAGGATCTAGGTGAAGATCCTTTTTGATAATCTCAT<br>GACCAAAATCCCTTAACGTGAGTTTTCGTTCCACTGAGCGTCAGACCCCGT<br>AGAAAAGATCAAAGGATCTTCTTGAGATCCTTTTTTTCTGCGCGTAATCTG<br>CTGCTTGCAAACAAAAAAACCACCGCTACCAGCGGTGGTTTGTTTGCCGGA<br>TCAAGAGCTACCAACTCTTTTTCCGAAGGTAACTGGCTTCAGCAGAGCGCA<br>GATACCAAATACTGTTCTTCTAGTGTAGCCGTAGTTAGGCCACCACTTCAA<br>GAACTCTGTAGCACCGCCTACATACCTCGCTCTGCTAATCCTGTTACCAGT<br>GGCTGCTGCCAGTGGCGATAAGTCGTGTCTTACCGGGTTGGACTCAAGACG<br>ATAGTTACCGGATAAGGCGCAGCGGTCGGGCTGAACGGGGGGTTCGTGCAC<br>ACAGCCCAGCTTGGAGCGAACGACCTACACCGAACTGAGATACCTACAGCG<br>TGAGCTATGAGAAAGCGCCACGCTTCCCGAAGGGAGAAAGGCGGACAGGTA | |

TABLE 1 -continued

Exemplary Sequences

| SEQ ID NO. | Sequence* | Description |
|---|---|---|
| | TCCGGTAAGCGGCAGGGTCGGAACAGGAGAGCGCACGAGGGAGCTTCCAGG GGGAAACGCCTGGTATCTTTATAGTCCTGTCGGGTTTCGCCACCTCTGACT TGAGCGTCGATTTTTGTGATGCTCGTCAGGGGGGCGGAGCCTATGGAAAAA CGCCAGCAACGCGGCCTTTTTACGGTTCCTGGCCTTTTGCTGGCCTTTTGC TCACATGTTCTTTCCTGCGTTATCCCCTGATTCTGTGGATAACCGTATTAC CGCCTTTGAGTGAGCTGATACCGCTCGCCGCAGCCGAACGACCGAGCGCAG CGAGTCAGTGAGCGAGGAAGCGGAAGAGCGCCCAATACGCAAACCGCCTCT CCCCGCGCGTTGGCCGATTCATTAATGCAGCTGGCACGACAGGTTTCCCGA CTGGAAAGCGGGCAGTGAGCGCAACGCAATTAATGTGAGTTAGCTCACTCA TTAGGCACCCCAGGCTTTACACTTTATGCTTCCGGCTCGTATGTTGTGTGG AATTGTGAGCGGATAACAATTTCACACAGGAAACAGCTATGACCATGATTA CGCCAGATTTAATTAAGGCCTTAATTAGG | |
| 4 | atgGCCGTGGTCGCTGCTGCTGCCGGATGGCTGCTGAGACTGCGGGCCGCT GGGGCTGAGGGACATTGGAGGAGACTGCCTGGGGCTGGGCTGGCAAGGGGC TTCCTGCACCCTGCAGCAACAGTGGAGGACGCAGCACAGCGGAGACAGGTG GCCCACTTCACCTTTCAGCCCGATCCTGAGCCACGCGAGTACGGCCAGACA CAGAAGATGAACCTGTTCCAGTCCGTGACCTCTGCCCTGGACAATAGCCTG GCCAAGGATCCAACAGCCGTGATCTTTGGCGAGGACGTGGCCTTCGGCGGC GTGTTTCGGTGCACAGTGGGCCTGAGAGACAAGTACGGCAAGGATCGGGTG TTCAACACCCCACTGTGCGAGCAGGGAATCGTGGGCTTTGGCATCGGCATC GCAGTGACCGGAGCAACAGCAATCGCAGAGATCCAGTTCGCCGACTATATC TTCCCCGCCTTTGATCAGATCGTGAACGAGGCCGCCAAGTACAGGTATCGC TCCGGCGACCTGTTTAATTGCGGCAGCCTGACCATCAGATCCCCTTGGGGA TGCGTGGGACACGGCGCCCTGTATCACTCTCAGAGCCCAGAGGCCTTCTTT GCCCACTGCCCCGGCATCAAGGTGGTCATCCCACGGAGCCCCTTCCAGGCA AAGGGCCTGCTGCTGTCCTGCATCGAGGATAAGAACCCCTGTATCTTCTTT GAGCCTAAGATCCTGTACAGAGCAGCAGCAGAGGAGGTGCCTATCGAGCCA TATAATATCCCTCTGTCTCAGGCCGAAGTGATCCAGGAGGGAAGCGACGTG ACCCTGGTGGCATGGGGAACACAGGTGCACGTGATCAGGGAGGTGGCCTCC ATGGCCAAGGAGAAGCTGGGCGTGTCTTGCGAAGTGATCGATCTGGAGGAC ATCATCCCTTGGGACGTGGATACAATCTGTAAGTCTGTGATCAAGACCGGC CGCCTGCTGATCAGCCACGAGGCACCACTGACAGGAGGATTCGCATCCGAG ATCAGCTCCACCGTGCAGGAGGAGTGCTTTCTGAATCTGGAGGCCCCAATC TCTCGGGTGTGCGGCTACGATACCCCCTTCCCTCACATCTTTGAGCCTTTC TACATCCCTGACAAGTGGAAGTGCTACGACGCTCTGCGGAAGATGATTAAC TATtga | opti-BCKDHB |
| 5 | CGCGTGGTACCTCTAGAGTCGACCCGGGCGGCCTCGAGGACGGGGTGAACT ACGCCTGAGGATCCGATCTTTTTCCCTCTGCCAAAAATTATGGGGACATCA TGAAGCCCCTTGAGCATCTGACTTCTGGCTAATAAAGGAAATTTATTTTCA TTGCAATAGTGTGTTGGAATTTTTTGTGTCTCTCACTCGGAAGCAATTCGT TGATCTGAATTTCGACCACCCATAATACCCATTACCCTGGTAGATAAGTAG CATGGCGGGTTAATCATTAACTACAAGGAACCCCTAGTGATGGAGTTGGCC ACTCCCTCTCTGCGCGCTCGCTCGCTCACTGAGGCCGGGCGACCAAAGGTC GCCCGACGCCCGGGCTTTGCCCGGGCGGCCTCAGTGAGCGAGCGAGCGCGC AGCCTTAATTAACCTAATTCACTGGCCGTCGTTTTACAACGTCGTGACTGG GAAAACCCTGGCGTTACCCAACTTAATCGCCTTGCAGCACATCCCCCTTTC GCCAGCTGGCGTAATAGCGAAGAGGCCCGCACCGATCGCCCTTCCCAACAG TTGCGCAGCCTGAATGGCGAATGGGACGCGCCCTGTAGCGGCGCATTAAGC GCGGCGGGTGTGGTGGTTACGCGCAGCGTGACCGCTACACTTGCCAGCGCC CTAGCGCCCGCTCCTTTCGCTTTCTTCCCTTCCTTTCTCGCCACGTTCGCC GGCTTTCCCCGTCAAGCTCTAAATCGGGGGCTCCCTTTAGGGTTCCGATTT AGTGCTTTACGGCACCTCGACCCCAAAAAACTTGATTAGGGTGATGGTTCA CGTAGTGGGCCATCGCCCTGATAGACGGTTTTTCGCCCTTTGACGTTGGAG TCCACGTTCTTTAATAGTGGACTCTTGTTCCAAACTGGAACAACACTCAAC CCTATCTCGGTCTATTCTTTTGATTTATAAGGGATTTTGCCGATTTCGGCC TATTGGTTAAAAAATGAGCTGATTTAACAAAAATTTAACGCGAATTTTAAC AAAATATTAACGCTTACAATTTAGGTGGCACTTTTCGGGGAAATGTGCGCG GAACCCCTATTTGTTTATTTTTCTAAATACATTCAAATATGTATCCGCTCA TGAGACAATAACCCTGATAAATGCTTCAATAATATTGAAAAAGGAAGAGTA TGAGTATTCAACATTTCCGTGTCGCCCTTATTCCCTTTTTTGCGGCATTTT GCCTTCCTGTTTTTGCTCACCCAGAAACGCTGGTGAAAGTAAAAGATGCTG AAGATCAGTTGGGTGCACGAGTGGGTTACATCGAACTGGATCTCAACAGCG GTAAGATCCTTGAGAGTTTTCGCCCCGAAGAACGTTTTCCAATGATGAGCA CTTTTAAAGTTCTGCTATGTGGCGCGGTATTATCCCGTATTGACGCCGGGC AAGAGCAACTCGGTCGCCGCATACACTATTCTCAGAATGACTTGGTTGAGT ACTCACCAGTCACAGAAAAGCATCTTACGGATGGCATGACAGTAAGAGAAT TATGCAGTGCTGCCATAACCATGAGTGATAACACTGCGGCCAACTTACTTC TGACAACGATCGGAGGACCGAAGGAGCTAACCGCTTTTTTGCACAACATGG GGGATCATGTAACTCGCCTTGATCGTTGGGAACCGGAGCTGAATGAAGCCA TACCAAACGACGAGCGTGACACCACGATGCCTGTAGCAATGGCAACAACGT TGCGCAAACTATTAACTGGCGAACTACTTACTCTAGCTTCCCGGCAACAAT TAATAGACTGGATGGAGGCGGATAAAGTTGCAGGACCACTTCTGCGCTCGG | rAAV vector: pJW152-pAAV.pCB-CBA-opt-hBCKDHB |

TABLE 1 -continued

Exemplary Sequences

| SEQ ID NO. | Sequence* | Description |
|---|---|---|
| | CCCTTCCGGCTGGCTGGTTTATTGCTGATAAATCTGGAGCCGGTGAGCGTG GGTCTCGCGGTATCATTGCAGCACTGGGGCCAGATGGTAAGCCCTCCCGTA TCGTAGTTATCTACACGACGGGGAGTCAGGCAACTATGGATGAACGAAATA GACAGATCGCTGAGATAGGTGCCTCACTGATTAAGCATTGGTAACTGTCAG ACCAAGTTTACTCATATATACTTTAGATTGATTTAAAACTTCATTTTTAAT TTAAAAGGATCTAGGTGAAGATCCTTTTTGATAATCTCATGACCAAAATCC CTTAACGTGAGTTTTCGTTCCACTGAGCGTCAGACCCCGTAGAAAAGATCA AAGGATCTTCTTGAGATCCTTTTTTTCTGCGCGTAATCTGCTGCTTGCAAA CAAAAAAACCACCGCTACCAGCGGTGGTTTGTTTGCCGGATCAAGAGCTAC CAACTCTTTTTCCGAAGGTAACTGGCTTCAGCAGAGCGCAGATACCAAATA CTGTTCTTCTAGTGTAGCCGTAGTTAGGCCACCACTTCAAGAACTCTGTAG CACCGCCTACATACCTCGCTCTGCTAATCCTGTTACCAGTGGCTGCTGCCA GTGGCGATAAGTCGTGTCTTACCGGGTTGGACTCAAGACGATAGTTACCGG ATAAGGCGCAGCGGTCGGGCTGAACGGGGGGTTCGTGCACACAGCCCAGCT TGGAGCGAACGACCTACACCGAACTGAGATACCTACAGCGTGAGCTATGAG AAAGCGCCACGCTTCCCGAAGGGAGAAAGGCGGACAGGTATCCGGTAAGCG GCAGGGTCGGAACAGGAGAGCGCACGAGGGAGCTTCCAGGGGGAAACGCCT GGTATCTTTATAGTCCTGTCGGGTTTCGCCACCTCTGACTTGAGCGTCGAT TTTTGTGATGCTCGTCAGGGGGGCGGAGCCTATGGAAAAACGCCAGCAACG CGGCCTTTTTACGGTTCCTGGCCTTTTGCTGGCCTTTTGCTCACATGTTCT TTCCTGCGTTATCCCCTGATTCTGTGGATAACCGTATTACCGCCTTTGAGT GAGCTGATACCGCTCGCCGCAGCCGAACGACCGAGCGCAGCGAGTCAGTGA GCGAGGAAGCGGAAGAGCGCCCAATACGCAAACCGCCTCTCCCCGCGCGTT GGCCGATTCATTAATGCAGCTGGCACGACAGGTTTCCCGACTGGAAAGCGG GCAGTGAGCGCAACGCAATTAATGTGAGTTAGCTCACTCATTAGGCACCCC AGGCTTTACACTTTATGCTTCCGGCTCGTATGTTGTGTGGAATTGTGAGCG GATAACAATTTCACACAGGAAACAGCTATGACCATGATTACGCCAGATTTA ATTAAGGCCTTAATTAGGCTGCGCGCTCGCTCGCTCACTGAGGCCGCCCGG GCAAAGCCCGGGCGTCGGGCGACCTTTGGTCGCCCGGCCTCAGTGAGCGAG CGAGCGCGCAGAGAGGGAGTGGCCAACTCCATCACTAGGGGTTCCTTGTAG TTAATGATTAACCCGCCATGCTACTTATCTACCAGGGTAATGGGGATCCTC TAGAACTATAGCTAGTCGACATTGATTATTGACTAGTTATTAATAGTAATC AATTACGGGGTCATTAGTTCATAGCCCATATATGGAGTTCCGCGTTACATA ACTTACGGTAAATGGCCCGCCTGGCTGACCGCCCAACGACCCCCGCCCATT GACGTCAATAATGACGTATGTTCCCATAGTAACGCCAATAGGGACTTTCCA TTGACGTCAATGGGTGGAGTATTTACGGTAAACTGCCCACTTGGCAGTACA TCAAGTGTATCATATGCCAAGTACGCCCCCTATTGACGTCAATGACGGTAA ATGGCCCGCCTGGCATTATGCCCAGTACATGACCTTATGGGACTTTCCTAC TTGGCAGTACATCTACGTATTAGTCATCGCTATTACCATGGTCGAGGTGAG CCCCACGTTCTGCTTCACTCTCCCCATCTCCCCCCCCTCCCCACCCCCAAT TTTGTATTTATTTATTTTTTAATTATTTTGTGCAGCGATGGGGGCGGGGGG GGGGGGGGGCGCGCGCCAGGCGGGGCGGGGCGGGCGAGGGGCGGGGCGG GGCGAGGCGGAGAGGTGCGGCGGCAGCCAATCAGAGCGGCGCGCTCCGAAA GTTTCCTTTTATGGCGAGGCGGCGGCGGCGGCGGCCCTATAAAAAGCGAAG CGCGCGGCGGGCGGGGAGTCGCTGCGACGCTGCCTTCGCCCCGTGCCCCGC TCCGCCGCCGCCTCGCGCCGCCCGCCCCGGCTCTGACTGACCGCGTTACTC CCACAGGTGAGCGGGCGGGACGGCCCTTCTCCTCCGGGCTGTAATTAGCGC TTGGTTTAATGACGGCTTGTTTCTTTTCTGTGGCTGCGTGAAAGCCTTGAG GGGCTCCGGGAGGGCCCTTTGTGCGGGGGGAGCGGCTCGGGGGTGCGTGC GTGTGTGTGTGCGTGGGGAGCGCCGCGTGCGGCTCCGCGCTGCCCGGCGGC TGTGAGCGCTGCGGGCGCGGCGCGGGGCTTTGTGCGCTCCGCAGTGTGCGC GAGGGGAGCGCGGCCGGGGGCGGTGCCCCGCGGTGCGGGGGGGCTGCGAG GGGAACAAAGGCTGCGTGCGGGGTGTGTGCGTGGGGGGGTGAGCAGGGGGT GTGGGCGCGTCGGTCGGGCTGCAACCCCCCCTGCACCCCCCTCCCCGAGTT GCTGAGCACGCCCGGCTTCGGGTGCGGGCTCCGTACGGGGCGTGGCGCG GGGCTCGCCGTGCCGGCGGGGGGTGGCGGCAGGTGGGGGTGCCGGGCGGG GCGGGGCCGCCTCGGGCCGGGAGGGCTCGGGGAGGGGCGCGGCGGCCCC CGGAGCGCCGGCGGCTGTCGAGGCGCGGCGAGCCGCAGCCATTGCCTTTTA TGGTAATCGTGCGAGAGGGCCAGGGACTTCCTTTGTCCCAAATCTGTGCG GAGCCGAAATCTGGGAGGCGCCGCCGCACCCCCTCTAGCGGGCGCGGGGCG AAGCGGTGCGGCGCCGGCAGGAAGGAAATGGGCGGGAGGGCCTTCGTGCG TCGCCGCGCCGCCGTCCCCTTCTCCCTCTCCAGCCTCGGGGCTGTCCGCGG GGGGACGGCTGCCTTCGGGGGGACGGGCAGGGCGGGGTTCGGCTTCTGG CGTGTGACCGGCGGCTCTAGAGCCTCTGCTAACCATGTTCATGCCTTCTTC TTTTTCCTACAGCTCCTGGGCAACGTGCTGGTTATTGTGCTGTCTCATCAT TTTGGCAAAGAATTCGCCACCATGGCCGTGGTCGCTGCTGCTGCCGGATGG CTGCTGAGACTGCGGGCCGCTGGGCTGAGGGACATTGGAGGAGACTGCCT GGGGCTGGGCTGGCAAGGGGCTTCCTGCACCCTGCAGCAACAGTGGAGGAC GCAGCACAGCGGAGACAGGTGGCCCACTTCACCTTTCAGCCCGATCCTGAG CCACGCGAGTACGGCCAGACACAGAAGATGAACCTGTTCCAGTCCGTGACC TCTGCCCTGGACAATAGCCTGGCCAAGGATCAACAGCCGTGATCTTTGGC GAGGACGTGGCCTTCGGCGGCGTGTTTCGGTGCACAGTGGGCCTGAGAGAC AAGTACGGCAAGGATCGGGTGTTCAACACCCCACTGTGCGAGCAGGGAATC GTGGGCTTTGGCATCGGCATCGCAGTGACCGGAGCAACAGCAATCGCAGAG | |

TABLE 1 -continued

Exemplary Sequences

| SEQ ID NO. | Sequence* | Description |
|---|---|---|
|  | ATCCAGTTCGCCGACTATATCTTCCCCGCCTTTGATCAGATCGTGAACGAG GCCGCCAAGTACAGGTATCGCTCCGGCGACCTGTTTAATTGCGGCAGCCTG ACCATCAGATCCCCTTGGGGATGCGTGGGACACGGCGCCCTGTATCACTCT CAGAGCCCAGAGGCCTTCTTTGCCCACTGCCCCGGCATCAAGGTGGTCATC CCACGGAGCCCCTTCCAGGCAAAGGGCCTGCTGCTGTCCTGCATCGAGGAT AAGAACCCCTGTATCTTCTTTGAGCCTAAGATCCTGTACAGAGCAGCAGCA GAGGAGGTGCCTATCGAGCCATATAATATCCCTCTGTCTCAGGCCGAAGTG ATCCAGGAGGGAAGCGACGTGACCCTGGTGGCATGGGGAACACAGGTGCAC GTGATCAGGGAGGTGGCCTCCATGGCCAAGGAGAAGCTGGGCGTGTCTTGC GAAGTGATCGATCTGAGGACCATCATCCCTTGGGACGTGGATACAATCTGT AAGTCTGTGATCAAGACCGGCCGCCTGCTGATCAGCCACGAGGCACCACTG ACAGGAGGATTCGCATCCGAGATCAGCTCCACCGTGCAGGAGGAGTGCTTT CTGAATCTGGAGGCCCCAATCTCTCGGGTGTGCGGCTACGATACCCCCTTC CCTCACATCTTTGAGCCTTTCTACATCCCTGACAAGTGGAAGTGCTACGAC GCTCTGCGGAAGATGATTAACTATTGAA |  |
| 6 | CTGCGCGCTCGCTCGCTCACTGAGGCCGCCCGGGCAAAGCCCGGGCGTCGG GCGACCTTTGGTCGCCCGGCCTCAGTGAGCGAGCGAGCGCGCAGAGAGGGA GTGTAGCCATGCTCTAGGAAGATCAATTCAATTCACGCGTCGACATTGATT ATTGACTAGTTATTAATAGTAATCAATTACGGGTCATTAGTTCATAGCCC ATATATGGAGTTCCGCGTTACATAACTTACGGTAAATGGCCCGCCTGGCTG ACCGCCCAACGACCCCCGCCCATTGACGTCAATAATGACGTATGTTCCCAT AGTAACGCCAATAGGGACTTTCCATTGACGTCAATGGGTGGATATTTACGG TAAACTGCCCACTTGGCAGTACATCAAGTGTATCATATGCCAAGTACGCCC CCTATTGACGTCAATGACGGTAAATGGCCCGCCTGGCATTATGCCCAGTAC ATGACCTTATGGGACTTTCCTACTTGGCAGTACATCTACGTATTAGTCATC GCTATTACCATGTCGAGGCCACGTTCTGCTTCACTCTCCCCATCTCCCCCC CCTCCCCACCCCCAATTTTGTATTTATTTATTTTTTAATTATTTTGTGCAG CGATGGGGGCGGGGGGGGGGGCGCGCGCCAGGCGGGGCGGGGCGGGGCGA GGGGCGGGGCGGGGCGAGGCGGAGAGGTGCGGCGGCAGCCAATCAGAGCGG CGCGCTCCGAAAGTTTCCTTTTATGGCGAGGCGGCGGCGGCGGCGGCCCTA TAAAAAGCGAAGCGCGCGGCGGGCGGGAGCAAGCTCTAGCCTCGAGGCCAC CATGGCCGTGGTCGCTGCTGCTGCCGGATGGCTGCTGAGACTGCGGGCCGC TGGGGCTGAGGGACATTGGAGGAGACTGCCTGGGGCTGGGCTGGCAAGGGG CTTCCTGCACCCTGCAGCAACAGTGGAGGACGCAGCACAGCGGAGACAGGT GGCCCACTTCACCTTTCAGCCCGATCCTGAGCCACGCGAGTACGGCCAGAC ACAGAAGATGAACCTGTTCCAGTCCGTGACCTCTGCCCTGGACAATAGCCT GGCCAAGGATCCAACAGCCGTGATCTTTGGCGAGGACGTGGCCTTCGGCGG CGTGTTTCGGTGCACAGTGGGCCTGAGAGACAAGTACGGCAAGGATCGGGT GTTCAACACCCCACTGTGCGAGCAGGGAATCGTGGGCTTTGGCATCGGCAT CGCAGTGACCGGAGCAACAGCAATCGCAGAGATCCAGTTCGCCGACTATAT CTTCCCCGCCTTTGATCAGATCGTGAACGAGGCCGCCAAGTACAGGTATCG CTCCGGCGACCTGTTTAATTGCGGCAGCCTGACCATCAGATCCCCTTGGGG ATGCGTGGGACACGGCGCCCTGTATCACTCTCAGAGCCCAGAGGCCTTCTT TGCCCACTGCCCCGGCATCAAGGTGGTCATCCCACGGAGCCCCTTCCAGGC AAAGGGCCTGCTGCTGTCCTGCATCGAGGATAAGAACCCCTGTATCTTCTT TGAGCCTAAGATCCTGTACAGAGCAGCAGCAGAGGAGGTGCCTATCGAGCC ATATAATATCCCTCTGTCTCAGGCCGAAGTGATCCAGGAGGGAAGCGACGT GACCCTGGTGGCATGGGAACACAGGTGCACGTGATCAGGGAGGTGGCCTC CATGGCCAAGGAGAAGCTGGGCGTGTCTTGCGAAGTGATCGATCTGAGGAC CATCATCCCTTGGGACGTGGATACAATCTGTAAGTCTGTGATCAAGACCGG CCGCCTGCTGATCAGCCACGAGGCACCACTGACAGGAGGATTCGCATCCGA GATCAGCTCCACCGTGCAGGAGGAGTGCTTTCTGAATCTGGAGGCCCCAAT CTCTCGGGTGTGCGGCTACGATACCCCCTTCCCTCACATCTTTGAGCCTTT CTACATCCCTGACAAGTGGAAGTGCTACGACGCTCTGCGGAAGATGATTAA CTATTGAGGATCCGATCTTTTTCCCTCTGCCAAAAATTATGGGGACATCAT GAAGCCCCTTGAGCATCTGACTTCTGGCTAATAAAGGAAATTTATTTTCAT TGCAATAGTGTGTTGGAATTTTTGTGTCTCTCACTCGGCCTAGGTAGATA AGTAGCATGGCGGGTTAATCATTAACTACAAGGAACCCCTAGTGATGGAGT TGGCCACTCCCTCTCTGCGCGCTCGCTCGCTCACTGAGGCCGGGCGACCAA AGGTCGCCCGACGCCCGGGCTTTGCCCGGGCGGCCTCAGTGAGCGAGCGAG CGCGCAGCCTTAATTAACCTAATTCACTGGCCGTCGTTTTACAACGTCGTG ACTGGGAAAACCCTGGCGTTACCCAACTTAATCGCCTTGCAGCACATCCCC CTTTCGCCAGCTGGCGTAATAGCGAAGAGGCCCGCACCGATCGCCCTTCCC AACAGTTGCGCAGCCTGAATGGCGAATGGGACGCGCCCTGTAGCGGCGCAT TAAGCGCGGCGGGTGTGGTGGTTACGCGCAGCGTGACCGCTACACTTGCCA GCGCCCTAGCGCCCGCTCCTTTCGCTTTCTTCCCTTCCTTTCTCGCCACGT TCGCCGGCTTTCCCCGTCAAGCTCTAAATCGGGGGCTCCCTTTAGGGTTCC GATTTAGTGCTTTACGGCACCTCGACCCCAAAAAACTTGATTAGGGTGATG GTTCACGTAGTGGGCCATCGCCCTGATAGACGGTTTTTCGCCCTTTGACGT TGGAGTCCACGTTCTTTAATAGTGGACTCTTGTTCCAAACTGGAACAACAC TCAACCCTATCTCGGTCTATTCTTTTGATTTATAAGGGATTTTGCCGATTT CGGCCTATTGGTTAAAAAATGAGCTGATTTAACAAAAATTTAACGCGAATT TTAACAAAATATTAACGCTTACAATTTAGGTGGCACTTTTCGGGGAAATGT | rAAV vector: pJW153- pAAVsc. CB6-opt- hBCKDHB |

TABLE 1 -continued

Exemplary Sequences

| SEQ ID NO. | Sequence* | Description |
|---|---|---|
| | GCGCGGAACCCCTATTTGTTTATTTTTCTAAATACATTCAAATATGTATCC GCTCATGAGACAATAACCCTGATAAATGCTTCAATAATATTGAAAAGGAA GAGTATGAGTATTCAACATTTCCGTGTCGCCCTTATTCCCTTTTTTGCGGC ATTTTGCCTTCCTGTTTTTGCTCACCCAGAAACGCTGGTGAAAGTAAAAGA TGCTGAAGATCAGTTGGGTGCACGAGTGGGTTACATCGAACTGGATCTCAA CAGCGGTAAGATCCTTGAGAGTTTTCGCCCCGAAGAACGTTTTCCAATGAT GAGCACTTTTAAAGTTCTGCTATGTGGCGCGGTATTATCCCGTATTGACGC CGGGCAAGAGCAACTCGGTCGCCGCATACACTATTCTCAGAATGACTTGGT TGAGTACTCACCAGTCACAGAAAAGCATCTTACGGATGGCATGACAGTAAG AGAATTATGCAGTGCTGCCATAACCATGAGTGATAACACTGCGGCCAACTT ACTTCTGACAACGATCGGAGGACCGAAGGAGCTAACCGCTTTTTTGCACAA CATGGGGGATCATGTAACTCGCCTTGATCGTTGGGAACCGGAGCTGAATGA AGCCATACCAAACGACGAGCGTGACACCACGATGCCTGTAGCAATGGCAAC AACGTTGCGCAAACTATTAACTGGCGAACTACTTACTCTAGCTTCCCGGCA ACAATTAATAGACTGGATGGAGGCGGATAAAGTTGCAGGACCACTTCTGCG CTCGGCCCTTCCGGCTGGCTGGTTTATTGCTGATAAATCTGGAGCCGGTGA GCGTGGGTCTCGCGGTATCATTGCAGCACTGGGGCCAGATGGTAAGCCCTC CCGTATCGTAGTTATCTACACGACGGGGAGTCAGGCAACTATGGATGAACG AAATAGACAGATCGCTGAGATAGGTGCCTCACTGATTAAGCATTGGTAACT GTCAGACCAAGTTTACTCATATATACTTTAGATTGATTTAAAACTTCATTT TTAATTTAAAAGGATCTAGGTGAAGATCCTTTTTGATAATCTCATGACCAA AATCCCTTAACGTGAGTTTTCGTTCCACTGAGCGTCAGACCCCGTAGAAAA GATCAAAGGATCTTCTTGAGATCCTTTTTTTCTGCGCGTAATCTGCTGCTT GCAAACAAAAAAACCACCGCTACCAGCGGTGGTTTGTTTGCCGGATCAAGA GCTACCAACTCTTTTTCCGAAGGTAACTGGCTTCAGCAGAGCGCAGATACC AAATACTGTTCTTCTAGTGTAGCCGTAGTTAGGCCACCACTTCAAGAACTC TGTAGCACCGCCTACATACCTCGCTCTGCTAATCCTGTTACCAGTGGCTGC TGCCAGTGGCGATAAGTCGTGTCTTACCGGGTTGGACTCAAGACGATAGTT ACCGGATAAGGCGCAGCGGTCGGGCTGAACGGGGGGTTCGTGCACACAGCC CAGCTTGGAGCGAACGACCTACACCGAACTGAGATACCTACAGCGTGAGCT ATGAGAAAGCGCCACGCTTCCCGAAGGGAGAAAGGCGGACAGGTATCCGGT AAGCGGCAGGGTCGGAACAGGAGAGCGCACGAGGGAGCTTCCAGGGGGAAA CGCCTGGTATCTTTATAGTCCTGTCGGGTTTCGCCACCTCTGACTTGAGCG TCGATTTTTGTGATGCTCGTCAGGGGGGCGGAGCCTATGGAAAAACGCCAG CAACGCGGCCTTTTTACGGTTCCTGGCCTTTTGCTGGCCTTTTGCTCACAT GTTCTTTCCTGCGTTATCCCCTGATTCTGTGGATAACCGTATTACCGCCTT TGAGTGAGCTGATACCGCTCGCCGCAGCCGAACGACCGAGCGCAGCGAGTC AGTGAGCGAGGAAGCGGAAGAGCGCCCAATACGCAAACCGCCTCTCCCCGC GCGTTGGCCGATTCATTAATGCAGCTGGCACGACAGGTTTCCCGACTGGAA AGCGGGCAGTGAGCGCAACGCAATTAATGTGAGTTAGCTCACTCATTAGGC ACCCCAGGCTTTACACTTTATGCTTCCGGCTCGTATGTTGTGTGGAATTGT GAGCGGATAACAATTTCACACAGGAAACAGCTATGACCATGATTACGCCAG ATTTAATTAAGGCCTTAATTAGG | |
| 7 | CGCGTGGTACCTCTAGAGTCGACCCGGGCGGCCTCGAGGACGGGGTGAACT ACGCCTGAGGATCCGATCTTTTTCCCTCTGCCAAAAATTATGGGGACATCA TGAAGCCCCTTGAGCATCTGACTTCTGGCTAATAAAGGAAATTTATTTTCA TTGCAATAGTGTGTTGGAATTTTTTGTGTCTCTCACTCGGAAGCAATTCGT TGATCTGAATTTCGACCACCCATAATACCCATTACCCTGGTAGATAAGTAG CATGGCGGGTTAATCATTAACTACAAGGAACCCCTAGTGATGGAGTTGGCC ACTCCCTCTCTGCGCGCTCGCTCGCTCACTGAGGCCGGGCGACCAAAGGTC GCCCGACGCCCGGGCTTTGCCGGGCGGCCTCAGTGAGCGAGCGAGCGCGC AGCCTTAATTAACCTAATTCACTGGCCGTCGTTTTACAACGTCGTGACTGG GAAAACCCTGGCGTTACCCAACTTAATCGCCTTGCAGCACATCCCCCTTTC GCCAGCTGGCGTAATAGCGAAGAGGCCCGCACCGATCGCCCTTCCCAACAG TTGCGCAGCCTGAATGGCGAATGGGACGCGCCCTGTAGCGGCGCATTAAGC GCGGCGGGTGTGGTGGTTACGCGCAGCGTGACCGCTACACTTGCCAGCGCC CTAGCGCCCGCTCCTTTCGCTTTCTTCCCTTCCTTTCTCGCCACGTTCGCC GGCTTTCCCCGTCAAGCTCTAAATCGGGGGCTCCCTTTAGGGTTCCGATTT AGTGCTTTACGGCACCTCGACCCCAAAAAACTTGATTAGGGTGATGGTTCA CGTAGTGGGCCATCGCCCTGATAGACGGTTTTTCGCCCTTTGACGTTGGAG TCCACGTTCTTTAATAGTGGACTCTTGTTCCAAACTGGAACAACACTCAAC CCTATCTCGGTCTATTCTTTTGATTTATAAGGGATTTTGCCGATTTCGGCC TATTGGTTAAAAAATGAGCTGATTTAACAAAAATTTAACGCGAATTTTAAC AAAATATTAACGCTTACAATTTAGGTGGCACTTTTCGGGGAAATGTGCGCG GAACCCCTATTTGTTTATTTTTCTAAATACATTCAAATATGTATCCGCTCA TGAGACAATAACCCTGATAAATGCTTCAATAATATTGAAAAGGAAGAGTA TGAGTATTCAACATTTCCGTGTCGCCCTTATTCCCTTTTTTGCGGCATTTT GCCTTCCTGTTTTTGCTCACCCAGAAACGCTGGTGAAAGTAAAAGATGCTG AAGATCAGTTGGGTGCACGAGTGGGTTACATCGAACTGGATCTCAACAGCG GTAAGATCCTTGAGAGTTTTCGCCCCGAAGAACGTTTTCCAATGATGAGCA CTTTTAAAGTTCTGCTATGTGGCGCGGTATTATCCCGTATTGACGCCGGGC AAGAGCAACTCGGTCGCCGCATACACTATTCTCAGAATGACTTGGTTGAGT ACTCACCAGTCACAGAAAAGCATCTTACGGATGGCATGACAGTAAGAGAAT | rAAV vector: pJW154-pAAV-pCB-opt-BCKDHB-T2A-opt-BCKDHA-1 |

TABLE 1-continued

Exemplary Sequences

| SEQ ID NO. | Sequence* | Description |
|---|---|---|
| | TATGCAGTGCTGCCATAACCATGAGTGATAACACTGCGGCCAACTTACTTC | |
| | TGACAACGATCGGAGGACCGAAGGAGCTAACCGCTTTTTTGCACAACATGG | |
| | GGGATCATGTAACTCGCCTTGATCGTTGGGAACCGGAGCTGAATGAAGCCA | |
| | TACCAAACGACGAGCGTGACACCACGATGCCTGTAGCAATGGCAACAACGT | |
| | TGCGCAAACTATTAACTGGCGAACTACTTACTCTAGCTTCCCGGCAACAAT | |
| | TAATAGACTGGATGGAGGCGGATAAAGTTGCAGGACCACTTCTGCGCTCGG | |
| | CCCTTCCGGCTGGCTGGTTTATTGCTGATAAATCTGGAGCCGGTGAGCGTG | |
| | GGTCTCGCGGTATCATTGCAGCACTGGGGCCAGATGGTAAGCCCTCCCGTA | |
| | TCGTAGTTATCTACACGACGGGGAGTCAGGCAACTATGGATGAACGAAATA | |
| | GACAGATCGCTGAGATAGGTGCCTCACTGATTAAGCATTGGTAACTGTCAG | |
| | ACCAAGTTTACTCATATATACTTTAGATTGATTTAAAACTTCATTTTTAAT | |
| | TTAAAAGGATCTAGGTGAAGATCCTTTTTGATAATCTCATGACCAAAATCC | |
| | CTTAACGTGAGTTTTCGTTCCACTGAGCGTCAGACCCCGTAGAAAAGATCA | |
| | AAGGATCTTCTTGAGATCCTTTTTTTCTGCGCGTAATCTGCTGCTTGCAAA | |
| | CAAAAAAACCACCGCTACCAGCGGTGGTTTGTTTGCCGGATCAAGAGCTAC | |
| | CAACTCTTTTTCCGAAGGTAACTGGCTTCAGCAGAGCGCAGATACCAAATA | |
| | CTGTTCTTCTAGTGTAGCCGTAGTTAGGCCACCACTTCAAGAACTCTGTAG | |
| | CACCGCCTACATACCTCGCTCTGCTAATCCTGTTACCAGTGGCTGCTGCCA | |
| | GTGGCGATAAGTCGTGTCTTACCGGGTTGGACTCAAGACGATAGTTACCGG | |
| | ATAAGGCGCAGCGGTCGGGCTGAACGGGGGGTTCGTGCACACAGCCCAGCT | |
| | TGGAGCGAACGACCTACACCGAACTGAGATACCTACAGCGTGAGCTATGAG | |
| | AAAGCGCCACGCTTCCCGAAGGGAGAAAGGCGGACAGGTATCCGGTAAGCG | |
| | GCAGGGTCGGAACAGGAGAGCGCACGAGGGAGCTTCCAGGGGGAAACGCCT | |
| | GGTATCTTTATAGTCCTGTCGGGTTTCGCCACCTCTGACTTGAGCGTCGAT | |
| | TTTTGTGATGCTCGTCAGGGGGGCGGAGCCTATGGAAAAACGCCAGCAACG | |
| | CGGCCTTTTTACGGTTCCTGGCCTTTTGCTGGCCTTTTGCTCACATGTTCT | |
| | TTCCTGCGTTATCCCCTGATTCTGTGGATAACCGTATTACCGCCTTTGAGT | |
| | GAGCTGATACCGCTCGCCGCAGCCGAACGACCGAGCGCAGCGAGTCAGTGA | |
| | GCGAGGAAGCGGAAGAGCGCCCAATACGCAAACCGCCTCTCCCCGCGCGTT | |
| | GGCCGATTCATTAATGCAGCTGGCACGACAGGTTTCCCGACTGGAAAGCGG | |
| | GCAGTGAGCGCAACGCAATTAATGTGAGTTAGCTCACTCATTAGGCACCCC | |
| | AGGCTTTACACTTTATGCTTCCGGCTCGTATGTTGTGTGGAATTGTGAGCG | |
| | GATAACAATTTCACACAGGAAACAGCTATGACCATGATTACGCCAGATTTA | |
| | ATTAAGGCCTTAATTAGGCTGCGCGCTCGCTCGCTCACTGAGGCCGCCCGG | |
| | GCAAAGCCCGGGCGTCGGGCGACCTTTGGTCGCCCGGCCTCAGTGAGCGAG | |
| | CGAGCGCGCAGAGAGGGAGTGGCCAACTCCATCACTAGGGGTTCCTTGTAG | |
| | TTAATGATTAACCCGCCATGCTACTTATCTACCAGGGTAATGGGGATCCTC | |
| | TAGAACTATAGCTAGTCGACATTGATTATTGACTAGTTATTAATAGTAATC | |
| | AATTACGGGGTCATTAGTTCATAGCCCATATATGGAGTTCCGCGTTACATA | |
| | ACTTACGGTAAATGGCCCGCCTGGCTGACCGCCCAACGACCCCCGCCCATT | |
| | GACGTCAATAATGACGTATGTTCCCATAGTAACGCCAATAGGGACTTTCCA | |
| | TTGACGTCAATGGGTGGAGTATTTACGGTAAACTGCCCACTTGGCAGTACA | |
| | TCAAGTGTATCATATGCCAAGTACGCCCCCTATTGACGTCAATGACGGTAA | |
| | ATGGCCCGCCTGGCATTATGCCCAGTACATGACCTTATGGGACTTTCCTAC | |
| | TTGGCAGTACATCTACGTATTAGTCATCGCTATTACCATGGTCGAGGTGAG | |
| | CCCCACGTTCTGCTTCACTCTCCCCATCTCCCCCCCCTCCCCACCCCCAAT | |
| | TTTGTATTTATTTATTTTTAATTATTTTGTGCAGCGATGGGGGCGGGGG | |
| | GGGGGGGGGCGCGCGCCAGGCGGGGCGGGCGGGCGAGGGGCGGGCG | |
| | GGCGAGGCGGAGAGGTGCGGCGGCAGCCAATCAGAGCGGCGCGCTCCGAAA | |
| | GTTTCCTTTTATGGCGAGGCGGCGGCGGCGGCGGCCCTATAAAAAGCGAAG | |
| | CGCGCGGCGGGCGGGAGTCGCTGCGACGCTGCCTTCGCCCCGTGCCCCGC | |
| | TCCGCCGCCGCCTCGCGCCGCCCGCCCCGGCTCTGACTGACCGCGTTACTC | |
| | CCACGCCACCATGGCCGTGGTCGCTGCTGCTGCCGGATGGCTGCTGAGACT | |
| | GCGGGCCGCTGGGGCTGAGGGACATTGGAGGAGACTGCCTGGGGCTGGGCT | |
| | GGCAAGGGCTTCCTGCACCCTGCAGCAACAGTGGAGGACGCAGCACAGCG | |
| | GAGACAGGTGGCCCACTTCACCTTTCAGCCCGATCCTGAGCCACGCGAGTA | |
| | CGGCCAGACACAGAAGATGAACCTGTTCCAGTCCGTGACCTCTGCCCTGGA | |
| | CAATAGCCTGGCCAAGGATCCAACAGCCGTGATCTTTGCGGAGGACGTGGC | |
| | CTTCGGCGGCGTGTTTCGGTGCACAGTGGGCCTGAGAGACAAGTACGGCAA | |
| | GGATCGGGTGTTCAACACCCCACTGTGCGAGCAGGGAATCGTGGGCTTTGG | |
| | CATCGGCATCGCAGTGACCGGAGCAACAGCAATCGCAGAGATCCAGTTCGC | |
| | CGACTATATCTTCCCCGCCTTTGATCAGATCGTGAACGAGGCCGCCAAGTA | |
| | CAGGTATCGCTCCGGCGACCTGTTTAATTGCGGCAGCCTGACCATCAGATC | |
| | CCCTTGGGGATGCGTGGGACACGGCGCCCTGTATCACTCTCAGAGCCCAGA | |
| | GGCCTTCTTTGCCCACTGCCCCGGCATCAAGGTGGTCATCCCACGGAGCCC | |
| | CTTCCAGGCAAAGGGCCTGCTGCTGTCCTGCATCGAGGATAAGAACCCCTG | |
| | TATCTTCTTTGAGCCTAAGATCCTGTACAGAGCAGCAGCAGAGGAGGTGCC | |
| | TATCGAGCCATATAATATCCCTCTGTCTCAGGCCGAAGTGATCCAGGAGGG | |
| | AAGCGACGTGACCCTGGTGGCATGGGGAACACAGGTGCACGTGATCAGGGA | |
| | GGTGGCCTCCATGGCCAAGGAGAAGCTGGGCGTGTCTTGCGAAGTGATCGA | |
| | TCTGAGGACCATCATCCCTTGGGACGTGGATACAATCTGTAAGTCTGTGAT | |
| | CAAGACCGGCGCCTGCTGATCAGCCACGAGGCACCACTGACAGGAGGATT | |
| | CGCATCCGAGATCAGCTCCACCGTGCAGGAGGAGTGCTTTCTGAATCTGGA | |
| | GGCCCCAATCTCTCGGGTGTGCGGCTACGATACCCCCTTCCCTCACATCTT | |

TABLE 1 -continued

Exemplary Sequences

| SEQ ID NO. | Sequence* | Description |
|---|---|---|
| | TGAGCCTTTCTACATCCCTGACAAGTGGAAGTGCTACGACGCTCTGCGGAA GATGATTAACTATGGATCCGGTGAGGGCAGAGGAAGTCTTCTAACATGCGG TGACGTGGAGGAGAATCCGGGCCCTGAATTCGCCACCATGGCCGTCGCAAT CGCCGCCGCAAGAGTGTGGAGACTGAATCGGGGACTGAGCCAGGCCGCACT GCTGCTGCTGAGACAGCCAGGAGCCAGAGGCCTGGCCAGGAGCCACCCACC TAGGCAGCAGCAGCAGTTCAGCTCCCTGGACGATAAGCCACAGTTTCCCGG CGCCTCTGCCGAGTTCATCGACAAGCTGGAGTTTATCCAGCCAAACGTGAT CAGCGGCATCCCCATCTACCGCGTGATGGACCGGCAGGGCCAGATCATCAA TCCATCCGAGGACCCCACCTGCCAAAGGAGAAGGTGCTGAAGCTGTACAA GTCTATGACCCTGCTGAACACAATGGATAGAATCCTGTATGAGTCCCAGCG CCAGGGCCGGATCTCTTTCTACATGACCAACTATGGCGAGGAGGGCACACA CGTGGGCAGCGCCGCCGCCCTGGACAATACCGATCTGGTGTTCGGCCAGTA TAGAGAGGCCGGCGTGCTGATGTACAGGGACTATCCTCTGGAGCTGTTTAT GGCCCAGTGCTACGGCAATATCAGCGATCTGGGCAAGGGCCGCCAGATGCC AGTGCACTATGGCTGTAAGGAGCGGCACTTCGTGACCATCTCTAGCCCCCT GGCCACACAGATCCCTCAGGCAGTGGGAGCAGCCTACGCCGCCAAGAGAGC CAACGCCAATAGGGTGGTCATCTGCTATTTTGGAGAGGGAGCAGCCTCCGA GGGCGACGCACACGCCGGCTTCAACTTTGCCGCCACCCTGGAGTGCCCTAT CATCTTCTTTTGTAGAAACAATGGCTACGCCATCTCTACCCCAACAAGCGA GCAGTATAGGGGCGATGGAATCGCAGCCAGAGGCCCAGGCTACGGCATCAT GTCCATCAGGGTGGACGGCAACGACGTGTTCGCCGTGTATAATGCCACAAA GGAGGCACGGAGAAGGGCAGTGGCAGAGAACCAGCCCTTTCTGATCGAGGC CATGACCTACAGAATCGGCCACCACAGCACATCCGACGATTCCTCTGCCTA CAGGTCTGTGGACGAAGTGAATTATTGGGACAAGCAGGATCACCCTATCAG CAGACTGAGGCACTATCTGCTGTCCCAGGGCTGGTGGGATGAGGAGCAGGA GAAGGCCTGGAGGAAGCAGAGCCGCCGGAAAGTGATGGAGGCCTTCGAGCA GGCAGAGAGGAAGCCAAAGCCCAACCCTAATCTGCTGTTTTCCGACGTGTA CCAGGAGATGCCTGCCCAGCTGAGGAAGCAGCAGGAGAGCCTGGCAAGACA CCTGCAGACATACGGCGAGCATTACCCCCTGGACCATTTTGATAAGTGAA | |
| 8 | TTGGCCACTCCCTCTCTGCGCGCTCGCTCGCTCACTGAGGCCGGGCGACCA AAGGTCGCCCGACGCCCGGGCTTTGCCCGGGCGGCCTCAGTGAGCGAGCGA GCGCGCAGAGAGGGAGTGGCCAACTCCATCACTAGGGGTTCCTAGATCGA ATTCTACCACATTTGTAGAGGTTTTACTTGCTTTAAAAAACCTCCCACATC TCCCCCTGAACCTGAAACATAAAATGAATGCAATTGTTGTTGTTAACTTGT TTATTGCAGCTTATAATGGTTACAAATAAAGCAATAGCATCACAAATTTCA CAAATAAAGCATTTTTTTCACTGCATTCTAGTTGTGGTTTGTCCAAACTCA TCAATGTATCTTATCATGTCTGTCGATCACTTATCAAAATGGTCCAGGGGG TAATGCTCGCCGTATGTCTGCAGGTGTCTTGCCAGGCTCTCCTGCTGCTTC CTCAGCTGGGCAGGCATCTCCTGGTACACGTCGGAAAACAGCAGATTAGGG TTGGGCTTTGGCTTCCTCTCTGCCTGCTCGAAGGCCTCCATCACTTTCCGG CGGCTCTGCTTCCTCCAGGCCTTCTCCTGCTCCTCATCCCACCAGCCCTGG GACAGCAGATAGTGCCTCAGTCTGCTGATAGGGTGATCCTGCTTGTCCCAA TAATTCACTTCGTCCACAGACCTGTAGGCAGAGGAATCGTCGGATGTGCTG TGGTGGCCGATTCTGTAGGTCATGGCCTCGATCAGAAAGGGCTGGTTCTCT GCCACTGCCCTTCTCCGTGCCTCCTTTGTGGCATTATACACGGCGAACACG TCGTTGCCGTCCACCCTGATGGACATGATGCCGTAGCCTGGGCCTCTGGCT GCGATTCCATCGCCCCTATACTGCTCGCTTGTTGGGGTAGAGATGGCGTAG CCATTGTTTCTACAAAAGAAGATGATAGGGCACTCCAGGGTGGCGGCAAAG TTGAAGCCGGCGTGTGCGTCGCCCTCGGAGGCTGCTCCCTCTCCAAAATAG CAGATGACCACCCTATTGGCGTTGGCTCTCTTGGCGGCGTAGGCTGCTCCC ACTGCCTGAGGGATCTGTGTGGCCAGGGGGCTAGAGATGGTCACGAAGTGC CGCTCCTTACAGCCATAGTGCACTGGCATCTGGCGGCCCTTGCCCAGATCG CTGATATTGCCGTAGCACTGGGCCATAAACAGCTCCAGAGGATAGTCCCTG TACATCAGCACGCCGGCCTCTCTATACTGGCCGAACACCAGATCGGTATTG TCCAGGGCGGCGGCGCTGCCCACGTGTGTGCCCTCCTCGCCATAGTTGGTC ATGTAGAAAGAGATCCGGCCCTGGCGCTGGGACTCATACAGGATTCTATCC ATTGTGTTCAGCAGGGTCATAGACTTGTACAGCTTCAGCACCTTCTCCTTT GGCAGGTGGGGTCCTCGGATGGATTGATGATCTGGCCCTGCCGGTCCATC ACGCGGTAGATGGGATGCCGCTGATCACGTTTGGCTGGATAAACTCCAGC TTGTCGATGAACTCGGCAGAGGCGCCGGGAAACTGTGGCTTATCGTCCAGG GAGCTGAACTGCTGCTGCTGCCTAGGTGGGTGGCTCCTGGCCAGGCCTCTG GCTCCTGGCTGTCTCAGCAGCAGCAGTGCGGCCTGGCTCAGTCCCCGATTC AGTCTCCACACTCTTGCGGCGGCGATTGCGACGGCCATGGTGGCCTAGCGC TAGAGCTTGCTCCCGCCCGCCGCGCGCTTCGCTTTTTATAGGGCGCCGCC GCCGCCGCCTCGCCATAAAAGGAAACTTTCGGAGCGCGCCGCTCTGATTGG CTGCCGCCGCACCTCTCCGCCTCGCCCCGCCCCGCCCCTCGCCCCCATCGC TGCACAAAATAATTAAAAAATAAATAAATACAAAATTGGGGGTGGGGAGGG GGGGGAGATGGGAGAGTGAAGCAGAACGTGGCCTCGGATCCCCGGGCTG CAGTATTAATAGTAATCAATTACGGGGTCATTAGTTCATAGCCCATATATG GAGTTCCGCGTTACATAACTTACGGTAAATGGCCCGCCTGGCTGACCGCCC AACGACCCCCGCCCATTGACGTCAATAATGACGTATGTTCCCATAGTAACG CCAATAGGGACTTTCCATTGACGTCAATGGGTGGAGTATTTACGGTAAACT GCCCACTTGGCAGTACATCAAGTGTATCATATGCCAAGTACGCCCCCTATT | rAAV vector: pJW162-SURE\Cell pAAV-SV40-opti-BCKDHA-BiCB6-opti-BCKDHB-RBG |

TABLE 1 -continued

Exemplary Sequences

| SEQ ID NO. | Sequence* | Description |
|---|---|---|
| | GACGTCAATGACGGTAAATGGCCCGCCTGGCATTATGCCCAGTACATGACC | |
| | TTATGGGACTTTCCTACTTGGCAGTACATCTACGTATTAGTCATCGCTATT | |
| | ACCATGTCGAGGCCACGTTCTGCTTCACTCTCCCCATCTCCCCCCCCTCCC | |
| | CACCCCCAATTTTGTATTTATTTATTTTTAATTATTTTGTGCAGCGATGG | |
| | GGGCGAGGGGCGGGGCGGGGCGAGGCGGAGAGGTGCGGCGGCAGCCAATCA | |
| | GAGCGGCGCGCTCCGAAAGTTTCCTTTTATGGCGAGGCGGCGGCGGCGGCG | |
| | GCCCTATAAAAAGCGAAGCGCGCGGCGGGCGGGAGCAAGCTCGCTAGCACT | |
| | AGTGCCACCATGGCCGTGGTCGCTGCTGCTGCCGGATGGCTGCTGAGACTG | |
| | CGGGCCGCTGGGGCTGAGGGACATTGGAGGAGACTGCCTGGGGCTGGGCTG | |
| | GCAAGGGGCTTCCTGCACCCTGCAGCAACAGTGGAGGACGCAGCACAGCGG | |
| | AGACAGGTGGCCCACTTCACCTTTCAGCCCGATCCTGAGCCACGCGAGTAC | |
| | GGCCAGACACAGAAGATGAACCTGTTCCAGTCCGTGACCTCTGCCCTGGAC | |
| | AATAGCCTGGCCAAGGATCCAACAGCCGTGATCTTTGGCGAGGACGTGGCC | |
| | TTCGGCGGCGTGTTTCGGTGCACAGTGGGCCTGAGAGACAAGTACGGCAAG | |
| | GATCGGGTGTTCAACACCCCACTGTGCGAGCAGGGAATCGTGGGCTTTGGC | |
| | ATCGGCATCGCAGTGACCGGAGCAACAGCAATCGCAGAGATCCAGTTCGCC | |
| | GACTATATCTTCCCCGCCTTTGATCAGATCGTGAACGAGGCCGCCAAGTAC | |
| | AGGTATCGCTCCGGCGACCTGTTTAATTGCGGCAGCCTGACCATCAGATCC | |
| | CCTTGGGGATGCGTGGGACACGGCGCCCTGTATCACTCTCAGAGCCCAGAG | |
| | GCCTTCTTTGCCCACTGCCCCGGCATCAAGGTGGTCATCCCACGGAGCCCC | |
| | TTCCAGGCAAAGGGCCTGCTGCTGTCCTGCATCGAGGATAAGAACCCCTGT | |
| | ATCTTCTTTGAGCCTAAGATCCTGTACAGAGCAGCAGCAGAGGAGGTGCCT | |
| | ATCGAGCCATATAATATCCCTCTGTCTCAGGCCGAAGTGATCCAGGAGGGA | |
| | AGCGACGTGACCCTGGTGGCATGGGGAACACAGGTGCACGTGATCAGGGAG | |
| | GTGGCCTCCATGGCCAAGGAGAAGCTGGGCGTGTCTTGCGAAGTGATCGAT | |
| | CTGAGGACCATCATCCCTTGGGACGTGGATACAATCTGTAAGTCTGTGATC | |
| | AAGACCGGCCGCCTGCTGATCAGCCACGAGGCACCACTGACAGGAGGATTC | |
| | GCATCCGAGATCAGCTCCACCGTGCAGGAGGAGTGCTTTCTGAATCTGGAG | |
| | GCCCCAATCTCTCGGGTGTGCGGCTACGATACCCCCTTCCCTCACATCTTT | |
| | GAGCCTTTCTACATCCCTGACAAGTGGAAGTGCTACGACGTCTGCGGAAG | |
| | ATGATTAACTATTGAGCGGCCGCTCTAGAGATCTTTTTCCCTCTGCCAAAA | |
| | ATTATGGGGACATCATGAAGCCCCTTGAGCATCTGACTTCTGGCTAATAAA | |
| | GGAAATTTATTTTCATTGCAATAGTGTGTTGGAATTTTTTGTGTCTCTCAC | |
| | TCGGCATGCTGGGGAGAGATCTAGGAACCCCTAGTGATGGAGTTGGCCACT | |
| | CCCTCTCTGCGCGCTCGCTCGCTCACTGAGGCCGCCCGGGCAAAGCCCGGG | |
| | CGTCGGGCGACCTTTGGTCGCCCGGCCTCAGTGAGCGAGCGAGCGCGCAGA | |
| | GAGGGAGTGGCCATGCAGCCAGCTGGCGTAATAGCGAAGAGGCCCGCACCG | |
| | ATCGCCCTTCCCAACAGTTGCGTAGCCTGAATGGCGAATGGCGCGACGCGC | |
| | CCTGTAGCGGCGCATTAAGCGCGGCGGGTGTGGTGGTTACGCGCAGCGTGA | |
| | CCGCTACACTTGCCAGCGCCCTAGCGCCCGCTCCTTTCGCTTTCTTCCCTT | |
| | CCTTTCTCGCCACGTTCGCCGGCTTTCCCCGTCAAGCTCTAAATCGGGGGC | |
| | TCCCTTTAGGGTTCCGATTTAGTGCTTTACGGCACCTCGACCCCAAAAAAC | |
| | TTGATTAGGGTGATGGTTCACGTAGTGGGCCATCGCCCTGATAGACGGTTT | |
| | TTCGCCCTTTGACGTTGGAGTCCACGTTCTTTAATAGTGGACTCTTGTTCC | |
| | AAACTGGAACAACACTCAACCCTATCTCGGTCTATTCTTTTGATTTATAAG | |
| | GGATTTTGCCGATTTCGGCCTATTGGTTAAAAAATGAGCTGATTTAACAAA | |
| | AATTTAACGCGAATTTTAACAAAATATTAACGTTTACAATTTCCTGATGCG | |
| | GTATTTTCTCCTTACGCATCTGTGCGGTATTTCACACCGCATATGGTGCAC | |
| | TCTCAGTACAATCTGCTCTGATGCCGCATAGTTAAGCCAGCCCCGACACCC | |
| | GCCAACACCCGCTGACGCGCCCTGACGGGCTTGTCTGCTCCCGGCATCCGC | |
| | TTACAGACAAGCTGTGACCGTCTCCGGGAGCTGCATGTGTCAGAGGTTTTC | |
| | ACCGTCATCACCGAAACGCGCGAGACGAAAGGGCCTCGTGATACGCCTATT | |
| | TTTATAGGTTAATGTCATGATAATAATGGTTTCTTAGACGTCAGGTGGCAC | |
| | TTTTCGGGGAAATGTGCGCGGAACCCCTATTTGTTTATTTTTCTAAATACA | |
| | TTCAAATATGTATCCGCTCATGAGACAATAACCCTGATAAATGCTTCAATA | |
| | ATATTGAAAAAGGAAGAGTATGAGTATTCAACATTTCCGTGTCGCCCTTAT | |
| | TCCCTTTTTTGCGGCATTTTGCCTTCCTGTTTTTGCTCACCCAGAAACGCT | |
| | GGTGAAAGTAAAAGATGCTGAAGATCAGTTGGGTGCACGAGTGGGTTACAT | |
| | CGAACTGGATCTCAACAGCGGTAAGATCCTTGAGAGTTTTCGCCCCGAAGA | |
| | ACGTTTTCCAATGATGAGCACTTTTAAAGTTCTGCTATGTGGCGCGGTATT | |
| | ATCCCGTATTGACGCCGGGCAAGAGCAACTCGGTCGCCGCATACACTATTC | |
| | TCAGAATGACTTGGTTGAGTACTCACCAGTCACAGAAAAGCATCTTACGGA | |
| | TGGCATGACAGTAAGAGAATTATGCAGTGCTGCCATAACCATGAGTGATAA | |
| | CACTGCGGCCAACTTACTTCTGACAACGATCGGAGGACCGAAGGAGCTAAC | |
| | CGCTTTTTTGCACAACATGGGGGATCATGTAACTCGCCTTGATCGTTGGGA | |
| | ACCGGAGCTGAATGAAGCCATACCAAACGACGAGCGTGACACCACGATGCC | |
| | TGTAGCAATGGCAACAACGTTGCGCAAACTATTAACTGGCGAACTACTTAC | |
| | TCTAGCTTCCCGGCAACAATTAATAGACTGGATGGAGGCGGATAAAGTTGC | |
| | AGGACCACTTCTGCGCTCGGCCCTTCCGGCTGGCTGGTTTATTGCTGATAA | |
| | ATCTGGAGCCGGTGAGCGTGGGTCTCGCGGTATCATTGCAGCACTGGGGCC | |
| | AGATGGTAAGCCCTCCCGTATCGTAGTTATCTACACGACGGGGAGTCAGGC | |
| | AACTATGGATGAACGAAATAGACAGATCGCTGAGATAGGTGCCTCACTGAT | |
| | TAAGCATTGGTAACTGTCAGACCAAGTTTACTCATATATACTTTAGATTGA | |
| | TTTAAAACTTCATTTTTAATTTAAAAGGATCTAGGTGAAGATCCTTTTTGA | |

TABLE 1 -continued

Exemplary Sequences

| SEQ ID NO. | Sequence* | Description |
|---|---|---|
| | TAATCTCATGACCAAAATCCCTTAACGTGAGTTTTCGTTCCACTGAGCGTC<br>AGACCCCGTAGAAAAGATCAAAGGATCTTCTTGAGATCCTTTTTTCTGCG<br>CGTAATCTGCTGCTTGCAAACAAAAAAACCACCGCTACCAGCGGTGGTTTG<br>TTTGCCGGATCAAGAGCTACCAACTCTTTTTCCGAAGGTAACTGGCTTCAG<br>CAGAGCGCAGATACCAAATACTGTCCTTCTAGTGTAGCCGTAGTTAGGCCA<br>CCACTTCAAGAACTCTGTAGCACCGCCTACATACCTCGCTCTGCTAATCCT<br>GTTACCAGTGGCTGCTGCCAGTGGCGATAAGTCGTGTCTTACCGGGTTGGA<br>CTCAAGACGATAGTTACCGGATAAGGCGCAGCGGTCGGGCTGAACGGGGGG<br>TTCGTGCACACAGCCCAGCTTGGAGCGAACGACCTACACCGAACTGAGATA<br>CCTACAGCGTGAGCATTGAGAAAGCGCCACGCTTCCCGAAGGGAGAAAGGC<br>GGACAGGTATCCGGTAAGCGGCAGGGTCGGAACAGGAGAGCGCACGAGGGA<br>GCTTCCAGGGGGAAACGCCTGGTATCTTTATAGTCCTGTCGGGTTTCGCCA<br>CCTCTGACTTGAGCGTCGATTTTTGTGATGCTCGTCAGGGGGCGGAGCCT<br>ATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAA<br>CCGTATTACCGCCTTTGAGTGAGCTGATACCGCTCGCCGCAGCCGAACGAC<br>CGAGCGCAGCGAGTCAGTGAGCGAGGAAGCGGAAGAGCGCCCAATACGCAA<br>ACCGCCTCTCCCCGCGCGTTGGCCGATTCATTAATGCAGCTGGGCTGCAGG<br>GGGGGGGGGGGGGGGTGGGGGGGGGGGGGGGGGG | |

*Unless otherwise specified, all sequences are described in direction of 5'-to-3'

EXAMPLES

Example 1: Analysis of BCKDHA Gene Therapy

MSUD is a rare genetic disorder affecting degradation of the branched-chain amino acids (BCAA; leucine, isoleucine, and valine) and their ketoacid derivatives. It is caused by biallelic mutations in one of three genes that encode subunits of the branched-chain ketoacid dehydrogenase complex (BCKDHA, BCKDHB, and DBT). Severe (classical) MSUD is fatal without treatment. Dietary BCAA restriction is the mainstay of treatment but is difficult to implement, has imperfect efficacy, and affords no protection against episodic and life-threatening encephalopathic crises. Liver transplantation is an effective alternative to dietary therapy, but entails risks of surgery and long-term immunosuppression.

MSUD affects approximately 1 per 185,000 births worldwide and is screened for in most U.S. states and developed countries. The birth incidence is much higher (~1 per 500) among Old Order Mennonites of North America due to a common BCKDHA founder variant (c.1312 T>A; p.Tyr438Asn) that segregates with a population-specific carrier frequency of 4.5%. BCKDHA and BCKDHB mutations (e.g., Patients homozygous for BCKDHA c.1312T>A) are the most common causes of MSUD and majority of these cases are severe classical type. These type of patients have extremely low (<2%) BCKDC enzyme activity and become biochemically unstable within days of life. A naturally occurring BCKDHA loss-of-function mutation (c.248C>T) was identified in Australian Shorthorn and Hereford cattle as early 1986 and rediscovered within Central Indiana herds in 2015. Newborn calves homozygous for BCKDHA c.248C>T have a phenotype similar to the human disease. An alignment of human and bovine sequences was performed and assessed (FIG. 1A).

Figure 1C:
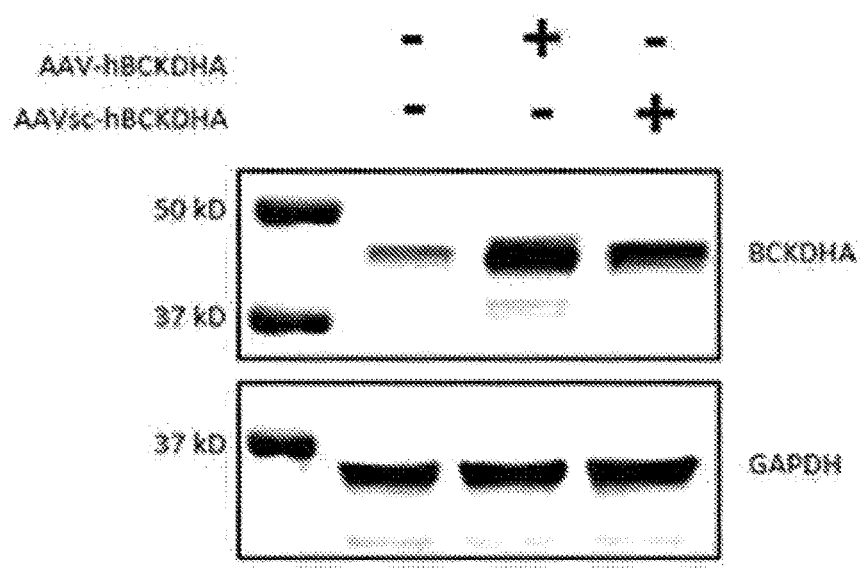
Figure 2A:
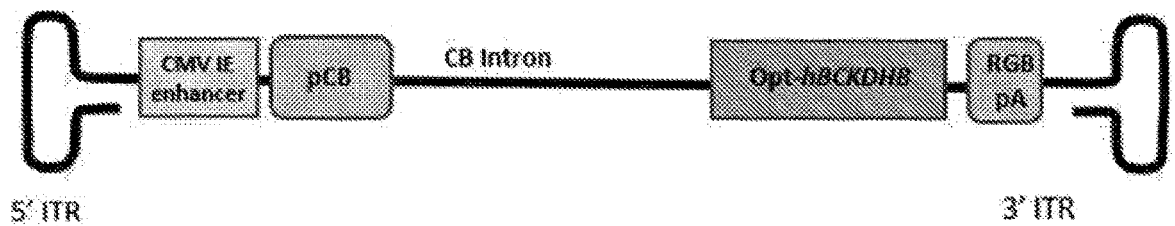
FIGS. 2A-2B depict AAV-constructs expressing BCKDHA and BCKDHB.
Figure 2A:
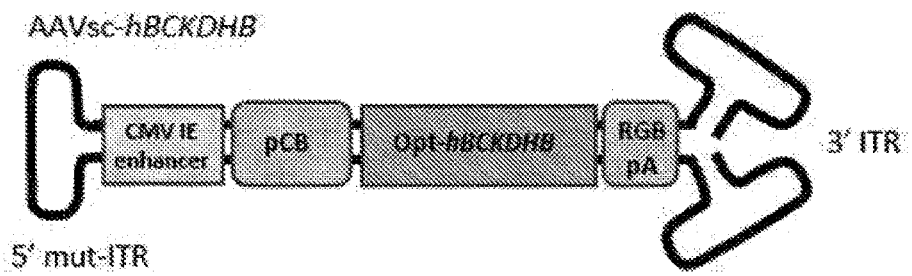
Figure 2B:
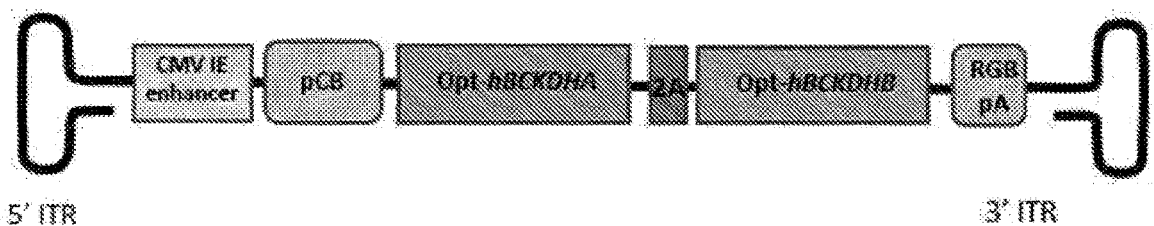
Figure 2B:
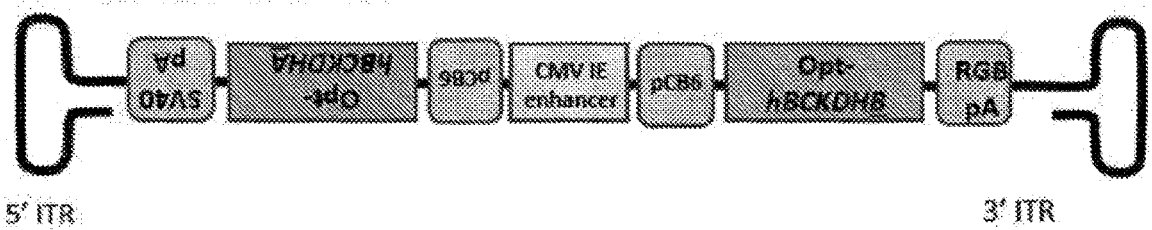

Recombinant AAV vectors were established that express a codon-optimized human BCKDHA gene (opti-BCKDHA; SEQ ID NO: 1). Full AAV and self-complementary vectors were developed (FIG. 1B). Protein expression was verified in various cell lines (FIG. 1C). The opti-BCKDHA cassette was packaged into AAV9 that, via systemic injection, efficiently targets the liver and skeletal muscle, where the endogenous BCKDHA is highly expressed in WT animals and normal human beings. Recombinant AAV9-opti-BCKDHA was delivered to wild type neonatal mice by systemic injection. Escalating doses were used to determine safety and efficacy of gene delivery.

Figure 3A:
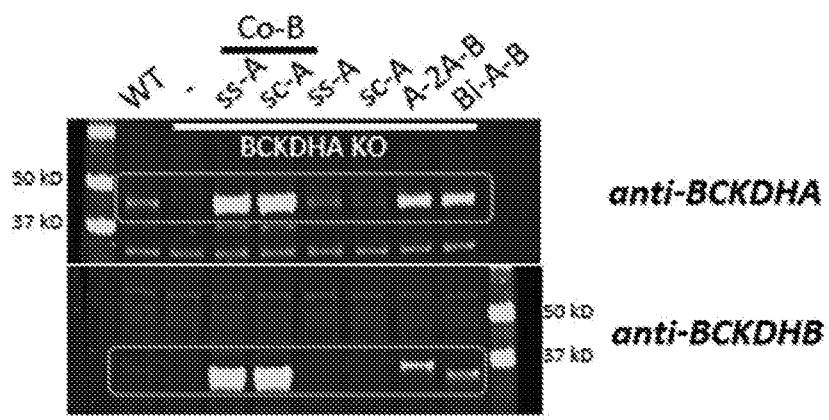
FIGS. 3A-3B depict AAV-constructs expression and activity test in HEK 293T cells.
Figure 3B:
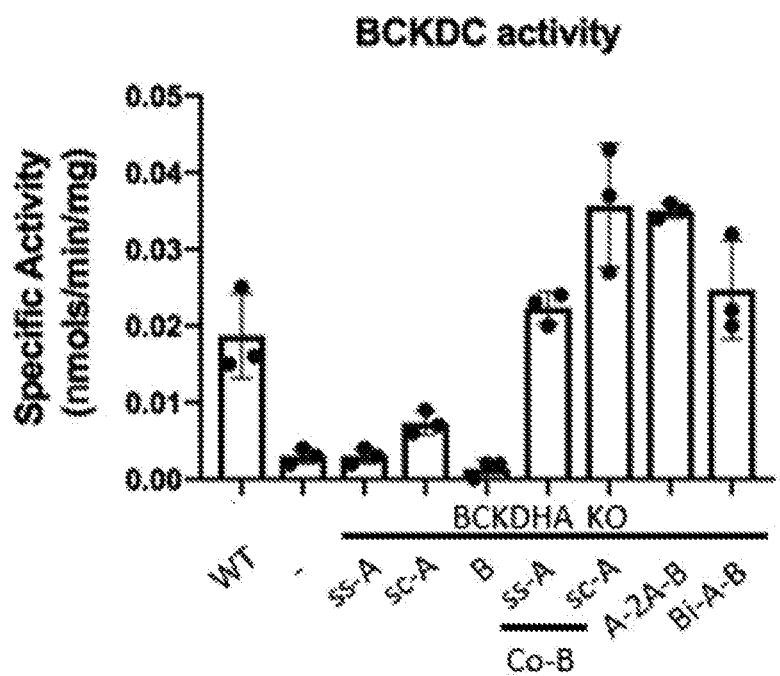

Example 2: Gene Therapy for Maple Syrup Urine Disease (MSUD) Caused by BCKDHA or BCKDHB Mutations The aim was to develop an AAV-mediated gene replacement therapy for MSUD caused by BCKDHA or BCKDHB biallellic mutations. AAV vectors expressing codon-optimized human BCKDHA gene (opti-BCKDHA; SEQ ID NO: 1) or BCKDHB gene (opti-BCKDHB; SEQ ID NO: 4), which encode E1-alpha and E1-beta subunits of BCKD complexes, respectively, were first designed. Considering the heterotetramer structure (alpha2-beta2, also known in the art as "α2β2") of functional BCKDC E1 component and that sole expression of BCKDHA or BCKDHB may not restore BCKDC enzyme activity efficiently, dual-vectors expressing BCKDHA and BCKDHB simultaneously were also designed (FIG. 1B and FIG. 2). The protein expression of these vectors were validated in HEK 293T cell line (FIG. 3A). Based on the BCKDC enzyme activity assay, it was found that these vectors are functional (FIG. 3B). The activity restoration is more efficient when BCKDHA and BCKDHB are co-expressed. The opti-BCKDHA, opti-BCKDHB, and dual-opti-BCKDHA/BCKDHB cassettes were packaged into AAV9 that, via systemic injection, efficiently targets the liver and skeletal muscle, tissues which exhibit highest BCKD activity in wild type animals and normal humans.

Figure 4D:
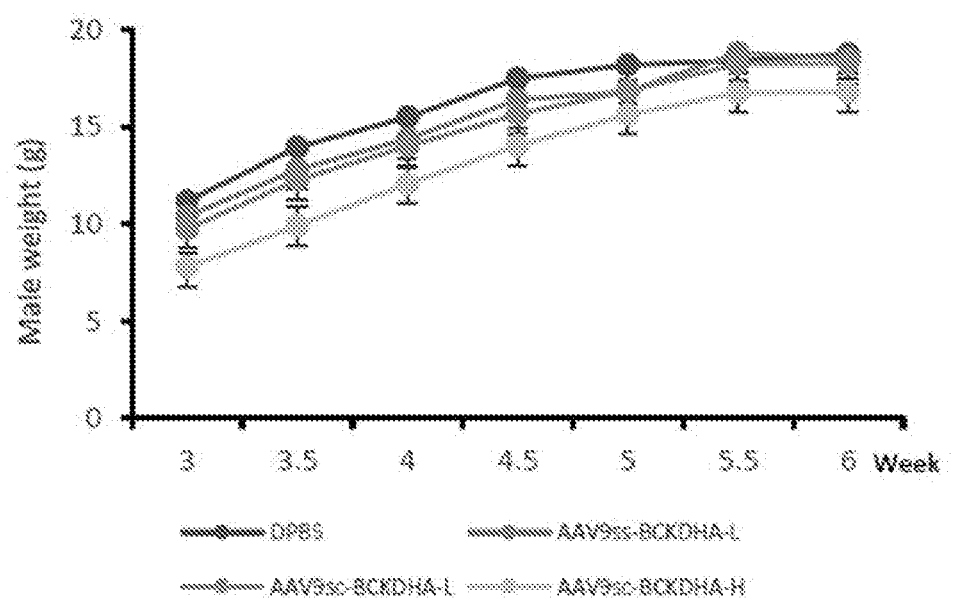
Figure 4E:
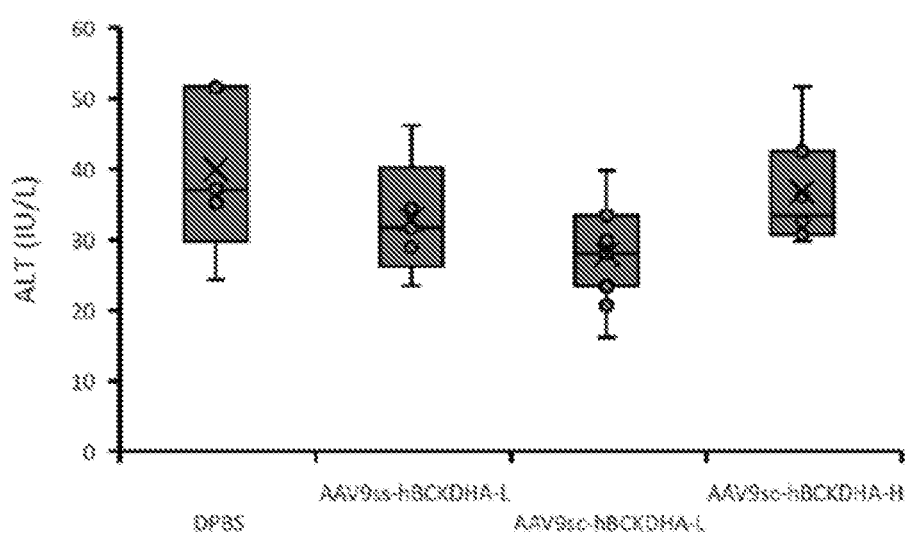
Figure 4F:
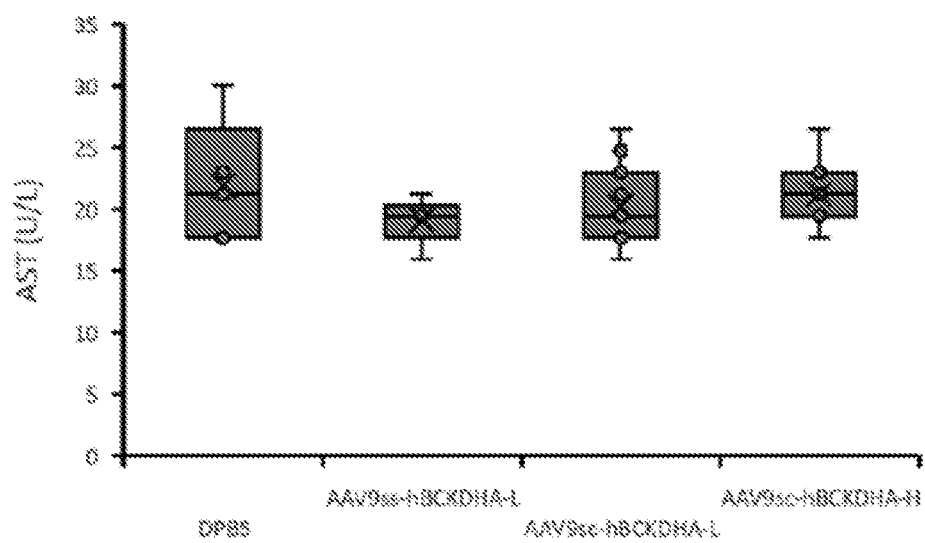

Recombinant AAV9 vectors expressing opti-BCKDHA or opti-BCKDHB were delivered into wild type neonatal mice by systemic injection and escalating doses were used to determine safety and efficiency of gene delivery (FIG. 4).

A strategy is provided herein to treat MSUD (MSUD) caused by BCKDHA or BCKDHB biallellic mutations. Dietary BCAA restriction is the mainstay of treatment but is difficult to implement, has imperfect efficacy, and affords no protection against episodic and life-threatening encephalopathic crises. Liver transplantation is an effective alternative to dietary therapy, but entails risks of surgery and long-term immunosuppression. In some embodiments, compared to previous treatment, BCKDHA and/or BCKDHB gene replacement therapy is a safer and more efficient option to treat MSUD. Considering the heterotetramer structure of functional E1 of BCKDC, the dual-vector expressing BCKDHA and BCKDHB at the same time may be a better and more efficient option for patients with BCKDHA or BCKDHB mutations.

OTHER EMBODIMENTS

Embodiment 1. A method for promoting expression of functional BCKDHA protein, which is the E1-alpha subunit of the branched-chain alpha-keto acid (BCAA) dehydrogenase complex, in a subject, the method comprising administering to the subject an effective amount of an rAAV comprising a capsid containing a nucleic acid engineered to express BCKDHA in the liver and/or skeletal muscle of the subject, wherein the subject comprises at least one endogenous BCKDHA allele having a loss-of-function mutation associated with Maple Syrup Urine Disease (MSUD).

Embodiment 2. The method of embodiment 1, wherein the at least one endogenous BCKDHA allele comprises a T-A transversion, resulting in a tyr394-to-asn (TYR394ASN).

Embodiment 3. The method of embodiment 1, wherein the at least one endogenous BCKDHA allele comprises a splice site mutation, a missense mutation, a truncation mutation, or a nonsense mutation.

Embodiment 4. The method of embodiment 1, wherein the subject has two endogenous BCKDHA alleles having the same loss-of-function mutations (homozygous state).

Embodiment 5. The method of embodiment 1, wherein the subject has two endogenous BCKDHA alleles having different loss-of-function mutations (compound heterozygous state).

Embodiment 6. The method of embodiment 1, wherein the endogenous BCKDHA allele comprises a 8 base pair deletion (887_894del).

Embodiment 7. The method of embodiment 1, wherein the endogenous BCKDHA allele comprises a 895G-A transition in exon 7, resulting in a gly245-to-arg (G245R) substitution.

Embodiment 8. The method of embodiment 1, wherein the endogenous BCKDHA allele comprises a 1253T-G transversion, resulting in a phe364-to-cys (F364C) substitution.

Embodiment 9. The method of embodiment 1, wherein the endogenous BCKDHA allele comprises a C-to-T transition resulting in an arg220-to-trp (R220W) substitution.

Embodiment 10. The method of embodiment 1, wherein the endogenous BCKDHA allele comprises a G-to-A transition resulting in a gly204-to-ser (G204S) substitution.

Embodiment 11. The method of embodiment 1, wherein the endogenous BCKDHA allele comprises a C-to-G transversion resulting in a thr265-to-arg (T265R) substitution.

Embodiment 12. The method of embodiment 1, wherein the endogenous BCKDHA allele comprises a C-to-G transversion in the BCKDHA gene, resulting in a cys219-to-trp (C219W) substitution.

Embodiment 13. The method of embodiment 1, wherein the endogenous BCKDHA allele comprises a 1 base pair deletion (117delC), resulting in a frameshift, encoding a truncated protein with only 61 residues.

Embodiment 14. The method of any one of embodiments 1-13, wherein administration is by systemic injection.

Embodiment 15. The method of any one of embodiments 1-14, wherein the capsid is an AAV9 capsid.

Embodiment 16. The method of any one of embodiments 1-15, wherein the nucleic acid is engineered to express a codon-optimized human BCKDHA gene (opti-BCKDHA).

Embodiment 17. The method of any one of embodiments 1-16, wherein the nucleic acid comprises a sequence as set forth in any one of SEQ ID NO: 1-3.

Embodiment 18. The method of any one of embodiments 1-17, wherein the nucleic acid comprises one or more ITRs, wherein each ITR is selected from the group consisting of AAV1 ITR, AAV2 ITR, AAV3 ITR, AAV4 ITR, AAV5 ITR, and AAV6 ITR.

Embodiment 19. The method of any one of embodiments 1-18, wherein the nucleic acid is a self-complementary AAV vector.

Embodiment 20. A method of treating a subject having Maple Syrup Urine Disease (MSUD), the method comprising administering to the subject an effective amount of an rAAV comprising a capsid containing a nucleic acid engineered to express BCKDHA in the liver and/or skeletal muscle of the subject.

Embodiment 21. An rAAV comprising, an AAV9 capsid containing a nucleic acid engineered to express BCKDHA in the liver and/or skeletal muscle of the subject.

Embodiment 22. A pharmaceutical composition comprising, the rAAV of embodiment 21.

Embodiment 23. An isolated nucleic acid comprising, a sequence as set forth by SEQ ID NO: 1-3.

Embodiment 24. A host cell comprising the isolated nucleic acid construct of embodiment 24.

Embodiment 25. The host cell of embodiment 24, wherein the cell is a eukaryotic cell.

Embodiment 26. The host cell of embodiment 25, further comprising, an isolated nucleic acid encoding an AAV capsid protein.

Embodiment 27. The host cell of embodiment 26, wherein the capsid protein is AAV9 capsid protein.

Embodiment 28. A method for promoting expression of functional BCKDHB protein, which is the E1-beta subunit of the branched-chain alpha-keto acid (BCAA) dehydrogenase complex, in a subject, the method comprising administering to the subject an effective amount of an rAAV comprising a capsid containing a nucleic acid engineered to express BCKDHB in the liver and/or skeletal muscle of the subject, wherein the subject comprises at least one endogenous BCKDHB allele having a loss-of-function mutation associated with Maple Syrup Urine Disease (MSUD).

Embodiment 29. The method of embodiment 28, wherein the at least one endogenous BCKDHB allele comprises, an 11 base pair deletion in exon 1.

Embodiment 30. The method of embodiment 28, wherein the at least one endogenous BCKDHB allele comprises, a guanine (G) to cytosine (C) change in exon 5, resulting in an arginine-to-proline substitution at residue 183 (R183P).

Embodiment 31. The method of embodiment 28, wherein the at least one endogenous BCKDHB allele comprises, a C to thymine (T) transition, resulting in a histidine-to-tyrosine substitution at residue 156 (H156Y).

Embodiment 32. The method of embodiment 28, wherein the at least one endogenous BCKDHB allele comprises, a T to G transversion, resulting in a valine-to-glycine substitution at residue 69 (V69G).

Embodiment 33. The method of embodiment 28, wherein the at least one endogenous BCKDHB allele comprises, a 4 base pair deletion in intron 9 resulting in the deletion of exon 10, and an 8 base pair insertion in exon 10 resulting in a frameshift.

Embodiment 34. The method of embodiment 28, wherein the at least one endogenous BCKDHB allele comprises, an 8 base pair insertion in exon 10.

Embodiment 35. The method of embodiment 28, wherein the at least one endogenous BCKDHB allele comprises a splice site mutation, a missense mutation, a truncation mutation, or a nonsense mutation.

Embodiment 36. The method of embodiment 28, wherein the subject has two endogenous BCKDHB alleles having the same loss-of-function mutations (homozygous state).

Embodiment 37. The method of embodiment 28, wherein the subject has two endogenous BCKDHB alleles having different loss-of-function mutations (compound heterozygous state).

Embodiment 38. The method of any one of embodiments 28-37, wherein administration is by systemic injection.

Embodiment 39. The method of any one of embodiments 28-38, wherein the capsid is an AAV9 capsid.

Embodiment 40. The method of any one of embodiments 28-39, wherein the nucleic acid is engineered to express a codon-optimized human BCKDHB gene (opti-BCKDHB).

Embodiment 41. The method of any one of embodiments 28-40, wherein the nucleic acid comprises a sequence as set forth in any one of SEQ ID NO: 4-6.

Embodiment 42. The method of any one of embodiments 28-41, wherein the nucleic acid comprises one or more ITRs, wherein each ITR is selected from the group consisting of AAV1 ITR, AAV2 ITR, AAV3 ITR, AAV4 ITR, AAV5 ITR, and AAV6 ITR.

Embodiment 43. The method of any one of embodiments 28-42, wherein the nucleic acid is a self-complementary AAV vector.

Embodiment 44. The method of embodiment 43, wherein the nucleic acid comprises a sequence as set forth in any one of SEQ ID NO: 7-8.

Embodiment 45. A method of treating a subject having Maple Syrup Urine Disease (MSUD), the method comprising administering to the subject an effective amount of an rAAV comprising a capsid containing a nucleic acid engineered to express BCKDHB in the liver and/or skeletal muscle of the subject.

Embodiment 46. An rAAV comprising an AAV9 capsid containing a nucleic acid engineered to express BCKDHB in the liver and/or skeletal muscle of the subject.

Embodiment 47. A pharmaceutical composition comprising the rAAV of embodiment 46.

Embodiment 48. An isolated nucleic acid comprising a sequence as set forth in any one of SEQ ID NO: 4-6.

Embodiment 49. An isolated nucleic acid comprising a sequence as set forth in any one of SEQ ID NO: 7-8.

Embodiment 50. A host cell comprising the isolated nucleic acid construct of any one of embodiments 48-49.

Embodiment 51. The host cell of embodiment 50, wherein the cell is a eukaryotic cell.

Embodiment 52. The host cell of embodiment 51, further comprising an isolated nucleic acid encoding an AAV capsid protein.

Embodiment 53. The host cell of embodiment 52, wherein the capsid protein is AAV9 capsid protein.

Embodiment 54. A method for promoting expression of functional BCKDHA and BCKDHB proteins, which are the E1-alpha and E1-beta subunits, respectively, of the branched-chain alpha-keto acid (BCAA) dehydrogenase complex, in a subject, the method comprising administering to the subject an effective amount of an rAAV comprising a capsid containing a nucleic acid engineered to express BCKDHA and BCKDHB in the liver and/or skeletal muscle of the subject, wherein the subject comprises at least one endogenous BCKDHA and/or at least one endogenous BCKDHB allele having a loss-of-function mutation associated with Maple Syrup Urine Disease (MSUD).

Embodiment 55. The method of embodiment 54, wherein the at least one endogenous BCKDHA allele comprises a T-A transversion, resulting in a tyr394-to-asn (TYR394ASN).

Embodiment 56. The method of embodiment 54, wherein the at least one endogenous BCKDHA allele comprises a splice site mutation, a missense mutation, a truncation mutation, or a nonsense mutation.

Embodiment 57. The method of embodiment 54, wherein the subject has two endogenous BCKDHA alleles having the same loss-of-function mutations (homozygous state).

Embodiment 58. The method of embodiment 54, wherein the subject has two endogenous BCKDHA alleles having different loss-of-function mutations (compound heterozygous state).

Embodiment 59. The method of embodiment 54, wherein the endogenous BCKDHA allele comprises a 8 base pair deletion (887_894del).

Embodiment 60. The method of embodiment 54, wherein the endogenous BCKDHA allele comprises a 895G-A transition in exon 7, resulting in a gly245-to-arg (G245R) substitution.

Embodiment 61. The method of embodiment 54, wherein the endogenous BCKDHA allele comprises a 1253T-G transversion, resulting in a phe364-to-cys (F364C) substitution.

Embodiment 62. The method of embodiment 54, wherein the endogenous BCKDHA allele comprises a C-to-T transition resulting in an arg220-to-trp (R220W) substitution.

Embodiment 63. The method of embodiment 54, wherein the endogenous BCKDHA allele comprises a G-to-A transition resulting in a gly204-to-ser (G204S) substitution.

Embodiment 64. The method of embodiment 54, wherein the endogenous BCKDHA allele comprises a C-to-G transversion resulting in a thr265-to-arg (T265R) substitution.

Embodiment 65. The method of embodiment 54, wherein the endogenous BCKDHA allele comprises a C-to-G transversion in the BCKDHA gene, resulting in a cys219-to-trp (C219W) substitution.

Embodiment 66. The method of embodiment 54, wherein the endogenous BCKDHA allele comprises a 1 base pair deletion (117delC), resulting in a frameshift, encoding a truncated protein with only 61 residues.

Embodiment 67. The method of embodiment 54, wherein the at least one endogenous BCKDHB allele comprises, an 11 base pair deletion in exon 1.

Embodiment 68. The method of embodiment 54, wherein the at least one endogenous BCKDHB allele comprises, a guanine (G) to cytosine (C) change in exon 5, resulting in an arginine-to-proline substitution at residue 183 (R183P).

Embodiment 69. The method of embodiment 54, wherein the at least one endogenous BCKDHB allele comprises, a C to thymine (T) transition, resulting in a histidine-to-tyrosine substitution at residue 156 (H156Y).

Embodiment 70. The method of embodiment 54, wherein the at least one endogenous BCKDHB allele comprises, a T to G transversion, resulting in a valine-to-glycine substitution at residue 69 (V69G).

Embodiment 71. The method of embodiment 54, wherein the at least one endogenous BCKDHB allele comprises, a 4 base pair deletion in intron 9 resulting in the deletion of exon 10, and an 8 base pair insertion in exon 10 resulting in a frameshift.

Embodiment 72. The method of embodiment 54, wherein the at least one endogenous BCKDHB allele comprises, an 8 base pair insertion in exon 10.

Embodiment 73. The method of embodiment 54, wherein the at least one endogenous BCKDHB allele comprises a splice site mutation, a missense mutation, a truncation mutation, or a nonsense mutation.

Embodiment 74. The method of embodiment 54, wherein the subject has two endogenous BCKDHB alleles having the same loss-of-function mutations (homozygous state).

Embodiment 75. The method of embodiment 54, wherein the subject has two endogenous BCKDHB alleles having different loss-of-function mutations (compound heterozygous state).

Embodiment 76. The method of any one of embodiments 54-75, wherein administration is by systemic injection.

Embodiment 77. The method of any one of embodiments 54-76, wherein the capsid is an AAV9 capsid.

Embodiment 78. The method of any one of embodiments 54-77, wherein the nucleic acid is engineered to express a codon-optimized human BCKDHB gene (opti-BCKDHB).

Embodiment 79. The method of any one of embodiments 54-78, wherein the nucleic acid comprises a sequence as set forth in any one of SEQ ID NO: 4-6.

Embodiment 80. The method of any one of embodiments 54-79, wherein the nucleic acid comprises one or more ITRs, wherein each ITR is selected from the group consisting of AAV1 ITR, AAV2 ITR, AAV3 ITR, AAV4 ITR, AAV5 ITR, and AAV6 ITR.

Embodiment 81. The method of any one of embodiments 54-80, wherein the nucleic acid is a self-complementary AAV vector.

Embodiment 82. The method of embodiment 81, wherein the nucleic acid comprises a sequence as set forth in any one of SEQ ID NO: 7-8.

Embodiment 83. A method of treating a subject having Maple Syrup Urine Disease (MSUD), the method comprising administering to the subject an effective amount of an rAAV comprising a capsid containing a nucleic acid engineered to express BCKDHA and BCKDHB in the liver and/or skeletal muscle of the subject.

Embodiment 84. An rAAV comprising an AAV9 capsid containing a nucleic acid engineered to express BCKDHA and BCKDHB in the liver and/or skeletal muscle of the subject.

Embodiment 85. A pharmaceutical composition comprising the rAAV of embodiment 84.

Embodiment 86. A host cell comprising the isolated nucleic acid construct of embodiment 85.

Embodiment 87. The host cell of embodiment 86, wherein the cell is a eukaryotic cell.

Embodiment 88. The host cell of embodiment 87, further comprising an isolated nucleic acid encoding an AAV capsid protein.

Embodiment 89. The host cell of embodiment 88, wherein the capsid protein is AAV9 capsid protein.

In addition to the embodiments expressly described herein, it is to be understood that all of the features disclosed in this disclosure may be combined in any combination (e.g., permutation, combination). Each element disclosed in the disclosure may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, and can make various changes and modifications of the invention to adapt it to various usages and conditions. Thus, other embodiments are also within the claims.

EQUIVALENTS AND SCOPE

It is to be understood that this disclosure is not limited to any or all of the particular embodiments described expressly herein, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents (i.e., any lexicographical definition in the publications and patents cited that is not also expressly repeated in the disclosure should not be treated as such and should not be read as defining any terms appearing in the accompanying claims). If there is a conflict between any of the incorporated references and this disclosure, this disclosure shall control. In addition, any particular embodiment of this disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

In the claims articles such as "a," "an," and "the" may mean one or more than one unless indicated to the contrary or otherwise evident from the context. Wherever used herein, a pronoun in a gender (e.g., masculine, feminine, neuter, other, etc. . . . ) the pronoun shall be construed as gender neutral (i.e., construed to refer to all genders equally) regardless of the implied gender unless the context clearly indicates or requires otherwise. Wherever used herein, words used in the singular include the plural, and words used in the plural includes the singular, unless the context clearly indicates or requires otherwise. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists (e.g., in Markush group format), each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included in such ranges unless otherwise specified. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the disclosure, as defined in the following claims.

What is claimed is:

1. A method for promoting expression of functional BCKDHA protein in a subject, the method comprising administering to the subject an rAAV comprising a capsid containing a nucleic acid engineered to express BCKDHA in the liver and/or skeletal muscle of the subject, wherein the subject comprises at least one BCKDHA allele having a loss-of-function mutation associated with Maple Syrup Urine Disease (MSUD);
   wherein the nucleic acid comprises the sequence set forth in SEQ ID NO: 1.

2. The method of claim 1, wherein the at least one BCKDHA allele comprises a T-A transversion, resulting in a tyr394-to-asn (TYR394ASN).

3. The method of claim 1, wherein the subject has two BCKDHA alleles having the same loss-of-function mutations or different loss-of-function mutations.

4. The method of claim 1, wherein the BCKDHA allele comprises an 8 base pair deletion.

5. The method of claim 1, wherein the BCKDHA allele comprises: (i) a 895G-A transition in exon 7, resulting in a gly245-to-arg (G245R) substitution; (ii) a 1253T-G transversion, resulting in a phe364-to-cys (F364C) substitution; (iii) a C-to-T transition resulting in an arg220-to-trp (R220W) substitution; (iv) a G-to-A transition resulting in a gly204-to-ser (G204S) substitution; (v) a C-to-G transversion resulting in a thr265-to-arg (T265R) substitution; or (vi) a C-to-G transversion, resulting in a cys219-to-trp (C219W) substitution.

6. The method of claim 1, wherein administration is by systemic injection.

7. The method of claim 1, wherein the capsid is an AAV9 capsid.

8. The method of claim 1, wherein the nucleic acid comprises one or more ITRs, wherein each ITR is selected from the group consisting of AAV1 ITR, AAV2 ITR, AAV3 ITR, AAV4 ITR, AAV5 ITR, and AAV6 ITR.

* * * * *

SEQUENCE LISTING

```
<160> NUMBER OF SEQ ID NOS: 10

<210> SEQ ID NO 1
<211> LENGTH: 1338
<212> TYPE: DNA
<213> ORGANISM: Artificial Sequence
<220> FEATURE:
<223> OTHER INFORMATION: Synthetic Polynucleotide

<400> SEQUENCE: 1
atggccgtcg caatcgccgc cgcaagagtg tggagactga atcggggact gagccaggcc      60
gcactgctgc tgctgagaca gccaggagcc agaggcctgg ccaggagcca cccacctagg     120
cagcagcagc agttcagctc cctggacgat aagccacagt ttcccggcgc ctctgccgag     180
ttcatcgaca agctggagtt tatccagcca aacgtgatca gcggcatccc catctaccgc     240
gtgatggacc ggcagggcca gatcatcaat ccatccgagg accccacct gccaaaggag     300 aaggtgctga agctgtacaa gtctatgacc ctgctgaaca caatggatag aatcctgtat     360
gagtcccagc gccaggccg gatctctttc tacatgacca actatggcga ggagggcaca     420
cacgtgggca gcgccgccgc cctggacaat accgatctgg tgttcggcca gtatagagag     480
gccggcgtgc tgatgtacag ggactatcct ctggagctgt ttatgccca gtgctacggc     540 aatatcagcg atcgggcaa gggccgccag atgccagtgc actatggctg taaggagcgg     600
cacttcgtga ccatctctag cccctggcc acacagatcc ctcaggcagt gggagcagcc     660
tacgccgcca agagagccaa cgccaatagg gtggtcatct gctattttgg agagggagca     720
gcctccgagg gcgacgcaca cgccggcttc aactttgccg ccaccctgga gtgccctatc     780
atcttctttt gtagaaacaa tggctacgcc atctctaccc caacaagcga gcagtatagg     840
ggcgatggaa tcgcagccag aggcccaggc tacggcatca tgtccatcag ggtggacggc     900
aacgacgtgt tcgccgtgta taatgccaca aaggaggcac ggagaagggc agtggcagag     960
```

| | |
|---|---:|
| aaccagccct ttctgatcga ggccatgacc tacagaatcg ccaccacag cacatccgac | 1020 |
| gattcctctg cctacaggtc tgtggacgaa gtgaattatt gggacaagca ggatcaccct | 1080 |
| atcagcagac tgaggcacta tctgctgtcc cagggctggt gggatgagga gcaggagaag | 1140 |
| gcctggagga agcagagccg ccggaaagtg atggaggcct cgagcaggc agagaggaag | 1200 |
| ccaaagccca accctaatct gctgtttccc gacgtgtacc aggagatgcc tgcccagctg | 1260 |
| aggaagcagc aggagagcct ggcaagacac ctgcagacat acggcgagca ttaccccctg | 1320 |
| gaccattttg ataagtga | 1338 |

<210> SEQ ID NO 2
<211> LENGTH: 6511
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---:|
| cgcgtggtac ctctagagtc gacccgggcg gcctcgagga cggggtgaac tacgcctgag | 60 |
| gatccgatct ttttccctct gccaaaaatt atggggacat catgaagccc cttgagcatc | 120 |
| tgacttctgg ctaataaagg aaatttattt tcattgcaat agtgtgttgg aattttttgt | 180 |
| gtctctcact cggaagcaat tcgttgatct gaatttcgac cacccataat acccattacc | 240 |
| ctggtagata agtagcatgg cgggttaatc attaactaca aggaacccct agtgatggag | 300 |
| ttggccactc cctctctgcg cgctcgctcg ctcactgagg ccgggcgacc aaaggtcgcc | 360 |
| cgacgcccgg gctttgcccg gcggcctca gtgagcgagc gagcgcgcag ccttaattaa | 420 |
| cctaattcac tggccgtcgt tttacaacgt cgtgactggg aaaaccctgg cgttacccaa | 480 |
| cttaatcgcc ttgcagcaca tccccctttc gccagctggc gtaatagcga agaggcccgc | 540 |
| accgatcgcc cttcccaaca gttgcgcagc ctgaatggcg aatgggacgc gccctgtagc | 600 |
| ggcgcattaa gcgcggcggg tgtggtggtt acgcgcagcg tgaccgctac acttgccagc | 660 |
| gccctagcgc ccgctccttt cgctttcttc ccttcctttc tcgccacgtt cgccggcttt | 720 |
| ccccgtcaag ctctaaatcg ggggctccct ttagggttcc gatttagtgc tttacggcac | 780 |
| ctcgacccca aaaaacttga ttagggtgat ggttcacgta gtgggccatc gccctgatag | 840 |
| acggtttttc gccctttgac gttggagtcc acgttcttta atagtggact cttgttccaa | 900 |
| actggaacaa cactcaaccc tatctcggtc tattcttttg atttataagg gattttgccg | 960 |
| atttcggcct attggttaaa aaatgagctg atttaacaaa aatttaacgc gaattttaac | 1020 |
| aaaatattaa cgcttacaat ttaggtggca cttttcgggg aaatgtgcgc ggaaccccta | 1080 |
| tttgtttatt tttctaaata cattcaaata tgtatccgct catgagacaa taaccctgat | 1140 |
| aaatgcttca ataatattga aaaggaaga gtatgagtat tcaacatttc cgtgtcgccc | 1200 |
| ttattccctt ttttgcggca ttttgccttc ctgtttttgc tcacccagaa acgctggtga | 1260 |
| aagtaaaaga tgctgaagat cagttgggtg cacgagtggg ttacatcgaa ctggatctca | 1320 |
| acagcggtaa gatccttgag agttttcgcc ccgaagaacg ttttccaatg atgagcactt | 1380 |
| ttaaagttct gctatgtggc gcggtattat cccgtattga cgccgggcaa gagcaactcg | 1440 |
| gtcgccgcat acactattct cagaatgact tggttgagta ctcaccagtc acagaaaagc | 1500 |
| atcttacgga tggcatgaca gtaagagaat tatgcagtgc tgccataacc atgagtgata | 1560 |
| acactgcggc caacttactt ctgacaacga tcggaggacc gaaggagcta accgcttttt | 1620 |

```
tgcacaacat gggggatcat gtaactcgcc ttgatcgttg ggaaccggag ctgaatgaag   1680
ccataccaaa cgacgagcgt gacaccacga tgcctgtagc aatggcaaca acgttgcgca   1740
aactattaac tggcgaacta cttactctag cttcccggca acaattaata gactggatgg   1800
aggcggataa agttgcagga ccacttctgc gctcggccct tccggctggc tggtttattg   1860
ctgataaatc tggagccggt gagcgtgggt ctcgcggtat cattgcagca ctggggccag   1920
atggtaagcc ctcccgtatc gtagttatct acacgacggg gagtcaggca actatggatg   1980
aacgaaatag acagatcgct gagataggtg cctcactgat taagcattgg taactgtcag   2040
accaagttta ctcatatata ctttagattg atttaaaact tcattttaa tttaaaagga   2100 tctaggtgaa gatcctttt gataatctca tgaccaaaat cccttaacgt gagttttcgt   2160
tccactgagc gtcagacccc gtagaaaaga tcaaaggatc ttcttgagat cctttttttc   2220
tgcgcgtaat ctgctgcttg caaacaaaaa aaccaccgct accagcggtg gtttgtttgc   2280
cggatcaaga gctaccaact ctttttccga aggtaactgg cttcagcaga gcgcagatac   2340
caaatactgt tcttctagtg tagccgtagt taggccacca cttcaagaac tctgtagcac   2400
cgcctacata cctcgctctg ctaatcctgt taccagtggc tgctgccagt ggcgataagt   2460
cgtgtcttac cgggttggac tcaagacgat agttaccgga taaggcgcag cggtcgggct   2520 gaacggggg ttcgtgcaca cagcccagct tggagcgaac gacctacacc gaactgagat   2580
acctacagcg tgagctatga gaaagcgcca cgcttcccga aggagaaag gcggacaggt   2640 atccggtaag cggcagggtc ggaacaggag agcgcacgag ggagcttcca gggggaaacg   2700
cctggtatct ttatagtcct gtcgggtttc gccacctctg acttgagcgt cgatttttgt   2760
gatgctcgtc aggggggcgg agcctatgga aaaacgccag caacgcggcc ttttacggt   2820 tcctggcctt ttgctggcct tttgctcaca tgttctttcc tgcgttatcc cctgattctg   2880
tggataaccg tattaccgcc tttgagtgag ctgataccgc tcgccgcagc cgaacgaccg   2940
agcgcagcga gtcagtgagc gaggaagcgg aagagcgccc aatacgcaaa ccgcctctcc   3000
ccgcgcgttg gccgattcat taatgcagct ggcacgacag gtttcccgac tggaaagcgg   3060
gcagtgagcg caacgcaatt aatgtgagtt agctcactca ttaggcaccc caggctttac   3120
actttatgct tccggctcgt atgttgtgtg gaattgtgag cggataacaa tttcacacag   3180
gaaacagcta tgaccatgat tacgccagat ttaattaagg ccttaattag ctgcgcgct   3240 cgctcgctca ctgaggccgc ccgggcaaag cccgggcgtc gggcgacctt tggtcgcccg   3300
gcctcagtga gcgagcgagc gcgcagagag ggagtggcca actccatcac taggggttcc   3360
ttgtagttaa tgattaaccc gccatgctac ttatctacca gggtaatggg gatcctctag   3420
aactatagct agtcgacatt gattattgac tagttattaa tagtaatcaa ttacggggtc   3480
attagttcat agcccatata tggagttccg cgttacataa cttacggtaa atggcccgcc   3540
tggctgaccg cccaacgacc cccgcccatt gacgtcaata atgacgtatg ttcccatagt   3600
aacgccaata gggactttcc attgacgtca atgggtggag tatttacggt aaactgccca   3660
cttggcagta catcaagtgt atcatatgcc aagtacgccc cctattgacg tcaatgacgg   3720
taaatggccc gcctggcatt atgcccagta catgacctta tgggactttc ctacttggca   3780
gtacatctac gtattagtca tcgctattac catggtcgag gtgagcccca cgttctgctt   3840
cactctcccc atctcccccc cctccccacc cccaattttg tatttattta ttttttaatt   3900
attttgtgca gcgatggggg cgggggggg gggggcgc gcgccaggcg gggcggggc   3960 gggcgagggg cggggcgggg cgaggcggag aggtgcggcg gcagccaatc agagcggcgc   4020
```

```
gctccgaaag tttccttta tggcgaggcg gcggcggcgg cggccctata aaaagcgaag    4080
cgcgcggcgg gcggggagtc gctgcgacgc tgccttcgcc ccgtgcccg ctccgccgcc    4140 gcctcgcgcc gcccgccccg gctctgactg accgcgttac tcccacaggt gagcgggcgg   4200
gacggcccct ctcctccggg ctgtaattag cgcttggttt aatgacggct tgtttctttt   4260
ctgtggctgc gtgaaagcct tgagggctc cgggagggcc ctttgtgcgg ggggagcggc    4320 tcgggggtg cgtgcgtgtg tgtgtgcgtg gggagcgccg cgtgcggctc cgcgctgccc     4380
ggcggctgtg agcgctgcgg gcgcggcgcg gggctttgtg cgctccgcag tgtgcgcgag    4440
gggagcgcgg ccggggcgg tgccccgcgg tgcgggggg gctgcgaggg gaacaaaggc     4500
tgcgtgcggg gtgtgtgcgt gggggggtga gcaggggtg tgggcgcgtc ggtcgggctg    4560 caacccccc tgcacccccc tccccgagtt gctgagcacg gcccggcttc gggtgcgggg    4620
ctccgtacgg ggcgtggcgc ggggctcgcc gtgccgggcg gggggtggcg gcaggtgggg   4680
gtgccgggcg gggcgggcc gcctcggcc ggggagggct cggggaggg gcgcggcggc      4740 ccccggagcg ccggcggctg tcgaggcgcg gcgagccgca gccattgcct tttatggtaa   4800
tcgtgcgaga gggcgcaggg acttcctttg tcccaaatct gtgcggagcc gaaatctggg   4860
aggcgccgcc gcaccccctc tagcgggcgc ggggcgaagc ggtgcggcgc cggcaggaag   4920
gaaatgggcg gggagggcct tcgtgcgtcg ccgcgccgcc gtcccttct ccctctccag    4980 cctcggggct gtccgcgggg ggacggctgc cttcggggg gacggggcag ggcggggttc    5040
ggcttctggc gtgtgaccgg cggctctaga gcctctgcta accatgttca tgccttcttc   5100
tttttcctac agctcctggg caacgtgctg gttattgtgc tgtctcatca ttttggcaaa   5160
gaattcgcca ccatggccgt cgcaatcgcc gccgcaagag tgtggagact gaatcgggga   5220
ctgagccagg ccgcactgct gctgctgaga cagccaggag ccagaggcct ggccaggagc   5280 caccccaccta ggcagcagca gcagttcagc tccctggacg ataagccaca gtttcccggc   5340
gcctctgccg agttcatcga caagctggag tttatccagc caaacgtgat cagcggcatc   5400
cccatctacc gcgtgatgga ccggcagggc cagatcatca tccatccga ggaccccac    5460 ctgccaaagg agaaggtgct gaagctgtac aagtctatga ccctgctgaa cacaatggat   5520
agaatcctgt atgagtccca gcgccagggc cggatctctt tctacatgac caactatggc   5580
gaggagggca cacacgtggg cagcgccgcc gcctggaca ataccgatct ggtgttcggc    5640
cagtatagag aggccggcgt gctgatgtac agggactatc ctctggagct gtttatggcc   5700
cagtgctacg gcaatatcag cgatctgggc aagggccgcc agatgccagt gcactatggc    5760
tgtaaggagc ggcacttcgt gaccatctct agcccctgg ccacacagat ccctcaggca    5820
gtgggagcag cctacgccgc caagagagcc aacgccaata gggtggtcat ctgctatttt   5880
ggagagggag cagcctccga gggcgacgca cacgccggct tcaactttgc cgccaccctg   5940
gagtgcccta tcatcttctt ttgtagaaac aatggctacg ccatctctac cccaacaagc   6000
gagcagtata ggggcgatgg aatcgcagcc agaggcccag gctacggcat catgtccatc   6060
agggtggacg gcaacgacgt gttcgccgtg tataatgcca caaggagggc acggagaagg    6120
gcagtggcag agaaccagcc cttttctgatc gaggccatga cctacagaat cggccaccac   6180
agcacatccg acgattcctc tgcctacagg tctgtggacg aagtgaatta ttgggacaag   6240
caggatcacc ctatcagcag actgaggcac tatctgctgt cccagggctg gtgggatgag   6300
gagcaggaga aggcctggag gaagcagagc cgccggaaag tgatggaggc cttcgagcag   6360
```

| | |
|---|---:|
| gcagagagga agccaaagcc caaccctaat ctgctgtttt ccgacgtgta ccaggagatg | 6420 |
| cctgcccagc tgaggaagca gcaggagagc ctggcaagac acctgcagac atacggcgag | 6480 |
| cattaccccc tggaccattt tgataagtga a | 6511 |

<210> SEQ ID NO 3
<211> LENGTH: 5282
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggata tttacggtaa | 360 |
| actgcccact tggcagtaca tcaagtgtat catatgccaa gtacgccccc tattgacgtc | 420 |
| aatgacggta aatggcccgc ctggcattat gcccagtaca tgaccttatg ggactttcct | 480 |
| acttggcagt acatctacgt attagtcatc gctattacca tgtcgaggcc acgttctgct | 540 |
| tcactctccc catctccccc ccctccccac cccaattttt gtatttattt attttttaat | 600 |
| tattttgtgc agcgatgggg gcggggggggg ggggcgcgcg ccaggcgggg cggggcgggg | 660 |
| cgaggggcgg ggcggggcga ggcggagagg tgcggcggca gccaatcaga gcggcgcgct | 720 |
| ccgaaagttt cctttatgg cgaggcggcg cggcggcgg ccctataaaa agcgaagcgc | 780 |
| gcggcgggcg ggagcaagct ctagcctcga ggccaccatg gccgtcgcaa tcgccgccgc | 840 |
| aagagtgtgg agactgaatc ggggactgag ccaggccgca ctgctgctgc tgagacagcc | 900 |
| aggagccaga ggcctggcca ggagccaccc acctaggcag cagcagcagt tcagctccct | 960 |
| ggacgataag ccacagtttc ccggcgcctc tgccgagttc atcgacaagc tggagtttat | 1020 |
| ccagccaaac gtgatcagcg gcatccccat ctaccgcgtg atggaccggc agggccagat | 1080 |
| catcaatcca tccgaggacc cccacctgcc aaaggagaag gtgctgaagc tgtacaagtc | 1140 |
| tatgaccctg ctgaacacaa tggatagaat cctgtatgag tcccagcgcc agggccggat | 1200 |
| ctcttttctac atgaccaact atggcgagga gggcacacac gtgggcagcg ccgccgccct | 1260 |
| ggacaatacc gatctggtgt tcggccagta tagagaggcc ggcgtgctga tgtacaggga | 1320 |
| ctatcctctg gagctgtttta tggcccagtc tacggcaat atcagcgatc tgggcaaggg | 1380 |
| ccgccagatg ccagtgcact atggctgtaa ggagcggcac ttcgtgacca tctctagccc | 1440 |
| cctggccaca cagatccctc aggcagtggg agcagcctac gccgccaaga gagccaacgc | 1500 |
| caatagggtg gtcatctgct atttggaga gggagcagcc tccgagggcg acgcacacgc | 1560 |
| cggcttcaac tttgccgcca ccctggagtg ccctatcatc ttcttttgta gaaacaatgg | 1620 |
| ctacgccatc tctaccccaa caagcgagca gtataggggc gatggaatcg cagccagagg | 1680 |
| cccaggctac ggcatcatgt ccatcagggt ggacggcaac gacgtgttcg ccgtgtataa | 1740 |
| tgccacaaag gaggcacgga aagggcagt ggcagagaac cagccctttc tgatcgaggc | 1800 |
| catgaccta agaatcggcc accacagcac atccgacgat tcctctgcct acaggtctgt | 1860 |
| ggacgaagtg aattattggg acaagcagga tcaccctatc agcagactga ggcactatct | 1920 |

| | |
|---|---|
| gctgtcccag ggctggtggg atgaggagca ggagaaggcc tggaggaagc agagccgccg | 1980 |
| gaaagtgatg gaggccttcg agcaggcaga gaggaagcca agcccaacc ctaatctgct | 2040 |
| gttttccgac gtgtaccagg agatgcctgc ccagctgagg aagcagcagg agagcctggc | 2100 |
| aagacacctg cagacatacg gcgagcatta ccccctggac cattttgata agtgaggatc | 2160 |
| cgatcttttt ccctctgcca aaaattatgg ggacatcatg aagccccttg agcatctgac | 2220 |
| ttctggctaa taaaggaaat ttattttcat tgcaatagtg tgttggaatt ttttgtgtct | 2280 |
| ctcactcggc ctaggtagat aagtagcatg gcgggttaat cattaactac aaggaacccc | 2340 |
| tagtgatgga gttggccact ccctctctgc gcgctcgctc gctcactgag gccgggcgac | 2400 |
| caaaggtcgc ccgacgcccg ggctttgccc gggcggcctc agtgagcgag cgagcgcgca | 2460 |
| gccttaatta acctaattca ctggccgtcg ttttacaacg tcgtgactgg gaaaaccctg | 2520 |
| gcgttaccca acttaatcgc cttgcagcac atccccctttt cgccagctgg cgtaatagcg | 2580 |
| aagaggcccg caccgatcgc ccttcccaac agttgcgcag cctgaatggc gaatgggacg | 2640 |
| cgccctgtag cggcgcatta agcgcggcgg gtgtggtggt tacgcgcagc gtgaccgcta | 2700 |
| cacttgccag cgccctagcg cccgctcctt tcgctttctt cccttccttt ctcgccacgt | 2760 |
| tcgccggctt tccccgtcaa gctctaaatc gggggctccc tttagggttc cgatttagtg | 2820 |
| ctttacggca cctcgacccc aaaaaacttg attagggtga tggttcacgt agtgggccat | 2880 |
| cgccctgata cacggttttt cgccctttga cgttggagtc cacgttcttt aatagtggac | 2940 |
| tcttgttcca aactggaaca cactcaacc ctatctcggt ctattctttt gatttataag | 3000 |
| ggattttgcc gatttcggcc tattggttaa aaaatgagct gatttaacaa aaatttaacg | 3060 |
| cgaattttaa caaaatatta acgcttacaa tttaggtggc acttttcggg gaaatgtgcg | 3120 |
| cggaacccct atttgtttat ttttctaaat acattcaaat atgtatccgc tcatgagaca | 3180 |
| ataaccctga taaatgcttc aataatattg aaaaaggaag agtatgagta ttcaacattt | 3240 |
| ccgtgtcgcc cttattccct ttttttgcggc attttgcctt cctgttttttg ctcacccaga | 3300 |
| aacgctggtg aaagtaaaag atgctgaaga tcagttgggt gcacgagtgg gttacatcga | 3360 |
| actggatctc aacagcggta agatccttga gagttttcgc cccgaagaac gttttccaat | 3420 |
| gatgagcact tttaaagttc tgctatgtgg cgcggtatta tcccgtattg acgccgggca | 3480 |
| agagcaactc ggtcgccgca tacactattc tcagaatgac ttggttgagt actcaccagt | 3540 |
| cacagaaaag catcttacgg atggcatgac agtaagagaa ttatgcagtg ctgccataac | 3600 |
| catgagtgat aacactgcgg ccaacttact tctgacaacg atcggaggac cgaaggagct | 3660 |
| aaccgctttt ttgcacaaca tgggggatca tgtaactcgc cttgatcgtt gggaaccgga | 3720 |
| gctgaatgaa gccataccaa acgacgagcg tgacaccacg atgcctgtag caatggcaac | 3780 |
| aacgttgcgc aaactattaa ctggcgaact acttactcta gcttcccggc aacaattaat | 3840 |
| agactggatg gaggcggata aagttgcagg accacttctg cgctcggccc ttccggctgg | 3900 |
| ctggtttatt gctgataaat ctggagccgg tgagcgtggg tctcgcggta tcattgcagc | 3960 |
| actggggcca gatggtaagc cctcccgtat cgtagttatc tacacgacgg ggagtcaggc | 4020 |
| aactatggat gaacgaaata gacagatcgc tgagataggt gcctcactga ttaagcattg | 4080 |
| gtaactgtca gaccaagttt actcatatat actttagatt gatttaaaac ttcattttta | 4140 |
| atttaaaagg atctaggtga agatcctttt tgataatctc atgaccaaaa tcccttaacg | 4200 |
| tgagttttcg ttccactgag cgtcagaccc cgtagaaaag atcaaaggat cttcttgaga | 4260 |

```
tccttttttt ctgcgcgtaa tctgctgctt gcaaacaaaa aaaccaccgc taccagcggt    4320
ggtttgtttg ccggatcaag agctaccaac tcttttccg aaggtaactg gcttcagcag     4380
agcgcagata ccaaatactg ttcttctagt gtagccgtag ttaggccacc acttcaagaa    4440
ctctgtagca ccgcctacat acctcgctct gctaatcctg ttaccagtgg ctgctgccag    4500
tggcgataag tcgtgtctta ccgggttgga ctcaagacga tagttaccgg ataaggcgca    4560
gcggtcgggc tgaacggggg gttcgtgcac acagcccagc ttggagcgaa cgacctacac    4620
cgaactgaga tacctacagc gtgagctatg agaaagcgcc acgcttcccg aagggagaaa    4680
ggcggacagg tatccggtaa gcggcagggt cggaacagga gagcgcacga gggagcttcc    4740
agggggaaac gcctggtatc tttatagtcc tgtcgggttt cgccacctct gacttgagcg    4800 tcgattttg tgatgctcgt caggggggcg gagcctatgg aaaaacgcca gcaacgcggc     4860 cttttacgg ttcctggcct tttgctggcc ttttgctcac atgttctttc ctgcgttatc     4920
ccctgattct gtggataacc gtattaccgc ctttgagtga gctgataccg ctcgccgcag    4980
ccgaacgacc gagcgcagcg agtcagtgag cgaggaagcg gaagagcgcc caatacgcaa    5040
accgcctctc cccgcgcgtt ggccgattca ttaatgcagc tggcacgaca ggtttcccga    5100
ctggaaagcg gcagtgagc gcaacgcaat taatgtgagt tagctcactc attaggcacc     5160
ccaggcttta cactttatgc ttccggctcg tatgttgtgt ggaattgtga gcggataaca    5220
atttcacaca ggaaacagct atgaccatga ttacgccaga tttaattaag gccttaatta    5280
gg                                                                   5282
```

<210> SEQ ID NO 4
<211> LENGTH: 1179
<212> TYPE: DNA
<213> ORGANISM: Artificial Sequence
<220> FEATURE:
<223> OTHER INFORMATION: Synthetic Polynucleotide

<400> SEQUENCE: 4

```
atggccgtgg tcgctgctgc tgccggatgg ctgctgagac tgcgggccgc tggggctgag      60
ggacattgga ggagactgcc tggggctggg ctggcaaggg gcttcctgca ccctgcagca    120
acagtggagg acgcagcaca gcggagacag gtggcccact tcacctttca gcccgatcct    180
gagccacgcg agtacggcca gacacagaag atgaacctgt ccagtccgt gacctctgcc     240 ctggacaata gcctggccaa ggatccaaca gccgtgatct ttggcgagga cgtggccttc    300
ggcggcgtgt tcggtgcac agtgggcctg agagacaagt acggcaagga tcgggtgttc     360
aacaccccac tgtgcgagca gggaatcgtg ggctttggca tcggcatcgc agtgaccgga    420
gcaacagcaa tcgcagagat ccagttcgcc gactatatct tccccgcctt tgatcagatc    480
gtgaacgagg ccgccaagta caggtatcgc tccggcgacc tgtttaattg cggcagcctg    540
accatcagat ccccttgggg atgcgtggga cacggcgccc tgtatcactc tcagagccca    600
gaggccttct ttgcccactg ccccggcatc aaggtggtca tcccacggag ccccttccag    660
gcaaagggcc tgctgctgtc ctgcatcgag gataagaacc cctgtatctt ctttgagcct    720
aagatcctgt acagagcagc agcagaggag gtgcctatcg agccatataa atcccctctg    780
tctcaggccg aagtgatcca ggagggaagc gacgtgaccc tggtggcatg ggaacacag     840 gtgcacgtga tcaggaggt ggcctccatg gccaaggaga gctgggcgt gtcttgcgaa      900 gtgatcgatc tgaggaccat catcccttgg gacgtggata caatctgtaa gtctgtgatc    960
aagaccggcc gcctgctgat cagccacgag gcaccactga caggaggatt cgcatccgag    1020
```

| | |
|---|---:|
| atcagctcca ccgtgcagga ggagtgcttt ctgaatctgg aggcccccaat ctctcgggtg | 1080 |
| tgcggctacg ataccccctt ccctcacatc tttgagcctt tctacatccc tgacaagtgg | 1140 |
| aagtgctacg acgctctgcg gaagatgatt aactattga | 1179 |

<210> SEQ ID NO 5
<211> LENGTH: 6352
<212> TYPE: DNA
<213> ORGANISM: Artificial Sequence
<220> FEATURE:
<223> OTHER INFORMATION: Synthetic Polynucleotide

<400> SEQUENCE: 5

| | |
|---|---:|
| cgcgtggtac ctctagagtc gacccgggcg gcctcgagga cggggtgaac tacgcctgag | 60 |
| gatccgatct ttttccctct gccaaaaatt atggggacat catgaagccc cttgagcatc | 120 |
| tgacttctgg ctaataaagg aaatttattt tcattgcaat agtgtgttgg aatttttgt | 180 |
| gtctctcact cggaagcaat tcgttgatct gaatttcgac cacccataat acccattacc | 240 |
| ctggtagata agtagcatgg cgggttaatc attaactaca aggaacccct agtgatggag | 300 |
| ttggccactc cctctctgcg cgctcgctcg ctcactgagg ccgggcgacc aaaggtcgcc | 360 |
| cgacgcccgg gctttgcccg gcggcctca gtgagcgagc gagcgcgcag ccttaattaa | 420 |
| cctaattcac tggccgtcgt tttacaacgt cgtgactggg aaaaccctgg cgttacccaa | 480 |
| cttaatcgcc ttgcagcaca tccccctttc gccagctggc gtaatagcga gaggcccgc | 540 |
| accgatcgcc cttcccaaca gttgcgcagc ctgaatggcg aatgggacgc gccctgtagc | 600 |
| ggcgcattaa gcgcggcggg tgtggtggtt acgcgcagcg tgaccgctac acttgccagc | 660 |
| gccctagcgc ccgctccttt cgctttcttc ccttcctttc tcgccacgtt cgccggcttt | 720 |
| ccccgtcaag ctctaaatcg ggggctccct ttagggttcc gatttagtgc tttacggcac | 780 |
| ctcgacccca aaaaacttga ttagggtgat ggttcacgta gtgggccatc gccctgatag | 840 |
| acggtttttc gccctttgac gttggagtcc acgttcttta atagtggact cttgttccaa | 900 |
| actggaacaa cactcaaccc tatctcggtc tattcttttg atttataagg gattttgccg | 960 |
| atttcggcct attggttaaa aaatgagctg atttaacaaa aatttaacgc gaattttaac | 1020 |
| aaaatattaa cgcttacaat ttaggtggca cttttcgggg aaatgtgcgc ggaaccccta | 1080 |
| tttgtttatt tttctaaata cattcaaata tgtatccgct catgagacaa taaccctgat | 1140 |
| aaatgcttca ataatattga aaaggaaga gtatgagtat tcaacatttc cgtgtcgccc | 1200 |
| ttattccctt ttttgcggca ttttgccttc ctgtttttgc tcacccagaa acgctggtga | 1260 |
| aagtaaaaga tgctgaagat cagttgggtg cacgagtggg ttacatcgaa ctggatctca | 1320 |
| acagcggtaa gatccttgag agttttcgcc ccgaagaacg ttttccaatg atgagcactt | 1380 |
| ttaaagttct gctatgtggc gcggtattat cccgtattga cgccgggcaa gagcaactcg | 1440 |
| gtcgccgcat acactattct cagaatgact tggttgagta ctcaccagtc acagaaaagc | 1500 |
| atcttacgga tggcatgaca gtaagagaat tatgcagtgc tgccataacc atgagtgata | 1560 |
| acactgcggc caacttactt ctgacaacga tcggaggacc gaaggagcta accgcttttt | 1620 |
| tgcacaacat gggggatcat gtaactcgcc ttgatcgttg gaaccggag ctgaatgaag | 1680 |
| ccataccaaa cgacgagcgt gacaccacga tgcctgtagc aatggcaaca acgttgcgca | 1740 |
| aactattaac tggcgaacta cttactctag cttcccggca acaattaata gactggatgg | 1800 |
| aggcggataa agttgcagga ccacttctgc gctcggccct tccggctggc tggtttattg | 1860 |

```
ctgataaatc tggagccggt gagcgtgggt ctcgcggtat cattgcagca ctggggccag   1920
atggtaagcc ctcccgtatc gtagttatct acacgacggg gagtcaggca actatggatg   1980
aacgaaatag acagatcgct gagataggtg cctcactgat taagcattgg taactgtcag   2040
accaagttta ctcatatata ctttagattg atttaaaact tcattttaa tttaaaagga    2100 tctaggtgaa gatccttttt gataatctca tgaccaaaat cccttaacgt gagttttcgt   2160
tccactgagc gtcagacccc gtagaaaaga tcaaaggatc ttcttgagat cctttttttc   2220
tgcgcgtaat ctgctgcttg caaacaaaaa aaccaccgct accagcggtg gtttgtttgc   2280
cggatcaaga gctaccaact cttttccga aggtaactgg cttcagcaga gcgcagatac    2340
caaatactgt tcttctagtg tagccgtagt taggccacca cttcaagaac tctgtagcac   2400
cgcctacata cctcgctctg ctaatcctgt taccagtggc tgctgccagt ggcgataagt   2460
cgtgtcttac cgggttggac tcaagacgat agttaccgga taaggcgcag cggtcgggct   2520 gaacggggggg ttcgtgcaca cagcccagct tggagcgaac gacctacacc gaactgagat   2580
acctacagcg tgagctatga gaaagcgcca cgcttcccga agggagaaag gcggacaggt   2640
atccggtaag cggcagggtc ggaacaggag agcgcacgag ggagcttcca gggggaaacg   2700
cctggtatct ttatagtcct gtcgggtttc gccacctctg acttgagcgt cgatttttgt   2760
gatgctcgtc aggggggcgg agcctatgga aaaacgccag caacgcggcc ttttacggt    2820 tcctggcctt ttgctggcct tttgctcaca tgttctttcc tgcgttatcc cctgattctg   2880
tggataaccg tattaccgcc tttgagtgag ctgataccgc tcgccgcagc cgaacgaccg   2940
agcgcagcga gtcagtgagc gaggaagcgg aagagcgccc aatacgcaaa ccgcctctcc   3000
ccgcgcgttg gccgattcat taatgcagct ggcacgacag gtttcccgac tggaaagcgg   3060
gcagtgagcg caacgcaatt aatgtgagtt agctcactca ttaggcaccc caggctttac   3120
actttatgct tccggctcgt atgttgtgtg gaattgtgag cggataacaa tttcacacag   3180
gaaacagcta tgaccatgat tacgccagat ttaattaagg ccttaattag ctgcgcgct    3240 cgctcgctca ctgaggccgc ccgggcaaag cccgggcgtc gggcgacctt tggtcgcccg   3300
gcctcagtga gcgagcgagc gcgcagagag ggagtggcca actccatcac tagggggttcc   3360 ttgtagttaa tgattaaccc gccatgctac ttatctacca gggtaatggg gatcctctag   3420
aactatagct agtcgacatt gattattgac tagttattaa tagtaatcaa ttacggggtc   3480
attagttcat agcccatata tggagttccg cgttacataa cttacggtaa atggcccgcc   3540
tggctgaccg cccaacgacc cccgcccatt gacgtcaata atgacgtatg ttcccatagt   3600
aacgccaata gggactttcc attgacgtca atgggtggag tatttacggt aaactgccca   3660
cttggcagta catcaagtgt atcatatgcc aagtacgccc cctattgacg tcaatgacgg   3720
taaatggccc gcctggcatt atgcccagta catgacctta tgggactttc ctacttggca   3780
gtacatctac gtattagtca tcgctattac catggtcgag gtgagcccca cgttctgctt   3840
cactctcccc atctccccc cctccccacc cccaatttg tatttattta ttttttaatt    3900
attttgtgca gcgatggggg cgggggggg ggggggcgc gcgccaggcg gggcggggcg     3960
gggcgagggg cggggcgggg cgaggcggag aggtgcggcg gcagccaatc agagcggcgc   4020
gctccgaaag tttcctttta tggcgaggcg gcggcggcgg cggccctata aaaagcgaag   4080
cgcgcggcgg gcggggagtc gctgcgacgc tgccttcgcc ccgtgccccg ctccgccgcc   4140
gcctcgcgcc gcccgccccg gctctgactg accgcgttac tcccacaggt gagcgggcgg   4200
gacggccctt ctcctccggg ctgtaattag cgcttggttt aatgacggct tgtttctttt   4260
```

```
ctgtggctgc gtgaaagcct tgagggctc cgggagggcc ctttgtgcgg ggggagcggc    4320
tcggggggtg cgtgcgtgtg tgtgtgcgtg gggagcgccg cgtgcggctc cgcgctgccc    4380
ggcggctgtg agcgctgcgg gcgcggcgcg gggctttgtg cgctccgcag tgtgcgcgag    4440
gggagcgcgg ccggggggcgg tgccccgcgcg tgcggggggg gctgcgaggg gaacaaaggc    4500
tgcgtgcggg gtgtgtgcgt gggggggtga gcagggggtg tgggcgcgtc ggtcgggctg    4560 caacccccc tgcacccccc tccccgagtt gctgagcacg gcccggcttc gggtgcgggg    4620
ctccgtacgg ggcgtggcgc ggggctcgcc gtgccgggcg gggggtggcg gcaggtgggg    4680
gtgccgggcg gggcggggcc gcctcgggcc gggagggct cggggagggg gcgcggcggc    4740
ccccggagcg ccggcggctg tcgaggcgcg gcgagccgca gccattgcct tttatggtaa    4800
tcgtgcgaga gggcgcaggg acttcctttg tcccaaatct gtgcggagcc gaaatctggg    4860
aggcgccgcc gcaccccctc tagcgggcgc ggggcgaagc ggtgcggcgc cggcaggaag    4920
gaaatgggcg gggagggcct tcgtgcgtcg ccgcgccgcc gtcccttct ccctctccag    4980 cctcggggct gtccgcgggg ggacggctgc cttcgggggg gacggggcag ggcggggttc    5040
ggcttctggc gtgtgaccgg cggctctaga gcctctgcta accatgttca tgccttcttc    5100 ttttttcctac agctcctggg caacgtgctg gttattgtgc tgtctcatca ttttggcaaa    5160
gaattcgcca ccatggccgt ggtcgctgct gctgccggat ggctgctgag actgcgggcc    5220
gctggggctg agggacattg gaggagactg cctggggctg ggctggcaag gggcttcctg    5280
caccctgcag caacagtgga ggacgcagca gcggagac aggtggccca cttcaccttt    5340
cagcccgatc ctgagccacg cgagtacggc cagacacaga agatgaacct gttccagtcc    5400
gtgacctctg ccctggacaa tagcctggcc aaggatccaa cagccgtgat ctttggcgag    5460
gacgtggcct tcggcggcgt gtttcggtgc acagtgggcc tgagagacaa gtacggcaag    5520
gatcgggtgt tcaacacccc actgtgcgag cagggaatcg tgggctttgg catcggcatc    5580
gcagtgaccg gagcaacagc aatcgcagag atccagttcg ccgactatat cttccccgcc    5640
tttgatcaga tcgtgaacga ggccgccaag tacaggtatc gctccggcga cctgtttaat    5700
tgcggcagcc tgaccatcag atcccctttgg ggatgcgtgg gacacggcgc cctgtatcac    5760
tctcagagcc cagaggcctt cttttgccac tgccccggca tcaaggtggt catcccacgg    5820
agccccttcc aggcaaaggg cctgctgctg tcctgcatcg aggataagaa cccctgtatc    5880
ttctttgagc ctaagatcct gtacagagca gcagcagagg aggtgcctat cgagccatat    5940
aatatccctc tgtctcaggc cgaagtgatc caggagggaa gcgacgtgac cctggtggca    6000
tggggaacac aggtgcacgt gatcagggag gtggcctcca tggccaagga aagctgggc    6060 gtgtcttgcg aagtgatcga tctgaggacc atcatccctt gggacgtgga tacaatctgt    6120
aagtctgtga tcaagaccgg ccgcctgctg atcagccacg aggcaccact gacaggagga    6180
ttcgcatccg agatcagctc caccgtgcag gaggagtgct ttctgaatct ggaggcccca    6240
atctctcggg tgtgcggcta cgataccccc ttccctcaca tctttgagcc tttctacatc    6300
cctgacaagt ggaagtgcta cgacgctctg cggaagatga ttaactattg aa           6352
```

<210> SEQ ID NO 6
<211> LENGTH: 5123
<212> TYPE: DNA
<213> ORGANISM: Artificial Sequence
<220> FEATURE:
<223> OTHER INFORMATION: Synthetic Polynucleotide

```
<400> SEQUENCE: 6
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt caattcacgc gtcgacattg attattgact agttattaat agtaatcaat    180
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggata tttacggtaa    360
actgcccact tggcagtaca tcaagtgtat catatgccaa gtacgccccc tattgacgtc    420
aatgacggta aatggcccgc ctggcattat gcccagtaca tgaccttatg ggactttcct    480
acttggcagt acatctacgt attagtcatc gctattacca tgtcgaggcc acgttctgct    540
tcactctccc catctccccc ccctccccac cccaattttt gtatttattt atttttttaat    600 tattttgtgc agcgatgggg gcgggggggg ggggcgcgcg ccaggcgggg cggggcgggg    660
cgaggggcgg ggcgggcgga ggcggagagg tgcggcggca gccaatcaga gcggcgcgct    720
ccgaaagttt ccttttatgg cgaggcggcg gcggcggcgg ccctataaaa agcgaagcgc    780
gcggcgggcg ggagcaagct ctagcctcga ggccaccatg gccgtggtcg ctgctgctgc    840
cggatggctg ctgagactgc gggccgctgg ggctgaggga cattggagga gactgcctgg    900
ggctgggctg gcaaggggct tcctgcaccc tgcagcaaca gtggaggacg cagcacagcg    960
gagacaggtg gcccacttca cctttcagcc cgatcctgag ccacgcgagt acggccagac   1020
acagaagatg aacctgttcc agtccgtgac ctctgccctg acaatagcc tggccaagga    1080 tccaacagcc gtgatctttg gcgaggacgt ggccttcggc ggcgtgtttc ggtgcacagt   1140
gggcctgaga gacaagtacg gcaaggatcg ggtgttcaac accccactgt gcgagcaggg   1200
aatcgtgggc tttggcatcg gcatcgcagt gaccggagca acagcaatcg cagagatcca   1260
gttcgccgac tatatcttcc ccgcctttga tcagatcgtg aacgaggccg ccaagtacag   1320
gtatcgctcc ggcgacctgt ttaattgcgg cagcctgacc atcagatccc cttggggatg   1380
cgtgggacac ggcgccctgt atcactctca gagcccagag gccttctttg cccactgccc   1440
cggcatcaag gtggtcatcc cacggagccc cttccaggca aagggcctgc tgctgtcctg   1500
catcgaggat aagaacccct gtatcttctt tgagcctaag atcctgtaca gagcagcagc   1560
agaggaggtg cctatcgagc catataatat ccctctgtct caggccgaag tgatccagga   1620
gggaagcgac gtgaccctgg tgcatgggg aacacaggtg cacgtgatca gggaggtggc   1680
ctccatggcc aaggagaagc tgggcgtgtc ttgcgaagtg atcgatctga ggaccatcat   1740
cccttgggac gtggatacaa tctgtaagtc tgtgatcaag accggccgcc tgctgatcag   1800
ccacgaggca ccactgacag gaggattcgc atccgagatc agctccaccg tgcaggagga   1860
gtgctttctg aatctggagg ccccaatctc tcgggtgtgc ggctacgata ccccttccc    1920 tcacatcttt gagcctttct acatccctga caagtggaag tgctacgacg ctctgcggaa   1980
gatgattaac tattgaggat ccgatctttt tccctctgcc aaaaattatg gggacatcat   2040
gaagcccctt gagcatctga cttctggcta ataaggaaa tttattttca ttgcaatagt    2100
gtgttggaat ttttttgtgtc tctcactcgg cctaggtaga taagtagcat ggcgggttaa   2160
tcattaacta caaggaaccc ctagtgatgg agttggccac tccctctctg cgcgctcgct   2220
cgctcactga ggccgggcga ccaaaggtcg cccgacgccc gggctttgcc cggcggcct    2280 cagtgagcga gcgagcgcgc agccttaatt aacctaattc actggccgtc gttttacaac   2340
```

```
gtcgtgactg ggaaaaccct ggcgttaccc aacttaatcg ccttgcagca catccccctt    2400
tcgccagctg gcgtaatagc gaagaggccc gcaccgatcg cccttcccaa cagttgcgca    2460
gcctgaatgg cgaatgggac gcgccctgta gcggcgcatt aagcgcggcg ggtgtggtgg    2520
ttacgcgcag cgtgaccgct acacttgcca gcgccctagc gcccgctcct ttcgctttct    2580
tcccttcctt tctcgccacg ttcgccggct ttccccgtca agctctaaat cgggggctcc    2640
ctttagggtt ccgatttagt gctttacggc acctcgaccc caaaaaactt gattagggtg    2700
atggttcacg tagtgggcca tcgccctgat agacggtttt tcgccctttg acgttggagt    2760
ccacgttctt taatagtgga ctcttgttcc aaactggaac aacactcaac cctatctcgg    2820
tctattcttt tgatttataa gggattttgc cgatttcggc ctattggtta aaaaatgagc    2880
tgatttaaca aaaatttaac gcgaatttta acaaaatatt aacgcttaca atttaggtgg    2940
cacttttcgg ggaaatgtgc gcggaaccc tatttgttta tttttctaaa tacattcaaa    3000
tatgtatccg ctcatgagac aataaccctg ataaatgctt caataatatt gaaaaaggaa    3060
gagtatgagt attcaacatt tccgtgtcgc ccttattccc ttttttgcgg cattttgcct    3120
tcctgttttt gctcacccag aaacgctggt gaaagtaaaa gatgctgaag atcagttggg    3180
tgcacgagtg ggttacatcg aactggatct caacagcggt aagatccttg agagttttcg    3240
ccccgaagaa cgttttccaa tgatgagcac ttttaaagtt ctgctatgtg gcgcggtatt    3300
atcccgtatt gacgccgggc aagagcaact cggtcgccgc atacactatt ctcagaatga    3360
cttggttgag tactcaccag tcacagaaaa gcatcttacg gatggcatga cagtaagaga    3420
attatgcagt gctgccataa ccatgagtga taacactgcg gccaacttac ttctgacaac    3480
gatcggagga ccgaaggagc taaccgcttt tttgcacaac atgggggatc atgtaactcg    3540
ccttgatcgt tgggaaccgg agctgaatga agccatacca aacgacgagc gtgacaccac    3600
gatgcctgta gcaatggcaa caacgttgcg caaactatta actggcgaac tacttactct    3660
agcttcccgg caacaattaa tagactggat ggaggcggat aaagttgcag gaccacttct    3720
gcgctcggcc cttccggctg gctggtttat tgctgataaa tctggagccg gtgagcgtgg    3780
gtctcgcggt atcattgcag cactggggcc agatggtaag ccctcccgta tcgtagttat    3840
ctacacgacg gggagtcagg caactatgga tgaacgaaat agacagatcg ctgagatagg    3900
tgcctcactg attaagcatt ggtaactgtc agaccaagtt tactcatata cttttagat    3960 tgatttaaaa cttcattttt aatttaaaag gatctaggtg aagatccttt ttgataatct    4020
catgaccaaa atcccttaac gtgagttttc gttccactga gcgtcagacc ccgtagaaaa    4080
gatcaaagga tcttcttgag atcctttttt tctgcgcgta atctgctgct tgcaaacaaa    4140
aaaaccaccg ctaccagcgg tggtttgttt gccggatcaa gagctaccaa ctctttttcc    4200
gaaggtaact ggcttcagca gagcgcagat accaaatact gttcttctag tgtagccgta    4260
gttaggccac cacttcaaga actctgtagc accgcctaca tacctcgctc tgctaatcct    4320
gttaccagtg gctgctgcca gtggcgataa gtcgtgtctt accgggttgg actcaagacg    4380
atagttaccg gataaggcgc agcggtcggg ctgaacgggg ggttcgtgca cacagcccag    4440
cttggagcga acgacctaca ccgaactgag atacctacag cgtgagctat gagaaagcgc    4500
cacgcttccc gaagggagaa aggcggacag gtatccggta agcggcaggg tcggaacagg    4560
agagcgcacg agggagcttc caggggggaaa cgcctggtat ctttatagtc ctgtcgggtt    4620
tcgccacctc tgacttgagc gtcgattttt gtgatgctcg tcaggggggc ggagcctatg    4680
```

| | |
|---|---|
| gaaaaacgcc agcaacgcgg ccttttacg gttcctggcc ttttgctggc cttttgctca | 4740 |
| catgttcttt cctgcgttat cccctgattc tgtggataac cgtattaccg cctttgagtg | 4800 |
| agctgatacc gctcgccgca gccgaacgac cgagcgcagc gagtcagtga gcgaggaagc | 4860 |
| ggaagagcgc ccaatacgca aaccgcctct ccccgcgcgt tggccgattc attaatgcag | 4920 |
| ctggcacgac aggtttcccg actggaaagc gggcagtgag cgcaacgcaa ttaatgtgag | 4980 |
| ttagctcact cattaggcac cccaggcttt acactttatg cttccggctc gtatgttgtg | 5040 |
| tggaattgtg agcggataac aatttcacac aggaaacagc tatgaccatg attacgccag | 5100 |
| atttaattaa ggccttaatt agg | 5123 |

<210> SEQ ID NO 7
<211> LENGTH: 6782
<212> TYPE: DNA
<213> ORGANISM: Artificial Sequence
<220> FEATURE:
<223> OTHER INFORMATION: Synthetic Polynucleotide

<400> SEQUENCE: 7

| | |
|---|---|
| cgcgtggtac ctctagagtc gacccgggcg gcctcgagga cggggtgaac tacgcctgag | 60 |
| gatccgatct ttttcctct gccaaaaatt atggggacat catgaagccc ttgagcatc | 120 |
| tgacttctgg ctaataaagg aaatttattt tcattgcaat agtgtgttgg aatttttgt | 180 |
| gtctctcact cggaagcaat tcgttgatct gaatttcgac cacccataat acccattacc | 240 |
| ctggtagata agtagcatgg cgggttaatc attaactaca aggaacccct agtgatggag | 300 |
| ttggccactc cctctctgcg cgctcgctcg ctcactgagg ccgggcgacc aaaggtcgcc | 360 |
| cgacgcccgg gctttgcccg gcggcctca gtgagcgagc gagcgcgcag ccttaattaa | 420 |
| cctaattcac tggccgtcgt tttacaacgt cgtgactggg aaaaccctgg cgttacccaa | 480 |
| cttaatcgcc ttgcagcaca tccccctttc gccagctggc gtaatagcga agaggcccgc | 540 |
| accgatcgcc cttcccaaca gttgcgcagc ctgaatggcg aatgggacgc gccctgtagc | 600 |
| ggcgcattaa gcgcggcggg tgtggtggtt acgcgcagcg tgaccgctac acttgccagc | 660 |
| gccctagcgc ccgctccttt cgctttcttc ccttcctttc tcgccacgtt cgccggcttt | 720 |
| ccccgtcaag ctctaaatcg ggggctccct ttagggttcc gatttagtgc tttacggcac | 780 |
| ctcgacccca aaaaacttga ttagggtgat ggttcacgta gtgggccatc gccctgatag | 840 |
| acggttttc gccctttgac gttggagtcc acgttcttta atagtggact cttgttccaa | 900 |
| actggaacaa cactcaaccc tatctcggtc tattcttttg atttataagg gattttgccg | 960 |
| atttcggcct attggttaaa aaatgagctg atttaacaaa aatttaacgc gaattttaac | 1020 |
| aaaatattaa cgcttacaat ttaggtggca cttttcgggg aaatgtgcgc ggaacccta | 1080 |
| tttgtttatt tttctaaata cattcaaata tgtatccgct catgagacaa taaccctgat | 1140 |
| aaatgcttca ataatattga aaaggaaga gtatgagtat tcaacatttc cgtgtcgccc | 1200 |
| ttattcccct ttttgcggca ttttgccttc ctgtttttgc tcacccagaa acgctggtga | 1260 |
| aagtaaaaga tgctgaagat cagttgggtg cacgagtggg ttacatcgaa ctggatctca | 1320 |
| acagcggtaa gatccttgag agttttcgcc ccgaagaacg ttttccaatg atgagcactt | 1380 |
| ttaaagttct gctatgtggc gcggtattat cccgtattga cgccgggcaa gagcaactcg | 1440 |
| gtcgccgcat acactattct cagaatgact tggttgagta ctcaccagtc acagaaaagc | 1500 |
| atcttacgga tggcatgaca gtaagagaat tatgcagtgc tgccataacc atgagtgata | 1560 |
| acactgcggc caacttactt ctgacaacga tcggaggacc gaaggagcta accgcttttt | 1620 |

```
tgcacaacat gggggatcat gtaactcgcc ttgatcgttg ggaaccggag ctgaatgaag    1680
ccataccaaa cgacgagcgt gacaccacga tgcctgtagc aatggcaaca acgttgcgca    1740
aactattaac tggcgaacta cttactctag cttcccggca acaattaata gactggatgg    1800
aggcggataa agttgcagga ccacttctgc gctcggccct tccggctggc tggtttattg    1860
ctgataaatc tggagccggt gagcgtgggt ctcgcggtat cattgcagca ctggggccag    1920
atggtaagcc ctcccgtatc gtagttatct acacgacggg gagtcaggca actatggatg    1980
aacgaaatag acagatcgct gagataggtg cctcactgat taagcattgg taactgtcag    2040
accaagttta ctcatatata ctttagattg atttaaaact tcattttttaa tttaaaagga    2100 tctaggtgaa gatccttttt gataatctca tgaccaaaat cccttaacgt gagttttcgt    2160
tccactgagc gtcagacccc gtagaaaaga tcaaaggatc ttcttgagat ccttttttc     2220 tgcgcgtaat ctgctgcttg caaacaaaaa aaccaccgct accagcggtg gtttgtttgc    2280
cggatcaaga gctaccaact ctttttccga aggtaactgg cttcagcaga gcgcagatac    2340
caaatactgt tcttctagtg tagccgtagt taggccacca cttcaagaac tctgtagcac    2400
cgcctacata cctcgctctg ctaatcctgt taccagtggc tgctgccagt ggcgataagt    2460
cgtgtcttac cgggttggac tcaagacgat agttaccgga taaggcgcag cggtcgggct    2520 gaacggggg ttcgtgcaca cagcccagct tggagcgaac gacctacacc gaactgagat    2580
acctacagcg tgagctatga gaaagcgcca cgcttcccga agggagaaag gcggacaggt    2640
atccggtaag cggcagggtc ggaacaggag agcgcacgag ggagcttcca gggggaaacg    2700
cctggtatct ttatagtcct gtcgggtttc gccacctctg acttgagcgt cgatttttgt    2760
gatgctcgtc aggggggcgg agcctatgga aaaacgccag caacgcggcc ttttttacggt    2820 tcctggcctt ttgctggcct tttgctcaca tgttctttcc tgcgttatcc cctgattctg    2880
tggataaccg tattaccgcc tttgagtgag ctgataccgc tcgccgcagc cgaacgaccg    2940
agcgcagcga gtcagtgagc gaggaagcgg aagagcgccc aatacgcaaa ccgcctctcc    3000
ccgcgcgttg gccgattcat taatgcagct ggcacgacag gtttcccgac tggaaagcgg    3060
gcagtgagcg caacgcaatt aatgtgagtt agctcactca ttaggcaccc caggctttac    3120
actttatgct tccggctcgt atgttgtgtg gaattgtgag cggataacaa tttcacacag    3180
gaaacagcta tgaccatgat tacgccagat ttaattaagg ccttaattag gctgcgcgct    3240
cgctcgctca ctgaggccgc ccgggcaaag cccgggcgtc gggcgacctt ggtcgcccg     3300 gcctcagtga gcgagcgagc gcgcagagag ggagtggcca actccatcac tagggggttcc   3360 ttgtagttaa tgattaaccc gccatgctac ttatctacca gggtaatggg gatcctctag    3420
aactatagct agtcgacatt gattattgac tagttattaa tagtaatcaa ttacggggtc    3480
attagttcat agcccatata tggagttccg cgttacataa cttacggtaa atggcccgcc    3540
tggctgaccg cccaacgacc cccgcccatt gacgtcaata atgacgtatg ttcccatagt    3600
aacgccaata gggactttcc attgacgtca atgggtggag tatttacggt aaactgccca    3660
cttggcagta catcaagtgt atcatatgcc aagtacgccc cctattgacg tcaatgacgg    3720
taaatggccc gcctggcatt atgcccagta catgacctta tgggactttc ctacttggca    3780
gtacatctac gtattagtca tcgctattac catggtcgag gtgagcccca cgttctgctt    3840
cactctcccc atctcccccc cctccccacc cccaatttg tatttattta ttttttaatt     3900
attttgtgca gcgatggggg cggggggggg ggggggcgc gcgccaggcg gggcggggcg     3960
```

```
gggcgagggg cggggcgggg cgaggcggag aggtgcggcg gcagccaatc agagcggcgc    4020
gctccgaaag tttcctttta tggcgaggcg cggcggcgg cggccctata aaaagcgaag     4080
cgcgcggcgg gcggggagtc gctgcgacgc tgccttcgcc ccgtgccccg ctccgccgcc    4140
gcctcgcgcc gcccgcccg gctctgactg accgcgttac tcccacgcca ccatggccgt     4200
ggtcgctgct gctgccggat ggctgctgag actgcgggcc gctgggctg agggacattg     4260 gaggagactg cctggggctg ggctggcaag gggcttcctg caccctgcag caacagtgga    4320
ggacgcagca cagcggagac aggtggccca cttcaccttt cagcccgatc ctgagccacg    4380
cgagtacggc cagacacaga agatgaacct gttccagtcc gtgacctctg ccctggacaa    4440
tagcctggcc aaggatccaa cagccgtgat ctttggcgag gacgtggcct cggcggcgt     4500 gtttcggtgc acagtgggcc tgagagacaa gtacggcaag gatcgggtgt tcaacacccc    4560
actgtgcgag cagggaatcg tgggctttgg catcggcatc gcagtgaccg gagcaacagc    4620
aatcgcagag atccagttcg ccgactatat cttccccgcc tttgatcaga tcgtgaacga    4680
ggccgccaag tacaggtatc gctccggcga cctgtttaat tgcggcagcc tgaccatcag    4740 atcccccttgg ggatgcgtgg gacacggcgc cctgtatcac tctcagagcc cagaggcctt    4800 cttttgcccac tgcccccggca tcaaggtggt catcccacgg agcccctcc aggcaaaggg     4860 cctgctgctg tcctgcatcg aggataagaa ccccctgtatc ttctttgagc ctaagatcct    4920
gtacagagca gcagcagagg aggtgcctat cgagccatat aatatccctc tgtctcaggc    4980
cgaagtgatc caggagggaa gcgacgtgac cctggtggca tggggaacac aggtgcacgt    5040
gatcagggag gtggcctcca tggccaagga gaagctgggc gtgtcttgcg aagtgatcga    5100
tctgaggacc atcatccctt gggacgtgga tacaatctgt aagtctgtga tcaagaccgg    5160
ccgcctgctg atcagccacg aggcaccact gacaggagga ttcgcatccg agatcagctc    5220
caccgtgcag gaggagtgct ttctgaatct ggaggcccca atctctcggg tgtgcggcta    5280
cgataccccc ttccctcaca tctttgagcc tttctacatc cctgacaagt ggaagtgcta    5340
cgacgctctg cggaagatga ttaactatgg atccggtgag ggcagaggaa gtcttctaac    5400
atgcggtgac gtggaggaga atccgggccc tgaattcgcc accatggccg tcgcaatcgc    5460
cgccgcaaga gtgtggagac tgaatcgggg actgagccag gccgcactgc tgctgctgag    5520
acagccagga gccagaggcc tggccaggag ccacccacct aggcagcagc agcagttcag    5580
ctccctggac gataagccac agtttcccgg cgcctctgcc gagttcatcg acaagctgga    5640
gtttatccag ccaaacgtga tcagcggcat ccccatctac cgcgtgatgg accggcaggg    5700
ccagatcatc aatccatccg aggaccccca cctgccaaag gagaaggtgc tgaagctgta    5760
caagtctatg accctgctga acacaatgga tagaatcctg tatgagtccc agcgccaggg    5820
ccggatctct ttctacatga ccaactatgg cgaggagggc acacacgtgg gcagcgccgc    5880
cgccctggac aataccgatc tggtgttcgg ccagtataga gaggccggcg tgctgatgta    5940
cagggactat cctctggagc tgtttatggc ccagtgctac ggcaatatca gcgatctggg    6000
caagggccgc cagatgccag tgcactatgg ctgtaaggag cggcacttcg tgaccatctc    6060 tagcccctg gccacacaga tccctcaggc agtgggagca gcctacgccg ccaagagagc    6120
caacgccaat agggtggtca tctgctattt tggagaggga gcagcctccg agggcgacgc    6180
acacgccggc ttcaactttg ccgccaccct ggagtgccct atcatcttct tttgtagaaa    6240
caatggctac gccatctcta ccccaacaag cgagcagtat aggggcgatg gaatcgcagc    6300
cagaggccca ggctacggca tcatgtccat caggtggac ggcaacgacg tgttcgccgt    6360
```

| | |
|---|---|
| gtataatgcc acaaaggagg cacggagaag ggcagtggca gagaaccagc cctttctgat | 6420 |
| cgaggccatg acctacagaa tcggccacca cagcacatcc gacgattcct ctgcctacag | 6480 |
| gtctgtggac gaagtgaatt attgggacaa gcaggatcac cctatcagca gactgaggca | 6540 |
| ctatctgctg tcccagggct ggtgggatga ggagcaggag aaggcctgga ggaagcagag | 6600 |
| ccgccggaaa gtgatggagg ccttcgagca ggcagagagg aagccaaagc ccaaccctaa | 6660 |
| tctgctgttt tccgacgtgt accaggagat gcctgcccag ctgaggaagc agcaggagag | 6720 |
| cctggcaaga cacctgcaga catacggcga gcattacccc ctggaccatt ttgataagtg | 6780 |
| aa | 6782 |

<210> SEQ ID NO 8
<211> LENGTH: 6971
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctagatc tgaattctac cacatttgta gaggttttac | 180 |
| ttgctttaaa aaacctccca catctccccc tgaacctgaa acataaaatg aatgcaattg | 240 |
| ttgttgttaa cttgtttatt gcagcttata atggttacaa ataaagcaat agcatcacaa | 300 |
| atttcacaaa taaagcattt ttttcactgc attctagttg tggtttgtcc aaactcatca | 360 |
| atgtatctta tcatgtctgt cgatcactta tcaaaatggt ccaggggta atgctcgccg | 420 |
| tatgtctgca ggtgtcttgc caggctctcc tgctgcttcc tcagctgggc aggcatctcc | 480 |
| tggtacacgt cggaaaacag cagattaggg ttgggctttg gcttcctctc tgcctgctcg | 540 |
| aaggcctcca tcactttccg gcggctctgc ttcctccagg ccttctcctg ctcctcatcc | 600 |
| caccagccct gggacagcag atagtgcctc agtctgctga tagggtgatc ctgcttgtcc | 660 |
| caataattca cttcgtccac agacctgtag gcagaggaat cgtcggatgt gctgtggtgg | 720 |
| ccgattctgt aggtcatggc ctcgatcaga aagggctggt tctctgccac tgcccttctc | 780 |
| cgtgcctcct ttgtggcatt atacacgcg aacacgtcgt gccgtccac cctgatggac | 840 |
| atgatgccgt agcctgggcc tctggctgcg attccatcgc ccctatactg ctcgcttgtt | 900 |
| ggggtagaga tggcgtagcc attgtttcta caaagaaga tgatagggca ctccagggtg | 960 |
| gcggcaaagt tgaagccggc gtgtgcgtcg ccctcggagg ctgctccctc tccaaaatag | 1020 |
| cagatgacca ccctattggc gttggctctc ttggcggcgt aggctgctcc cactgcctga | 1080 |
| gggatctgtg tggccagggg gctagagatg gtcacgaagt gccgctcctt acagccatag | 1140 |
| tgcactggca tctggcggcc cttgcccaga tcgctgatat tgccgtagca ctgggccata | 1200 |
| aacagctcca gaggatagtc cctgtacatc agcacgccgg cctctctata ctggccgaac | 1260 |
| accagatcgg tattgtccag ggcggcggcg ctgcccacgt gtgtgccctc ctcgccatag | 1320 |
| ttggtcatgt agaaagagat ccggccctgg cgctgggact catacaggat tctatccatt | 1380 |
| gtgttcagca gggtcataga cttgtacagc ttcagcacct tctcctttgg caggtggggg | 1440 |
| tcctcggatg gattgatgat ctggccctgc cggtccatca gcggtagat ggggatgccg | 1500 |
| ctgatcacgt ttggctggat aaactccagc ttgtcgatga actcggcaga ggcgccggga | 1560 |

```
aactgtggct tatcgtccag ggagctgaac tgctgctgct gcctaggtgg gtggctcctg    1620
gccaggcctc tggctcctgg ctgtctcagc agcagcagtg cggcctggct cagtccccga    1680
ttcagtctcc acactcttgc ggcggcgatt gcgacggcca tggtggccta gcgctagagc    1740
ttgctcccgc ccgccgcgcg cttcgctttt tatagggccg ccgccgccgc cgcctcgcca    1800
taaaaggaaa ctttcggagc gcgccgctct gattggctgc cgccgcacct ctccgcctcg    1860
ccccgccccg cccctcgccc ccatcgctgc acaaaataat taaaaaataa ataaatacaa    1920 aattggggt ggggagggg gggagatggg gagagtgaag cagaacgtgg cctcggatcc       1980
cccgggctgc agtattaata gtaatcaatt acggggtcat tagttcatag cccatatatg    2040
gagttccgcg ttacataact tacggtaaat ggcccgcctg gctgaccgcc caacgacccc    2100
cgcccattga cgtcaataat gacgtatgtt cccatagtaa cgccaatagg gactttccat    2160
tgacgtcaat gggtggagta tttacggtaa actgcccact ggcagtaca tcaagtgtat    2220 catatgccaa gtacgcccc tattgacgtc aatgacggta atggcccgc ctggcattat     2280 gcccagtaca tgaccttatg gactttcct acttggcagt acatctacgt attagtcatc    2340
gctattacca tgtcgaggcc acgttctgct tcactctccc catctccccc ccctccccac    2400
ccccaatttt gtatttattt attttttaat tattttgtgc agcgatgggg gcgagggcg    2460 gggcggggcg aggcggagag gtgcggcggc agccaatcag agcggcgcgc tccgaaagtt    2520
tccttttatg gcgaggcggc ggcggcggcg gcctataaa aagcgaagcg cgcggcgggc    2580
gggagcaagc tcgctagcac tagtgccacc atggccgtgg tcgctgctgc tgccggatgg    2640
ctgctgagac tgcgggccgc tggggctgag gacattgga ggagactgcc tggggctggg    2700
ctggcaaggg gcttcctgca ccctgcagca acagtggagg acgcagcaca gcggagacag    2760
gtggcccact tcacctttca gcccgatcct gagccacgcg agtacggcca gacacagaag    2820
atgaacctgt tccagtccgt gacctctgcc ctggacaata gcctggccaa ggatccaaca    2880
gccgtgatct ttggcgagga cgtggccttc ggcggcgtgt ttcggtgcac agtgggcctg    2940
agagacaagt acggcaagga tcgggtgttc aacaccccac tgtgcgagca gggaatcgtg    3000
ggctttggca tcggcatcgc agtgaccgga gcaacagcaa tcgcagagat ccagttcgcc    3060
gactatatct tccccgcctt tgatcagatc gtgaacgagg ccgccaagta caggtatcgc    3120
tccggcgacc tgtttaattg cggcagcctg accatcagat ccccttgggg atgcgtggga    3180
cacggcgccc tgtatcactc tcagagccca gaggccttct ttgcccactg ccccggcatc    3240
aaggtggtca tcccacggag ccccttccag gcaaagggcc tgctgctgtc ctgcatcgag    3300
gataagaacc cctgtatctt ctttgagcct aagatcctgt acagagcagc agcagaggag    3360
gtgcctatcg agccatataa tatccctctg tctcaggccg aagtgatcca ggagggaagc    3420
gacgtgaccc tggtggcatg gggaacacag gtgcacgtga tcagggaggt ggcctccatg    3480
gccaaggaga agctgggcgt gtcttgcgaa gtgatcgatc tgaggaccat catcccttgg    3540
gacgtggata caatctgtaa gtctgtgatc aagaccggcc gcctgctgat cagccacgag    3600
gcaccactga caggaggatt cgcatccgag atcagctcca ccgtgcagga ggagtgcttt    3660
ctgaatctgg aggccccaat ctctcgggtg tgcggctacg ataccccctt ccctcacatc    3720
tttgagcctt tctacatccc tgacaagtgg aagtgctacg acgtctgcg gaagatgatt    3780 aactattgag cggccgctct agagatcttt ttccctctgc aaaaattat ggggacatca     3840 tgaagccct tgagcatctg acttctggct aataaaggaa atttatttc attgcaatag     3900 tgtgttggaa ttttttgtgt ctctcactcg gcatgctggg gagagatcta ggaaccccta    3960
```

```
gtgatggagt tggccactcc ctctctgcgc gctcgctcgc tcactgaggc cgcccgggca  4020
aagcccgggc gtcgggcgac ctttggtcgc ccggcctcag tgagcgagcg agcgcgcaga  4080
gagggagtgg ccatgcagcc agctggcgta atagcgaaga ggcccgcacc gatcgccctt  4140
cccaacagtt gcgtagcctg aatggcgaat ggcgcgacgc gccctgtagc ggcgcattaa  4200
gcgcggcggg tgtggtggtt acgcgcagcg tgaccgctac acttgccagc gccctagcgc  4260
ccgctccttt cgctttcttc ccttcctttc tcgccacgtt cgccggcttt ccccgtcaag  4320
ctctaaatcg ggggctccct ttagggttcc gatttagtgc tttacggcac ctcgacccca  4380
aaaaacttga ttagggtgat ggttcacgta gtgggccatc gccctgatag acggtttttc  4440
gccctttgac gttggagtcc acgttcttta atagtggact cttgttccaa actggaacaa  4500
cactcaaccc tatctcggtc tattcttttg atttataagg gattttgccg atttcggcct  4560
attggttaaa aaatgagctg atttaacaaa aatttaacgc gaattttaac aaaatattaa  4620
cgtttacaat ttcctgatgc ggtattttct ccttacgcat ctgtgcggta tttcacaccg  4680
catatggtgc actctcagta caatctgctc tgatgccgca tagttaagcc agccccgaca  4740
cccgccaaca cccgctgacg cgccctgacg ggcttgtctg ctcccggcat ccgcttacag  4800
acaagctgtg accgtctccg ggagctgcat gtgtcagagg ttttcaccgt catcaccgaa  4860
acgcgcgaga cgaaagggcc tcgtgatacg cctattttta taggttaatg tcatgataat  4920
aatggtttct tagacgtcag gtggcacttt tcggggaaat gtgcgcggaa cccctatttg  4980
tttatttttc taaatacatt caaatatgta tccgctcatg agacaataac cctgataaat  5040
gcttcaataa tattgaaaaa ggaagagtat gagtattcaa catttccgtg tcgcccttat  5100
tccctttttt gcggcatttt gccttcctgt ttttgctcac ccagaaacgc tggtgaaagt  5160
aaaagatgct gaagatcagt tgggtgcacg agtgggttac atcgaactgg atctcaacag  5220
cggtaagatc cttgagagtt ttcgccccga agaacgtttt ccaatgatga gcacttttaa  5280
agttctgcta tgtggcgcgg tattatcccg tattgacgcc gggcaagagc aactcggtcg  5340
ccgcatacac tattctcaga atgacttggt tgagtactca ccagtcacag aaaagcatct  5400
tacggatggc atgacagtaa gagaattatg cagtgctgcc ataaccatga gtgataacac  5460
tgcggccaac ttacttctga caacgatcgg aggaccgaag gagctaaccg cttttttgca  5520
caacatgggg gatcatgtaa ctcgccttga tcgttgggaa ccggagctga atgaagccat  5580
accaaacgac gagcgtgaca ccacgatgcc tgtagcaatg gcaacaacgt tgcgcaaact  5640
attaactggc gaactactta ctctagcttc ccggcaacaa ttaatagact ggatggaggc  5700
ggataaagtt gcaggaccac ttctgcgctc ggcccttccg gctggctggt ttattgctga  5760
taaatctgga gccggtgagc gtgggtctcg cggtatcatt gcagcactgg ggccagatgg  5820
taagccctcc cgtatcgtag ttatctacac gacgggagt caggcaacta tggatgaacg  5880
aaatagacag atcgctgaga taggtgcctc actgattaag cattggtaac tgtcagacca  5940
agtttactca tatatacttt agattgattt aaaacttcat ttttaattta aaaggatcta  6000
ggtgaagatc cttttttgata atctcatgac caaaatccct taacgtgagt tttcgttcca  6060
ctgagcgtca gaccccgtag aaaagatcaa aggatcttct tgagatcctt ttttctgcg  6120 cgtaatctgc tgcttgcaaa caaaaaaacc accgctacca gcggtggttt gtttgccgga  6180
tcaagagcta ccaactcttt ttccgaaggt aactggcttc agcagagcgc agataccaaa  6240
tactgtcctt ctagtgtagc cgtagttagg ccaccacttc aagaactctg tagcaccgcc  6300
```

-continued

```
tacatacctc gctctgctaa tcctgttacc agtggctgct gccagtggcg ataagtcgtg   6360
tcttaccggg ttggactcaa gacgatagtt accggataag gcgcagcggt cgggctgaac   6420
ggggggttcg tgcacacagc ccagcttgga gcgaacgacc tacaccgaac tgagatacct   6480
acagcgtgag cattgagaaa gcgccacgct tcccgaaggg agaaaggcgg acaggtatcc   6540

ggtaagcggc agggtcggaa caggagagcg cacgagggag cttccagggg gaaacgcctg   6600
gtatctttat agtcctgtcg ggtttcgcca cctctgactt gagcgtcgat ttttgtgatg   6660
ctcgtcaggg gggcggagcc tatggaaaaa cgccagcaac gcggcctttt tacggttcct   6720
ggccttttgc tggccttttg ctcacatgtt ctttcctgcg ttatcccctg attctgtgga   6780
taaccgtatt accgcctttg agtgagctga taccgctcgc cgcagccgaa cgaccgagcg   6840
cagcgagtca gtgagcgagg aagcggaaga gcgcccaata cgcaaaccgc ctctccccgc   6900
gcgttggccg attcattaat gcagctgggc tgcagggggg gggggggggg ggtggggggg   6960
gggggggggg g                                                        6971

<210> SEQ ID NO 9
<211> LENGTH: 454
<212> TYPE: PRT
<213> ORGANISM: Bos taurus

<400> SEQUENCE: 9

Met Gln Gly Ser Ala Lys Met Ala Met Ala Val Ala Val Ala Val Ala
1               5                   10                  15

Arg Val Trp Arg Pro Ser Arg Gly Leu Gly Arg Thr Gly Leu Pro Leu
            20                  25                  30

Leu Arg Leu Leu Gly Ala Arg Gly Leu Ala Arg Phe His Pro His Arg
        35                  40                  45

Trp Gln Gln Gln Gln His Phe Ser Ser Leu Asp Asp Lys Pro Gln Phe
    50                  55                  60

Pro Gly Ala Ser Ala Glu Phe Ile Asp Lys Leu Glu Phe Ile Gln Pro
65                  70                  75                  80

Asn Val Ile Ser Gly Ile Pro Ile Tyr Arg Val Met Asp Arg Gln Gly
                85                  90                  95

Gln Ile Ile Asn Pro Ser Glu Asp Pro His Leu Pro Gln Glu Lys Val
            100                 105                 110

Leu Lys Phe Tyr Lys Ser Met Thr Leu Leu Asn Thr Met Asp Arg Ile
        115                 120                 125

Leu Tyr Glu Ser Gln Arg Gln Gly Arg Ile Ser Phe Tyr Met Thr Asn
    130                 135                 140

Tyr Gly Glu Glu Gly Thr His Val Gly Ser Ala Ala Ala Leu Asp Asp
145                 150                 155                 160

Thr Asp Leu Val Phe Gly Gln Tyr Arg Glu Ala Gly Val Leu Met Tyr
                165                 170                 175

Arg Asp Tyr Pro Leu Glu Leu Phe Met Ala Gln Cys Tyr Gly Asn Val
            180                 185                 190

Ser Asp Leu Gly Lys Gly Arg Gln Met Pro Val His Tyr Gly Cys Arg
        195                 200                 205

Glu Arg His Phe Val Thr Ile Ser Ser Pro Leu Ala Thr Gln Ile Pro
    210                 215                 220

Gln Ala Val Gly Ala Ala Tyr Ala Ala Lys Arg Ala Asn Ala Asn Arg
225                 230                 235                 240

Trp Ile Cys Tyr Phe Gly Glu Gly Ala Ala Ser Glu Gly Asp Ala His
                245                 250                 255
```

Ala Gly Phe Asn Phe Ala Ala Thr Leu Glu Cys Pro Ile Ile Phe Phe
            260                 265                 270

Cys Arg Asn Asn Gly Tyr Ala Ile Ser Thr Pro Thr Ser Glu Gln Tyr
        275                 280                 285

Arg Gly Asp Gly Ile Ala Ala Arg Gly Pro Tyr Gly Ile Leu Ser
    290                 295                 300

Ile Arg Val Asp Gly Asn Asp Val Phe Ala Val Tyr Asn Ala Thr Lys
305                 310                 315                 320

Glu Ala Arg Arg Arg Ala Val Ala Glu Asn Gln Pro Phe Leu Ile Glu
                325                 330                 335

Ala Met Thr Tyr Arg Ile Gly His His Ser Thr Ser Asp Ser Ser
            340                 345                 350

Ala Tyr Arg Ser Val Asp Glu Val Asn Tyr Trp Asp Lys Gln Asp His
        355                 360                 365

Pro Ile Ser Arg Leu Arg His His Leu Gln Ser Arg Gly Trp Trp Asp
    370                 375                 380

Asp Glu Gln Glu Lys Ala Trp Arg Lys Gln Ser Arg Lys Lys Val Met
385                 390                 395                 400

Glu Ala Phe Glu Gln Ala Glu Arg Lys Leu Lys Pro Asn Pro Ser Leu
                405                 410                 415

Ile Phe Ser Asp Val Tyr Gln Glu Met Pro Ala Gln Leu Arg Lys Gln
            420                 425                 430

Gln Glu Ser Leu Ala Arg His Leu Gln Thr Tyr Gly Glu His Tyr Pro
        435                 440                 445

Leu Asp His Phe Glu Lys
    450

<210> SEQ ID NO 10
<211> LENGTH: 444
<212> TYPE: PRT
<213> ORGANISM: Homo sapiens

<400> SEQUENCE: 10

Met Ala Val Ala Ile Ala Ala Ala Arg Val Trp Arg Leu Asn Arg Gly
1               5                   10                  15

Leu Ser Gln Ala Ala Leu Leu Leu Arg Gln Pro Gly Ala Arg Gly
            20                  25                  30

Leu Ala Arg Ser His Pro Pro Arg Gln Gln Gln Phe Ser Ser Leu
        35                  40                  45

Asp Asp Lys Pro Gln Phe Pro Gly Ala Ser Ala Glu Phe Ile Asp Lys
50                  55                  60

Leu Glu Phe Ile Gln Pro Asn Val Ile Ser Gly Ile Pro Ile Tyr Arg
65                  70                  75                  80

Val Met Asp Arg Gln Gly Gln Ile Ile Asn Pro Ser Glu Asp Pro His
                85                  90                  95

Leu Pro Lys Glu Lys Val Leu Lys Leu Tyr Lys Ser Met Thr Leu Leu
            100                 105                 110

Asn Thr Met Asp Arg Ile Leu Tyr Glu Ser Gln Arg Gln Gly Arg Ile
        115                 120                 125

Ser Phe Tyr Met Thr Asn Tyr Gly Glu Glu Gly Thr His Val Gly Ser
    130                 135                 140

Ala Ala Ala Leu Asp Asn Thr Asp Leu Val Phe Gly Gln Tyr Arg Glu
145                 150                 155                 160

Ala Gly Val Leu Met Tyr Arg Asp Tyr Pro Leu Glu Leu Phe Met Ala

```
                165                 170                 175
Gln Cys Tyr Gly Asn Ile Ser Asp Leu Gly Lys Gly Arg Gln Met Pro
            180                 185                 190

Val His Tyr Gly Cys Lys Glu Arg His Phe Val Thr Ile Ser Ser Pro
            195                 200                 205

Leu Ala Thr Gln Ile Pro Gln Ala Val Gly Ala Ala Tyr Ala Ala Lys
            210                 215                 220

Arg Ala Asn Ala Asn Arg Trp Ile Cys Tyr Phe Gly Glu Gly Ala Ala
225                 230                 235                 240

Ser Glu Gly Asp Ala His Ala Gly Phe Asn Phe Ala Ala Thr Leu Glu
            245                 250                 255

Cys Pro Ile Ile Phe Phe Cys Arg Asn Asn Gly Tyr Ala Ile Ser Thr
            260                 265                 270

Pro Thr Ser Glu Gln Tyr Arg Gly Asp Gly Ile Ala Ala Arg Gly Pro
            275                 280                 285

Gly Tyr Gly Ile Met Ser Ile Arg Val Asp Gly Asn Asp Val Phe Ala
            290                 295                 300

Val Tyr Asn Ala Thr Lys Glu Ala Arg Arg Arg Ala Val Ala Glu Asn
305                 310                 315                 320

Gln Pro Phe Leu Ile Glu Ala Met Thr Tyr Arg Ile Gly His His Ser
            325                 330                 335

Thr Ser Asp Asp Ser Ser Ala Tyr Arg Ser Val Asp Glu Val Asn Tyr
            340                 345                 350

Trp Asp Lys Gln Asp His Pro Ile Ser Arg Leu Arg His Tyr Leu Leu
            355                 360                 365

Ser Gln Gly Trp Trp Asp Glu Glu Gln Glu Lys Ala Trp Arg Lys Gln
    370                 375                 380

Ser Arg Arg Lys Val Met Glu Ala Phe Glu Gln Ala Glu Arg Lys Pro
385                 390                 395                 400

Lys Pro Asn Pro Asn Leu Leu Phe Ser Asp Val Tyr Gln Glu Met Pro
            405                 410                 415

Ala Gln Leu Arg Lys Gln Gln Glu Ser Leu Ala Arg His Leu Gln Thr
            420                 425                 430

Tyr Gly Glu His Tyr Pro Leu Asp His Phe Asp Lys
            435                 440
```